United States Patent [19]
Barenkamp

[11] Patent Number: 5,928,651
[45] Date of Patent: Jul. 27, 1999

[54] GENE ENCODING HIGH MOLECULAR SURFACE PROTEIN-2 NON-TYPEABLE HAEMOPHILUS

[75] Inventor: Stephen J. Barenkamp, Webster Grove, Mo.

[73] Assignees: St. Louis University; Washington University, both of St. Louis, Mo.

[21] Appl. No.: 08/728,470

[22] Filed: Oct. 10, 1996

Related U.S. Application Data

[63] Continuation of application No. 08/302,832, filed as application No. PCT/US93/02166, Mar. 16, 1993, Pat. No. 5,603,938.

[51] Int. Cl.$^6$ ........................ A61K 39/102; C07H 19/00; C07H 21/02; C07H 21/04
[52] U.S. Cl. ..................................... 424/256.1; 424/184.1; 536/22.1; 536/23.1; 536/23.7; 435/69.1; 435/69.3
[58] Field of Search ........................ 424/256.1; 536/22.1, 536/23.1, 23.7, 24.1; 435/69.1, 69.3

[56] References Cited

PUBLICATIONS

Pediatric Infectious Disease Journal, vol. 9, No. 5, issued May 1990, S.J. Barenkamp et al., "Development of Serum Bactericidal Activity Following Nontypable *Haemophilus influenzae* Acute Otitis Media", pp. 333–339, see entire document.

Journal of Clinical Microbiology, vol. 29, No. 11, issued Nov. 1991, A.C. Caputa et al., "110 Kilodalton Recombinant Protein which is Immunoreactive with Sera from Humans, Dogs, and Horses with Lyme Borreliosis", pp. 2418–2423, see entire document.

Joint Meeting of the American Pediatric Society and the Society for Pediatric Research, May 07–10, 1990, S.J. Barenkamp, "Cloning and Expression of Genes for Nontypable *Haemophilus influenzae* (NTHI) High Molecular Weight (HMW) Outer Membrane Proteins which are Targets of Bactericidal Antibody", Abstract 983, Pediatric Research, vol. 27, (4 part 2).

The Journal of Infectious Diseases, vol. 165 (Suppl.), issued Aug. 1992, S.J.Barenkamp, "Outer Membrane Protein and Lipopolysaccharides of Nontypeable *Haemophilus influenzae*", pp. S181 –S184, see entire document.

Infection and Immunity, vol. 60(4), issued Apr. 1992, S.J.Barenkamp et al, Cloning, Expression and DNA Sequence Analysis of Genes Encoding Nontypable *Haemophilus influenzae* High–Molecular–Weight Surface–Exposed Proteins Related to Filamentous Hemagglutinin of *Bordetella pertussis* pp. 1302–1313, see entire document.

Infection and Immunity, vol. 56(1), issued Jan. 1988, E.J. Hansen, Immune Enhancement of Pulmonary Clearance on Nontypable *Haemophilus influenzae*, pp. 182–190, see entire document, especially Figures 3 and 4.

Infection and Immunity, vol. 52(2), issued May 1986, S.J. Barenkamp, "Protection by Serum Antibodies in Experimental Nontypable *Haemophilus influenzae* Otitis Media", pp. 572–578, see Figures 1 and 2.

Proceedings of the National Academy of Sciences USA, vol. 80, issued Mar. 1983, R.A. Young et al., "Efficient Isolation of Genes by Using Antibody Probes", pp. 1194–1198, see entire document.

Infection and Immunity, vol. 45(3), issued Sep. 1984, R. Schneerson et al, "Serum Antibody Responses of Juvenile and Infant Rhesus Monkeys Injected with *Haemophilus influenzae* Type b and Pneumococcus Type 6A Capsular Polysaccharide–Protein Conjugates", pp. 582–591, see entire document.

Journal of Molecular Biology, vol. 157, issued 1982, J. Kyte et al, "A Simple Method for Displaying the Hydropathic Character of a Protein", pp. 105–132, see entire document.

Proceedings of the National Academy of Sciences, vol. 78(6), issued Jun. 1981, T.P.Hopp et al., "Prediction of Protein Antigenic Determinants from Amino Acid Sequences", pp. 3824–3828, see entire document.

Pediatr. Infect. Dis. J., 9: 333–339, 1990, Stephen J. Barenkamp and Frank F. Bodor, "Development of Serum Bacterial Activity Following Nontypable *Haemophilus influenzae* Acute Otitis Media".

Green et al, Infection and Immunity 61:1950–1957, 1993.

Erwin et al, Can. Journ.of Microbioligy 34:, 723–729, 1988.

Thomas et al., Infection and Immunity, 58: 1909–1913, 1990.

Barenkamp, Pediatric Research vol. 29, 167A, Abstract 985, 1991.

Barenkamp, Abstract 983, Pediatric Research vol. 27.

Houghten et al, Vaccine 86, pp. 21 to 25.

*Primary Examiner*—Hazel F. Sidberry
*Attorney, Agent, or Firm*—Sim & McBurney

[57] ABSTRACT

High molecular weight surface proteins of non-typeable *Haemophilus influenzae* which exhibit immunogenic properties and genes encoding the same are described. Specifically, genes coding for two immunodominant high molecular weight proteins, HMW1 and HMW2, have been cloned, expressed and sequenced, while genes coding for high molecular proteins HKW3 and HMW4 have been cloned, expressed and partially sequenced.

3 Claims, 68 Drawing Sheets

FIG. 1A. DNA SEQUENCE OF HIGH MOLECULAR WEIGHT PROTEIN I (HMW1)

```
  1  ACAGGGTTCT CTTAATACTA GTACAAACCC ACAATAAAAT ATGACAAACA
 51  ACAATTACAA CACCTTTTTT GCAGTCTATA TGCAAATATT TTAAAAAATA
101  GTATAAATCC GCCATATAAA ATGGTATAAT CTTTCATCTT TCATCTTTCA
151  TCTTTCATCT TTCATCTTTC ATCTTTCATC TTTCATCTTT CATCTTTCAT
201  CTTTCATCTT TCATCTTTCA TCTTTCATCT TTCATCTTTC ACATGCCCTG
251  ATGAACCGAG GGAAGGGAGG GAGGGCAAG AATGAAGAGG GAGCTGAACG
301  AACGCAAATG ATAAAGTAAT TTAATTGTTC AACTAACCTT AGGAGAAAAT
351  ATGAACAAGC TATATCGTCT CAAATTCAGC AAACGCCTGA ATGCTTTGGT
401  TGCTGTGTCT GAATTGGCAC GGGGTTGTGA CCATTCCACA GAAAAGGCA
451  GCGAAAAACC TGCTCGCATG AAAGTGCGTC ACTTAGCGTT AAAGCCACTT
501  TCCGCTATGT TACTATCTTT AGGTGTAACA TCTATTCCAC AATCTGTTTT
551  AGCAAGCGGC TTACAAGGAA TGGATGTAGT ACACGGCACA GCCACTATGC
601  AAGTAGATGG TAATAAAACC ATTATCCGCA ACAGTGTTGA CGATATCATT
651  AATTGGAAAC AATTTAACAT CGACCAAAAT GAAATGGTGC AGTTTTACA
701  AGAAAACAAC AACTCCGCCG TATTCAACCG TGTTACATCT AACCAAATCT
```

FIG. 1B.

```
 751  CCCAATTAAA AGGGATTTTA GATTCTAACG GACAAGTCTT TTTAATCAAC
 801  CCAAATGGTA TCACAATAGG TAAAGACGCA ATTATTAACA CTAATGGCTT
 851  TACGGCTTCT ACGCTAGACA TTTCTAACGA AAACATCAAG GCGCGTAATT
 901  TCACCTTCGA GCAAACCAAA GATAAAGCGC TCGCTGAAAT TGTGAATCAC
 951  GGTTTAATTA CTGTCGGTAA AGACGGCAGT GTAAATCTTA TTGGTGGCAA
1001  AGTGAAAAAC GAGGGTGTGA TTAGCGTAAA TGGTGGCAGC ATTTCTTTAC
1051  TCGCAGGGCA AAAAATCACC ATCAGCGATA TAATAAACCC AACCATTACT
1101  TACAGCATTG CCGCGCCTGA AAATGAAGCG GTCAATCTGG GCGATATTTT
1151  TGCCAAAGGC GGTAACATTA ATGTCCCGTGC TGCCACTATT CGAAACCAAG
1201  GTAAACTTTC TGCTGATTCT GTAAGCAAAG ATAAAAGCGG CAATATTGTT
1251  CTTTCCGCCA AAGAGGGTGA AGCGGAAATT GGCGGTGTAA TTTCCGCTCA
1301  AAATCAGCAA GCTAAAGGCG GCAAGCTGAT GATTACAGGC GATAAAGTCA
1351  CATTAAAAAC AGGTGCAGTT ATCGACCTTT CAGGTAAAGA AGGGGAGAA
1401  ACTTACCTTG GCGGTGACGA GCGCGGCGAA GGTAAAAAGG GCATTCAATT
1451  AGCAAAGAAA ACCTCTTTAG AAAAAGGCTC AACCATCAAT GTATCAGGCA
1501  AAGAAAAAGG CGGACGCGCT ATTGTGTGGG GCGATATTGC GTTAATTGAC
```

FIG. 1C.

```
1551 GGCAATATTA ACGCTCAAGG TAGTGGTGAT ATCGCTAAAA CCGGTGGTTT
1601 TGTGGAGACG TCGGGGCATG ATTTATTCAT CAAAGACAAT GCAATTGTTG
1651 ACGCCAAAGA GTGGTTGTTA GACCCGGATA ATGTATCTAT TAATGCAGAA
1701 ACAGCAGGAC GCAGCAATAC TTCAGAAGAC GATGAATACA CGGGATCCGG
1751 GAATAGTGCC AGCACCCCAA AACGAAACAA AGAAAAGACA ACATTAACAA
1801 ACACAACTCT TGAGAGTATA CTAAAAAAAG GTACCTTTGT TAACATCACT
1851 GCTAATCAAC GCATCTATGT CAATAGCTCC ATTAATTTAT CCAATGGCAG
1901 CTTAACTCTT TGGAGTGAGG GTCGGAGCGG TGGCGGCGTT GAGATTAACA
1951 ACGATATTAC CACCGGTGAT GATACCAGAG TCATAAAAAT AACAATTTAC
2001 TCAGGCGGCT GGGTTGATGT AACAAGATAT ATCTCACTCG GGGCGCAAGG
2051 TAACATAAAC ATTACAGCTA GGGACTATTA CGCCCTTTGAG AAAGGAAGCA
2101 ACCAAGTCAT TACAGGTCAA TCTAAACGGC CCTCAGGCAA TCAAAAAGGT
2151 TTTAGATTTA ATAATGTCTC TCTAAACGGC ACTGGCAGCG GACTGCAATT
2201 CACCACTAAA AGAACCAATA AATACGCTAT CACAAATAAA TTTGAAGGGA
2251 CTTTAAATAT TTCAGGGAAA GTGAACATCT CAATGGTTTT ACCTAAAAAT
2301 GAAAGTGGAT ATGATAAATT CAAAGGACGC ACTTACTGGA ATTAACCTC
```

FIG. 1D.

```
2351 CTTAAATGTT TCCGAGAGTG GCGAGTTTAA CCTCACTATT GACTCCAGAG
2401 GAAGCGATAG TGCAGGCACA CTTACCCAGC CTTATAATTT AAACGGTATA
2451 TCATTCAACA AAGACACTAC CTTTAATGTT GAACGAAATG CAAGAGTCAA
2501 CTTGACATC AAGGCACCAA TAGGGATAAA TAAGTATTCT AGTTTGAATT
2551 ACGCATCATT TAATGGAAAC ATTTCAGTTT CGGGAGGGGG GAGTGTTGAT
2601 TTCACACTTC TCGCCTCATC CTCTAACGTC CAAACCCCCG GTGTAGTTAT
2651 AAATTCTAAA TACTTTAATG TTTCAACAGG GTCAAGTTTA AGATTTAAAA
2701 CTTCAGGCTC AACAAAAACT GGCTTCTCAA TAGAGAAAGA TTTAACTTTA
2751 AATGCCACCG GAGGCAACAT AACACTTTTG CAAGTTGAAG GCACCGATGG
2801 AATGATTGGT AAAGGCATTG TAGCCAAAAA AAACATAACC TTTGAAGGAG
2851 GTAACATCAC CTTTGGCTCC AGGAAAGCCG TAACAGAAAT CGAAGGCAAT
2901 GTTACTATCA ATAACAACGC TAACGTCACT CTTATCGGTT CGGATTTTGA
2951 CAACCATCAA AAACCTTTAA CTATTAAAAA AGATGTCATC ATTAATAGCG
3001 GCAACCTTAC CGCTGGAGGC AATATTGTCA ATATAGCCGG AAATCTTACC
3051 GTTGAAAGTA ACGCTAATTT CAAAGCTATC ACAAATTTCA CTTTTAATGT
3101 AGGCGGCTTG TTTGACAACA AAGGCAATTC AAATATTTCC ATTGCCAAAG
3151 GAGGGGCTCG CTTTAAAGAC ATTGATAATT CCAAGAATTT AAGCATCACC
```

FIG. 1E.

```
3201  ACCAACTCCA  GCTCCACTTA  CCGCACTATT  ATAAGCGGCA  ATATAACCAA
3251  TAAAAACGGT  GATTTAAATA  TTACGAACGA  AGGTAGTGAT  ACTGAAATGC
3301  AAATTGGCGG  CGATGTCTCG  CAAAAAGAAG  GTAATCTCAC  GATTCTTCT
3351  GACAAAATCA  ATATTACCAA  ACAGATAACA  ATCAAGGCAG  GTGTTGATGG
3401  GGAGAATTCC  GATTCAGACG  CGACAAACAA  TGCCAATCTA  ACCATTAAAA
3451  CCAAAGAATT  GAAATTAACG  CAAGACCTAA  ATATTTCAGG  TTTCAATAAA
3501  GCAGAGATTA  CAGCTAAAGA  TGGTAGTGAT  TTAACTATTG  GTAACACCAA
3551  TAGTGCTGAT  GGTACTAATG  CCAAAAAAGT  AACCTTTAAC  CAGGTTAAAG
3601  ATTCAAAAAT  CTCTGCTGAC  GGTCACAAGG  TGACACTACA  CAGCAAAGTG
3651  GAAACATCCG  GTAGTAATAA  CAACACTGAA  GATAGCAGTG  ACAATAATGC
3701  CGGCTTAACT  ATCGATGCAA  AAAATGTAAC  AGTAAACAAC  AATATTACTT
3751  CTCACAAAGC  AGTGAGCATC  TCTGCGACAA  GTGGAGAAAT  TACCACTAAA
3801  ACAGGTACAA  CCATTAACGC  AACCACTGGT  AACGTGGAGA  TAACCGCTCA
3851  AACAGGTAGT  ATCCTAGGTG  GAATTGAGTC  CAGCTCTGGC  TCTGTAACAC
3901  TTACTGCAAC  CGAGGGCGCT  CTTGCTGTAA  GCAATATTTC  GGGCAACACC
3951  GTTACTGTTA  CTGCAAATAG  CGGTGCATTA  ACCACTTTGG  CAGGCTCTAC
```

FIG. 1F.

```
4001 AATTAAAGGA ACCGAGAGTG TAACCACTTC AAGTCAATCA GGCGATATCG
4051 GCGGTACGAT TTCTGGTGGC ACAGTAGAGG TTAAAGCAAC CGAAAGTTTA
4101 ACCACTCAAT CCAATTCAAA AATTAAAGCA ACAACAGGCG AGGCTAACGT
4151 AACAAGTGCA ACAGGTACAA TTGGTGGTAC GATTTCCGGT AATACGGTAA
4201 ATGTTACGGC AAACGCTGGC GATTTAACAG TTGGGAATGG CGCAGAAATT
4251 AATGCGACAG AAGGAGCTGC AACCTTAACT ACATCATCGG GCAAATTAAC
4301 TACCGAAGCT AGTTCACACA TTACTTCAGC CAAGGGTCAG GTAAATCTTT
4351 CAGCTCAGGA TGGTAGCGTT GCAGGAAGTA TTAATGCCGC CAATGTGACA
4401 CTAAATACTA CAGGCACTTT AACTACCGTG AAGGGTTCAA ACATTAATGC
4451 AACCAGCGGT ACCTTGGTTA TTAACGCAAA AGACGCTGAG CTAAATGGCG
4501 CAGCATTGGG TAACCACACA GTGGTAAATG CAACCAACGC AAATGGCTCC
4551 GGCAGCGTAA TCGCGACAAC CTCAAGCAGA GTGAACATCA CTGGGGATTT
4601 AATCACAATA AATGGATTAA ATATCATTTC AAAAAACGGT ATAAACACCG
4651 TACTGTTAAA AGGCGTTAAA ATTGATGTGA AATACATTCA ACCGGGTATA
4701 GCAAGCGTAG ATGAAGTAAT TGAAGCGAAA CGCATCCTTG AGAAGGTAAA
4751 AGATTTATCT GATGAAGAAA GAGAAGCGTT AGCTAAACTT GGAGTAAGTG
4801 CTGTACGTTT TATTGAGCCA AATAATACAA TTACAGTCGA TACACAAAT
```

FIG. 1G.

```
4851  GAATTGCAA CCAGACCATT AAGTCGAATA GTGATTTCTG AAGGCAGGGC
4901  GTGTTCTCA AACAGTGATG GCGCGACGGT GTGCGTTAAT ATCGCTGATA
4951  ACGGGCGGTA GCGGTCAGTA ATTGACAAGG TAGATTTCAT CCTGCAATGA
5001  AGTCATTTTA TTTTCGTATT ATTTACTGTG TGGGTTAAAG TTCAGTACGG
5051  GCTTACCCA TCTTGTAAAA AATTACGGAG AATACAATAA AGTATTTTTA
5101  ACAGGTTATT ATTATG
```

FIG. 2A. AMINO ACID SEQUENCE OF HIGH MOLECULAR WEIGHT PROTEIN I

```
  1  MNKIYRLKFS  KRLNALVAVS  ELARGCDHST  EKGSEKPARM  KVRHLALKPL
 51  SAMLLSLGVT  SIPQSVLASG  LQGMDVVHGT  ATMQVDGNKT  IIRNSVDAII
101  NWKQFNIDQN  EMVQFLQENN  NSAVFNRVTS  NQISQLKGIL  DSNGQVFLIN
151  PNGITIGKDA  IINTNGFTAS  TLDISNENIK  ARNFTFEQTK  DKALAEIVNH
201  GLITVGKDGS  VNLIGGKVKN  EGVISVNGGS  ISLLAGQKIT  ISDIINPTIT
251  YSIAAPENEA  VNLGDIFAKG  GNINVRAATI  RNQGKLSADS  VSKDKSGNIV
301  LSAKEGEAEI  GGVISAQNQQ  AKGGKLMITG  DKVTLKTGAV  IDLSGKEGGE
351  TYLGGDERGE  GKNGIQLAKK  TSLEKGSTIN  VSGKEKGGRA  IVWGDIALID
401  GNINAQGSGD  IAKTGGFVET  SGHDLFIKDN  AIVDAKEWLL  DFDNVSINAE
451  TAGRSNTSED  DEYTGSGNSA  STPKRNKEKT  TLTNTTLESI  LKKGTFVNIT
501  ANQRIYVNSS  INLSNGSLTL  WSEGRSGGGV  EINNDITTGD  DTRGANLTIY
551  SGGWVDVHKN  ISLGAQGNIN  ITAKQDIAFE  KGSNQVITGQ  GTITSGNQKG
601  FRFNNVSLNG  TGSGLQFTTK  RTNKYAITNK  FEGTLNISGK  VNISMVLPKN
651  ESGYDKFKGR  TYWNLTSLNV  SESGEFNLTI  DSRGSDSAGT  LTQPYNLNGI
701  SFNKDTTFNV  ERNARVNFDI  KAPIGINKYS  SLNYASFNGN  ISVSGGGSVD
```

FIG. 2B.

```
 751 FTLLASSSNV QTPGVVINSK YFNVSTGSSL RFKTSGSTKT GFSIEKDLTL
 801 NATGGNITLL QVEGTDGMIG KGIVAKKNIT FEGGNITFGS RKAVTEIEGN
 851 VTINNNANVT LIGSDFDNHQ KPLTIKKDVI INSGNLTAGG NIVNIAGNLT
 901 VESNANFKAI TNFTFNVGGL FDNKGNSNIS IAKGGARFKD IDNSKNLSIT
 951 TNSSSTYRTI ISGNITNKNG DLNITNEGSD TEMQIGGDVS QKEGNLTISS
1001 DKINITKQIT IKAGVDGENS DSDATNNANL TIKTKELKLT QDLNISGFNK
1051 AEITAKDGSD LTIGNTNSAD GTNAKKVTFN QVKDSKISAD GHKVTLHSKV
1101 ETSGSNNNTE DSSDNNAGLT IDAKNVTVNN NITSHKAVSI SATSGEITTK
1151 TGTTINATTG NVEITAQTGS ILGGIESSSG SVTLTATEGA LAVSNISGNT
1201 VTVTANSGAL TTLAGSTIKG TESVTTSSQS GDIGGTISGG TVEVKATESL
1251 TTQSNSKIKA TTGEANVTSA TGTIGGTISG NTVNVTANAG DLTVGNGAEI
1301 NATEGAATLT TSSGKLTTEA SSHITSAKGQ VNLSAQDGSV AGSINAANVT
1351 LNTTGTLTTV KGSNINATSG TLVINAKDAE LNGAALGNHT VVNATNANGS
1401 GSVIATTSSR VNITGDLITI NGLNIISKNG INTVLLKGVK IDVKYIQPGI
1451 ASVDEVIEAK RILEKVKDLS DEEREALAKL GVSAVRFIEP NNTITVDTQN
1501 EFATRPLSRI VISEGRACFS NSDGATVCVN IADNGR
```

FIG. 3A. AMINO ACID SEQUENCE OF HIGH MOLECULAR WEIGHT PROTEIN II (HMW2)

```
  1  TAAATATACA AGATAATAAA AATAAATCAA GATTTTGTG ATGACAAACA
 51  ACAATTACAA CACCTTTTTT GCAGTCTATA TGCAAATATT TTAAAAAAAT
101  AGTATAAATC CGCCATATAA AATGGTATAA TCTTTCATCT TTCATCTTTA
151  ATCTTTCATC TTTCATCTTT CATCTTTCAT CTTTCATCTT TCATCTTTCA
201  TCTTTCATCT TTCATCTTTC ATCTTTCATC TTTCATCTTT CACATGAAAT
251  GATGAACCGA GGGAAGGGAG GGAGGGGCAA GAATGAAGAG GGAGCTGAAC
301  GAACGCAAAT GATAAAGTAA TTTAATTGTT CAACTAACCT TAGGAGAAAA
351  TATGAACAAG ATATATCGTC TCAAATTCAG CAAACGCCTG AATGCTTTGG
401  TTGCTGTGTC TGAATTGGCA CGGGGTTGTG ACCATTCCAC AGAAAAAGGC
451  TTCCGCTATG TTACTATCTT TAGGTGTAAC CACTTAGCGT TAAAGCCACT
501  TTCCGCTATG TTACTATCTT TAGGTGTAAC ATCTATTCCA CAATCTGTTT
551  TAGCAAGCGG CTTACAAGGA ATGGATGTAG TACACGGCAC AGCCACTATG
601  CAAGTAGATG GTAATAAAAC CATTATCCGC AACAGTGTTG ACGCTATCAT
651  TAATTGAAAA CAATTTAACA TCGACCAAAA TGAAATGGTG CAGTTTTTAC
701  AAGAAAACAA CAACTCCGCC GTATTCAACC GTGTTACATC TAACCAAATC
```

FIG. 3B.

```
 751  TCCCAATTAA  AAGGGATTTT  AGATTCTAAC  GGACAAGTCT  TTTTAATCAA
 801  CCCAAATGGT  ATCACAATAG  GTAAAGACGC  AATTATTAAC  ACTAATGGCT
 851  TTACGGCTTC  TACGCTAGAC  ATTTCTAACG  AAAACATCAA  GGCGCGTAAT
 901  TTCACCTTCG  AGCAAACCAA  AGATAAAGCG  CTCGCTGAAA  TTGTGAATCA
 951  CGGTTTAATT  ACTGTCGGTA  AAGACGGCAG  TGTAAATCTT  ATTGGTGGCA
1001  AAGTGAAAAA  CGAGGGTGTG  ATTAGCGTAA  ATGGTGGCAG  CATTTCTTTA
1051  CTCGCAGGGC  AAAAAATCAC  CATCAGCGAT  ATAATAAACC  CAACCATTAC
1101  TTACAGCATT  GCCGCGCCTG  AAAATGAAGC  GGTCAATCTG  GGCGATATTT
1151  TTGCCAAAGG  CGGTAACATT  AATGTCCGTG  CTGCCACTAT  TCGAAACCAA
1201  GGTAAACTTT  CTGCTGATTC  TGTAAGCAAA  GATAAAAGCG  GCAATATTGT
1251  TCTTTCCGCC  AAAGAGGGTG  AAGCGGAAAT  TGGCGGTGTA  ATTTCCGCTC
1301  AAAATCAGCA  AGCTAAAGGC  GGCAAGCTGA  TGATTACAGG  CGATAAAGTC
1351  ACATTAAAAA  CAGGTGCAGT  TATCGACCTT  TCAGGTAAAG  AAGGGGAGA
1401  AACTTACCTT  GGCGGTGACG  AGCGCGGCGA  AGTAAAAAAC  GGCATTCAAT
1451  TAGCAAAGAA  AACCTCTTTA  GAAAAAGGCT  CAACCATCAA  TGTATCAGGC
1501  AAAGAAAAAG  GCGGACGCGC  TATTGTGTGG  GGCGATATTG  CGTTAATTGA
```

FIG. 3C.

```
1551  CGGCAATATT AACGCTCAAG GTAGTGGTGA TATCGCTAAA ACCGGTGGTT
1601  TTGTGGAGAC ATCGGGGCAT TATTTATCCA TTGACAGCAA TGCAATTGTT
1651  AAAACAAAAG AGTGGTTGCT AGACCCTGAT GATGTAACAA TTGAAGCCGA
1701  AGACCCCCTT CGCAATAATA CCGGTATAAA TGATGAATTC CCAACAGGCA
1751  CCGGTGAAGC AAGCGACCCT AAAAAAAATA GCGAACTCAA AACAACGCTA
1801  ACCAATACAA CTATTTCAAATTATCTGAAA AACGCCTGAA CAATGAATAT
1851  AACGGCATCA AGAAAACTTA CCGTTAATAG CTCAATCAAC ATCGGAAGCA
1901  ACTCCCACTT AATTCTCCAT AGTAAAGGTC AGCCGTGGCGG AGGCGTTCAG
1951  ATTGATGGAG ATATTACTTC TAAAGGCGGA AATTTAACCA TTTATTCTGG
2001  CGGATGGGTT GATGTTCATA AAAATATTAC GCTTGATCAG GGTTTTTTAA
2051  ATATTACCGC CGCTTCCGTA GCTTTTGAAG GTGGAAATAA CAAAGCACGC
2101  GACGCGGCAA ATGCTAAAAT TGTCGCCCAG GGCACTGTAA CCATTACAGG
2151  AGAGGGAAAA GATTTCAGGG CTAACAACGT ATCTTTAAAC GGAACGGGTA
2201  AAGGTCTGAA TATCATTTCA TCAGTGAATA ATTTAACCCA CAATCTTAGT
2251  GGCACAATTA ACATATCTGG GAATATAACA ATTAACCAAA CTACGAGAAA
2301  GAACACCTCG TATTGGCAAA CCAGCCATGA TTCGCACTGG AACGTCAGTG
2351  CTCTTAATCT AGAGACAGGC GCAAATTTTA CCTTTATTAA ATACATTTCA
```

FIG. 3D.

```
2401 AGCAATAGCA AAGGCTTAAC AACACAGTAT AGAAGCTCTG CAGGGGTGAA
2451 TTTTAACGGC GTAAATGGCA ACATGTCATT CAATCTCAAA GAAGGAGCGA
2501 AAGTTAATTT CAAATTAAAA CCAAACGAGA ACATGAACAC AAGCAAACCT
2551 TTACCAATTC GGTTTTTAGC CAATATCACA GCCACTGGTG GGGCTCTGT
2601 TTTTTTTGAT ATATATGCCA ACCATTCTGG CAGAGGGGCT GAGTTAAAAA
2651 TGAGTGAAAT TAATATCTCT AACGGCGCTA ATTTTACCTT AAATTCCCAT
2701 GTTCGCGGCG ATGACGCTTT TAAAATCAAC AAAGACTTAA CCATAAATGC
2751 AACCAATTCA AATTTCAGCC TCAGACAGAC GAAAGATGAT TTTTATGACG
2801 GGTACGCACG CAATGCCATC AATTCAACCT ACAACATATC CATTCTGGGC
2851 GGTAATGTCA CCCTTGGTGG ACAAAACTCA AGCAGCAGCA TTACGGGGAA
2901 TATTACTATC GAGAAAGCAG CAAATGTTAC GCTAGAAGCC AATAACGCCC
2951 CTAATCAGCA AAACATAAGG GATAGAGTTA TAAAACTTGG CAGCTTGCTC
3001 GTTAATGGGA GTTTAAGTTT AACTGGCGAA AATGCAGATA TTAAAGGCAA
3051 TCTCACTATT TCAGAAAGCG CCACTTTTAA AGGAAAGACT AGAGATACCC
3101 TAAATATCAC CGGCAATTTT ACCAATAATG GCACTGCCGA AATTAATATA
3151 ACACAAGGAG TGGTAAAACT TGGCAATGTT ACCAATGATG GTGATTTAAA
```

FIG. 3E.

```
3201  CATTACCACT  CACGCTAAAC  GCAACCAAAG  AAGCATCATC  GGCGGAGATA
3251  TAATCAACAA  AAAAGGAAGC  TTAAATATTA  CAGACAGTAA  TAATGATGCT
3301  GAAATCCAAA  TTGGCGGCAA  TATCTCGCAA  AAAGAAGGCA  ACCTCACGAT
3351  TTCTTCCGAT  AAAATTAATA  TCACCAAACA  GATAACAATC  AAAAAGGGTA
3401  TTGATGGAGA  GGACTCTAGT  TCAGATGCGA  CAAGTAATGC  CAACCTAACT
3451  ATTAAAACCA  AAGAATTGAA  ATTGACAGAA  GACCTAAGTA  TTTCAGTTTT
3501  CAATAAAGCA  GAGATTACAG  CCAAAGATGG  TAGAGATTTA  ACTATTGGCA
3551  ACAGTAATGA  CGGTAACAGC  GGTGCCGAAG  CCAAAACAGT  AACTTTTAAC
3601  AATGTTAAAG  ATTCAAAAAT  CTCTGCTGAC  GGTCACAATG  TGACACTAAA
3651  TAGCAAAGTG  AAAACATCTA  GCAGCAATGG  CGGACGTGAA  AGCAATAGCG
3701  ACAACGATAC  CGGCTTAACT  ATTACTGCAA  AAAATGTAGA  AGTAAACAAA
3751  GATATTACTT  CTCTCAAAAC  AGTAAATATC  ACCGCGTCGG  AAAAGGTTAC
3801  CACCACAGCA  GGCTCGACCA  TTAACGCAAC  AAATGGCAAA  GCAAGTATTA
3851  CAACCAAAAC  AGGTGATATC  AGCGGTACGA  TTTCCGGTAA  CACGGTAAGT
3901  GTTAGCGCGA  CTGGTGATTT  AACCACTAAA  TCCGGCTCAA  AAATTGAAGC
3951  GAAATCGGGT  GAGGCTAATG  TAACAAGTGC  AACAGGTACA  ATTGGCGGTA
```

FIG. 3F.

```
4001 CAATTCCCGG TAATACGGTA AATGTTACGG CAAACGCTGG CGATTAACA
4051 GTTGGGAATG GCGCAGAAAT TAATGCGACA GAAGGAGCTG CAACCCTTAAC
4101 CGCAACAGGG AATACCTTGA CTACTGAAGC CGGTTCTAGC ATCACTTCAA
4151 CTAAGGGTCA GGTAGACCTC TTGGCTCAGA ATGGTAGCAT CGCAGGAAGC
4201 ATTAATGCTG CTAATGTGAC ATTAAATACT ACAGGCACCT TAACCACCGT
4251 GGCCAGGCTCG GATATTAAAG CAACCAGCGG CACCCTTGTT ATTAACGCAA
4301 AAGATGCTAA GCTAAATGGT GATGCATCAG GTGATAGTAC AGAAGTGAAT
4351 GCAGTCAACG CAAGCGGCTC TGGTAGTGTG ACTGCGGCAA CCTCAAGCAG
4401 TGTGAATATC ACTGGGGATT TAAACACAGT AAATGGGTTA AATATCATTT
4451 CGAAAGATGG TAGAAACACT GTGCGCTTAA GAGGCAAGGA AATTGAGGTG
4501 AAATATATCC AGCCAGGTGT AGCAAGTGTA GAAGAAGTAA TTGAAGCGAA
4551 ACGCGTCCTT GAAAAAGTAA AAGATTTATC TGATGAAGAA AGAGAAACAT
4601 TAGCTAAACT TGGTGTAAGT GCTGTACGTT TTGTTGAGCC AAATAATACA
4651 ATTACAGTCA ATACACAAAA TGAATTTACA ACCAGACCGT CAAGTCAAGT
4701 GATAATTTCT GAAGGTAAGG CGTGTTTCTC AAGTGGTAAT GGCGCACGAG
4751 TATGTACCAA TGTTGCTGAC GATGGACAGC CGTAGTCAGT AATTGACAAG
4801 GTAGATTTCA TCCTGCAATG AAGTCATTTT ATTTTCGTAT TATTTACTGT
```

FIG. 3G.

```
4851  GTGGGTTAAA GTTCAGTACG GGCTTTACCC ATCTTGTAAA AAATTACGGA
4901  GAATACAATA AAGTATTTTT AACAGGTTAT TATTATG
```

FIG. 4A. AMINO ACID SEQUENCE OF HIGH MOLECULAR WEIGHT PROTEIN 2

```
  1  MNKIYRLKFS KRLNALVAVS ELARGCDHST EKGSEKPARM KVRHLALKPL
 51  SAMLLSLGVT SIPQSVLASG LQGMDVVHGT ATMQVDGNKT IIRNSVDAII
101  NWKQFNIDQN EMVQFLQENN NSAVFNRVTS NQISQLKGIL DSNGQVFLIN
151  PNGITIGKDA IINTNGFTAS TLDISNENIK ARNFTFEQTK DKALAEIVNH
201  GLITVGKDGS VNLIGGKVKN EGVISVNGGS ISLLAGQKIT ISDIINPTIT
251  YSIAAPENEA VNLGDIFAKG GNINVRAATI RNQGKLSADS VSKDKSGNIV
301  LSAKEGEAEI GGVISAQNQQ AKGGKLMITG DKVTLKTGAV IDLSGKEGGE
351  TYLGGDERGE GKNGIQLAKK TSLEKGSTIN VSGKEKGGRA IVWGDIALID
401  GNINAQSGD  IAKTGGFVET SGHDLFIKDN AIVDAKEWLL DFDNVSINAE
451  DPLRNNTGIN DEFPTGTGEA SDPKKNSELK TTLTNTTISN YLKNAWTMNI
501  TASRKLTVNS SINIGSNSHL ILHSKGQRGG GVQIDGDITS KGGNLTIYSG
551  GWVDVHKNIT LDQGFLNITA ASVAFEGGNN KARDAANAKI VAQGTVTITG
601  EGKDFRANNV SLNGTGKGLN IISSVNNLTH NLSGTINISG NITINQTTRK
651  NTSYWQTSHD SHWNVSALNL ETGANFTFIK YISSNSKGLT TQYRSSAGVN
701  FNGVNGNMSF NLKEGAKVNF KLKPNENMNT SKPLPIRFLA NITATGGGSV
```

FIG. 4B.

```
751   FFDIYANHSG RGAELKMSEI NISNGANFTL NSHVRGDDAF KINKDLTINA
801   TNSNFSLRQT KDDFYDGYAR NAINSTYNIS ILGGNVTLGG QNSSSSITGN
851   ITIEKAANVT LEANNAPNQQ NIRDRVIKLG SLLVNGSLSL TGENADIKGN
901   LTISESATFK GKTRDTLNIT GNFTNNGTAE INITQGVVKL GNVTNDGDLN
951   ITTHAKRNQR SIIGGDIINK KGSLNITDSN NDAEIQIGGN ISQKEGNLTI
1001  SSDKINITKQ ITIKKGIDGE DSSSDATSNA NLTIKTKELK LTEDLSISGF
1051  NKAEITAKDG RDLTIGNSND GNSGAEAKTV TFNNVKDSKI SADGHNVTLN
1101  SKVKTSSSNG GRESNSDNDT GLTITAKNVE VNKDITSLKT VNITASEKVT
1151  TTAGSTINAT NGKASITTKT GDISGTISGN TVSVSATVDL TTKSGSKIEA
1201  KSGEANVTSA TGTIGGTISG NTVNVTANAG DLTVGNGAEI NATEGAATLT
1251  ATGNTLTTEA GSSITSTKGQ VDLLAQNGSI AGSINAANVT LNTTGTLTTV
1301  AGSDIKATSG TLVINAKDAK LNGDASGDST EVNAVNASGS GSVTAATSSS
1351  VNITGDLNTV NGLNIISKDG RNTVRLRGKE IEVKYIQPGV ASVEEVIEAK
1401  RVLEKVKDLS DEERETLAKL GVSAVRFVEP NNTITVNTQN EFTRPSSQV
1451  IISEGKACFS SGNGARVCTN VADDGQP
```

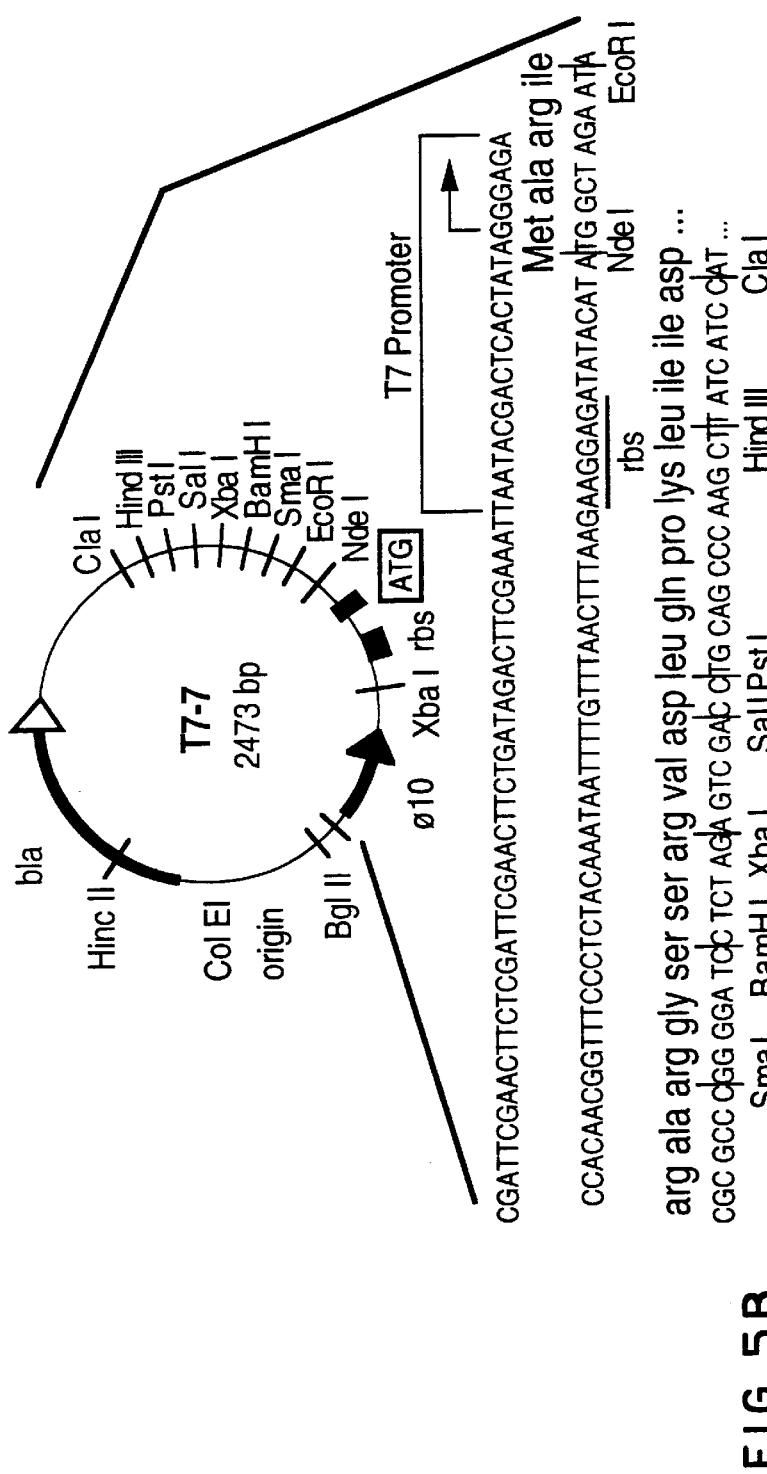

FIG. 5B.

(A) Partial restriction maps of representative HMW1 and HMW2 recombinant phage and of HMW1 plasmid subclones. The shaded boxes indicate the locations of the structural genes. In the recombinant phage, transcription proceeds from left to right for the HMW1 gene and from right to left for the HMW2 gene. The methods used for construction of the plasmids shown are described in the text. (B) Restriction map of the T7 expression vector pT7-7. This vector contains the T7 RNA polymerase promoter φ10, a ribosome - binding site (rbs), and the translational start site for the T7 gene 10 protein upstream from a multiple cloning site (37).

FIG. 6A.

```
  1  ACAGGCGTTCT CTTAATACTA GTACAAACCC ACAATAAAAT ATGACAAACA
 51  ACAATTACAA CACCTTTTTT GCAGTCTATA TGCAAATATT TTAAAAAATA
101  GTATAAATCC GCCATATAAA ATGGTATAAT CTTTCATCTT TCATCTTTCA
151  TCTTTCATCT TTCATCTTTC ATCTTTCATC TTTCATCTTT CATCTTTCAT
201  CTTTCATCTT TCATCTTTCA TCTTTCATCT TTCATCTTTC ACATGAAATG
251  ATGAACCGAG GGAAGGGAGG GAGGGGCAAG AATGAAGAGG GAGCTGAACG
301  AACGCAAATG ATAAAGTAAT TTAATTGTTC AACTAACCTT AGGAGAAAAT
351  ATGAACAAGA TATATCGTCT CAAATTCAGC AAACGCCTGA ATGCTTTGGT
401  TGCTGTGTCT GAATTGGCAC GGGGTTGTGA CCATTCCACA GAAAAAGGCA
451  GCGAAAAACC TGCTCGCATG AAAGTGCGTC ACTTAGCGTT AAAGCCACTT
501  TCCGCTATGT TACTATCTTT AGGTGTAACA TCTATTCCAC AATCTGTTTT
551  AGCAAGCGGC TTACAAGGAA TGGATGTAGT ACACGGCACA GCCACTATGC
601  AAGTAGATGG TAATAAAACC ATTATCCGCA ACAGTGTTGA CGCTATCATT
651  AATTGGAAAC AATTTAACAT CGACCAAAAT GAAATGGTGC AGTTTTACA
701  AGAAAACAAC AACTCCGCCG TATTCAACCG TGTTACATCT AACCAAATCT
751  CCCAATTAAA AGGGATTTTA GATTCTAACG GACAAGTCTT TTTAATCAAC
```

FIG. 6B.

```
 801  CCAAATGGTA  TCACAATAGG  TAAAGACGCA  ATTATTAACA  CTAATGGCTT
 851  TACGGCTTCT  ACGCTAGACA  TTTCTAACGA  AAACATCAAG  GCGCGTAATT
 901  TCACCTTCGA  GCAAACCAAA  GATAAAGCGC  TCGCTGAAAT  TGTGAATCAC
 951  GGTTTAATTA  CTGTCGGTAA  AGACGGCAGT  GTAAATCTTA  TTGGTGGCAA
1001  AGTGAAAAAC  GAGGGTGTGA  TTAGCGTAAA  TGGTGGCAGC  ATTTCTTTAC
1051  TCGCAGGGCA  AAAAATCACC  ATCAGCGATA  TAATAAACCC  AACCATTACT
1101  TACAGCATTG  CCGCGCCTGA  AAATGAAGCG  GTCAATCTGG  GCGATATTTT
1151  TGCCAAAGGC  GGTAACATTA  ATGTCCGTGC  TGCCACTATT  CGAAACCAAG
1251  CTTTCCGCCA  AAGAGGGTGA  AGCGGAAATT  GGCGGTGTAA  TTTCCGCTCA
1301  AAATCAGCAA  GCTAAAGGCG  GCAAGCTGAT  GATTACAGGC  GATAAAGTCA
1351  CATTAAAAAC  AGGTGCAGTT  ATCGACCTTT  CAGGTAAAGA  AGGGGAGAA
1401  ACTTACCTTG  GCGGTGACGA  GCGCGGGCGAA  GGTAAAAACG  GCATTCAATT
1451  AGCAAAGAAA  ACCTCTTTAG  AAAAAGGCTC  AACCATCAAT  GTATCAGGCA
1501  AAGAAAAAGG  CGGACGCGCT  ATTGTGTGGG  GCGATATTGC  GTTAATTGAC
1551  GGCAATATTA  ACGCTCAAGG  TAGTGGTGAT  ATCGCTAAAA  CCGGTGGTTT
1601  TGTGGAGACG  TCGGGGCATG  ATTTATTCAT  CAAAGACAAT  GCAATTGTTG
```

FIG. 6C.

```
1651  ACGCCAAAGA  GTGGTTGTTA  GACCCGGATA  ATGTATCTAT  TAATGCAGAA
1701  ACAGCAGGAC  GCAGCAATAC  TTCAGAAGAC  GATGAATACA  CGGGATCCGG
1751  GAATAGTGCC  AGCACCCCAA  AACGAAACAA  AGAAAAGACA  ACATTAACAA
1801  ACACAACTCT  TGAGAGTATA  CTAAAAAAAG  GTACCTTTGT  TAACATCACT
1851  GCTAATCAAC  GCATCTATGT  CAATAGCTCC  ATTAATTTAT  CCAATGGCAG
1901  CTTAACTCTT  TGGAGTGAGG  GTCGGAGCGG  TGGCGGCGTT  GAGATTAACA
1951  ACGATATTAC  CACCGGTGAT  GATACCAGAG  GTGCAAACTT  AACAATTTAC
2001  TCAGGCGGCT  GGGTTGATGT  TCATAAAAAT  ATCTCACTCG  GGGCGCAAGG
2051  TAACATAAAC  ATTACAGCTA  AACAAGATAT  CGCCTTTGAG  AAAGGAAGCA
2101  ACCAAGTCAT  TACAGGTCAA  GGGACTATTA  CCTCAGGCAA  TCAAAAGGT
2151  TTTAGATTA   ATAATGTCTC  TCTAAACGGC  ACTGGCAGCG  GACTGCAATT
2201  CACCACTAAA  AGAACCAATA  AATACGCTAT  CACAAATAAA  TTTGAAGGA
2251  CTTTAAATAT  TTCAGGGAAA  GTGAACATCT  CAATGGTTTT  ACCTAAAAAT
2301  GAAAGTGGAT  ATGATAAATT  CAAAGGACGC  ACTTACTGGA  ATTTAACCTC
2351  GAAAGTGGAT  ATGATAAATT  CAAAGGACGC  CCTCACTATT  GACTCCAGAG
2401  GAAGCGATAG  TGCAGGCACA  CTTACCCAGC  CTTATAATTT  AAACGGTATA
2451  TCATTCAACA  AAGACACTAC  CTTTAATGTT  GAACGAAATG  CAAGAGTCAA
```

FIG. 6D.

```
2501  CTTTGACATC  AAGGCACCAA  TAGGGATAAA  TAAGTATTCT  AGTTTGAATT
2551  ACGCATCATT  TAATGGAAAC  ATTTCAGTTT  CGGGAGGGGG  GAGTGTTGAT
2601  TTCACACTTC  TCGCCTCATC  CTCTAACGTC  CAAACCCCCG  GTGTAGTTAT
2651  AAATTCTAAA  TACTTTAATG  TTTCAACAGG  GTCAAGTTTA  AGATTTAAAA
2701  CTTCAGGCTC  AACAAAAACT  GGCTTCTCAA  TAGAGAAAGA  TTTAACTTTA
2751  AATGCCACCG  GAGGCAACAT  AACACTTTTG  CAAGTTGAAG  GCACCGATGG
2801  AATGATTGGT  AAAGGCATTG  TAGCCAAAAA  AAACATAACC  TTTGAAGGAG
2851  GTAAGATGAG  GTTTGGCTCC  AGGAAAGCCG  TAACAGAAAT  CGAAGGCAAT
2901  GTTACTATCA  ATAACAACGC  TAACGTCACT  CTTATCGGTT  CGGATTTTGA
2951  CAACCATCAA  AAACCTTTAA  CTATTAAAAA  AGATGTCATC  ATTAATAGCG
3001  GCAACCTTAC  CGCTGGAGGC  AATATTGTCA  ATATAGCCGG  AAATCTTACC
3051  GTTGAAAGTA  ACGCTAATTT  CAAAGCTATC  ACAAATTTCA  CTTTTAATGT
3101  AGGCGGCTTG  TTTGACAACA  AAGGCAATTC  AAATATTTCC  ATTGCCAAAG
3151  GAGGGGCTCG  CTTTAAAGAC  ATTGATAATT  CCAAGAATTT  AAGCATCACC
3201  ACCAACTCCA  GCTCCACTTA  CCGCACTATT  ATAAGCGGCA  ATATAACCAA
3251  TAAAAACGGT  GATTTAAATA  TTACGAACGA  AGGTAGTGAT  ACTGAAATGC
```

FIG. 6E.

```
3301  AAATTGGCGG  CGATGTCTCG  CAAAAAGAAG  GTAATCTCAC  GATTCTTCT
3351  GACAAAATCA  ATATTACCAA  ACAGATAACA  ATCAAGGCAG  GTGTTGATGG
3401  GGAGAATTCC  GATTCAGACG  CGACAAACAA  TGCCAATCTA  ACCATTAAAA
3451  CCAAAGAATT  GAAATTAACG  CAAGACCTAA  ATATTTCAGG  TTTCAATAAA
3501  GCAGAGATTA  CAGCTAAAGA  TGGTAGTGAT  TTAACTATTG  GTAACACCAA
3551  TAGTGCTGAT  GGTACTAATG  CCAAAAAAGT  AACCTTTAAC  CAGGTAAAG
3601  ATTCAAAAAT  CTCTGCTGAC  GGTCACAAGG  TGACACTACA  CAGCAAAGTG
3651  GAAACATCCG  GTAGTAATAA  CAACACTGAA  GATAGCAGTG  ACAATAATGC
3701  CGGCTTAACT  ATCGATGCAA  AAAATGTAAC  AGTAAACAAC  AATATTACTT
3751  CTCACAAAGC  AGTGAGCATC  TCTGCGACAA  GTGGAGAAAT  TACCACTAAA
3801  ACAGGTACAA  CCATTAACGC  AACCACTGGT  AACGTGGAGA  TAACCGCTCA
3851  AACAGGTAGT  ATCCTAGGTG  GAATTGAGTC  CAGCTCTGGC  TCTGTAACAC
3901  TTACTGCAAC  CGAGGGCGCT  CTTGCTGTAA  GCAATATTTC  GGGCAACACC
3951  GTTACTGTTA  CTGCAAATAG  CGGTGCATTA  ACCACTTTGG  CAGGCTCTAC
4001  AATTAAAGGA  ACCGAGAGTG  TAACCACTTC  AAGTCAATCA  GGCGATATCG
4051  GCGGTACGAT  TTCTGGTGGC  ACAGTAGAGG  TTAAAGCAAC  CGAAAGTTTA
```

FIG. 6F.

```
4101 ACCACTCAAT CCAATTCAAA AATTAAAGCA ACAACAGGCG AGGCTAACGT
4151 AACAAGTGCA ACAGGTACAA TTGGTGGTAC GATTTCCGGT AATACGGTAA
4201 ATGTTACGGC AAACGCTGGC GATTTAACAG TTGGGAATGG CGCAGAAATT
4251 AATGCGACAG AAGGAGCTGC AACCTTAACT ACATCATCGG GCAAATTAAC
4301 TACCGAAGCT AGTTCACACA TTACTTCAGC CAAGGGTCAG GTAAATCTTT
4351 CAGCTCAGGA TGGTAGCGTT GCAGGAAGTA TTAATGCCGC CAATGTGACA
4401 CTAAATACTA CAGGCACTTT AACTACCGTG AAGGGTTCAA ACATTAATGC
4451 AACCAGCGGT ACCTTGGTTA TTAACGCAAA AGACGCTGAG CTAAATGGCG
4501 CAGCATTGGG TAACCACACA GTGGTAAATG CAACCAACGC AAATGGCTCC
4551 GGCAGCGTAA TCGCGACAAC CTCAAGCAGA GTGAACATCA CTGGGGATTT
4601 AATCACAATA AATGGATTAA ATATCATTTC AAAAAACGGT ATAAACACCG
4651 TACTGTTAAA AGGCGTTAAA ATTGATGTGA AATACATTCA ACCGGGTATA
4701 GCAAGCGTAG ATGAAGTAAT TGAAGCGAAA CGCATCCTTG AGAAGGTAAA
4751 AGATTTATCT GATGAAGAAA GAGAAGCGTT AGCTAAACTT GGCGTAAGTG
4801 CTGTACGTTT TATTGAGCCA AATAATACAA TTACAGTCGA TACACAAAAT
4851 GAATTTGCAA CCAGACCATT AAGTCGAATA GTGATTTCTG AAGGCAGGGC
4901 GTGTTCTCA AACAGTGATG GCGCGACGGT GTGCGTTAAT ATCGCTGATA
```

FIG. 6G.

```
4951  ACGGGCGGTA  GCGGTCAGTA  ATTGACAAGG  TAGATTTCAT  CCTGCAATGA
5001  AGTCATTTTA  TTTTCGTATT  ATTTACTGTG  TGGGTTAAAG  TTCAGTACGG
5051  GCTTTACCCA  TCTTGTAAAA  AATTACGGAG  AATACAATAA  AGTATTTTTA
5101  ACAGGTTATT  ATTATGAAAA  ATATAAAAAG  CAGATTAAAA  CTCAGTGCAA
5151  TATCAGTATT  GCTTGGCCTG  GCTTCTTCAT  CATTGTATGC  AGAAGAAGCG
5201  TTTTTAGTAA  AAGGCTTTCA  GTTATCTGGT  GCACTTGAAA  CTTTAAGTGA
5251  AGACGCCCAA  CTGTCTGTAG  CAAAATCTTT  ATCTAAATAC  CAAGGCTCGC
5301  AAACTTTAAC  AAACCTAAAA  ACAGCACAGC  TTGAATTACA  GGCTGTGCTA
5351  GATAAGATTG  AGCCAAATAA  GTTTGATGTG  ATATTGCCAC  AACAAACCAT
5401  TACGGATGGC  AATATTATGT  TTGAGCTAGT  CTCGAAATCA  GCCGCAGAAA
5451  GCCAAGTTTT  TTATAAGGCG  AGCCAGGGTT  ATAGTGAAGA  AATATCGCT
5501  CGTAGCCTGC  CATCTTTGAA  ACAAGGAAAA  GTGTATGAAG  ATGGTCGTCA
5551  GTGGTTCGAT  TTGCGTGAAT  TCAATATGGC  AAAAGAAAAT  CCACTTAAAG
5601  TCACTCGCGT  GCATTACGAG  TTAAACCCTA  AAAACAAAAC  CTCTGATTTG
5651  GTAGTTGCAG  GTTTTCGCC  TTTTGGCAAA  ACGGTAGCT  TTGTTTCCTA
5701  TGATAATTTC  GGCGCAAGGG  AGTTTAACTA  TCAACGTGTA  AGTCTAGGTT
```

FIG. 6H.

```
5751  TTGTAAATGC CAATTTGACC GGACATGATG ATGTATTAAA TCTAAACGCA
5801  TTGACCAATG TAAAAGCACC ATCAAAATCT TATGCGGTAG GCATAGGATA
5851  TACTTATCCG TTTTATGATA AACACCAATC CTTAAGTCTT TATACCAGCA
5901  TGAGTTATGC TGATTCTAAT GATATCGACG GCTTACCAAG TGCGATTAAT
5951  CGTAAATTAT CAAAAGGTCA ATCTATCTCT GCGAATCTGA AATGGAGTTA
6001  TTATCTCCCG ACATTTAACC TTGGAATGGA AGACCAGTTT AAAATTAATT
6051  TAGGCTACAA CTACCGCCAT ATTAATCAAA CATCCGAGTT AAACACCCTG
6101  GGTGCAACGA AGAAAAAATT TGCAGTATCA GGCGTAAGTG CAGGCATTGA
6151  TGGACATATC CAATTTACCC CTAAAACAAT CTTTAATATT GATTAACTC
6201  ATCATTATTA CGCGAGTAAA TTACCAGGCT CTTTTGGAAT GGAGCGCATT
6251  GGCGAAACAT TTAATCGCAG CTATCACATT AGCACAGCCA GTTTAGGGTT
6301  GAGTCAAGAG TTTGCTCAAG GTTGGCATTT TAGCAGTCAA TTATCGGGTC
6351  AGTTACTCT ACAAGATATA AGTAGCATAG ATTTATTCTC TGTAACAGGT
6401  ACTTATGCG TCAGAGGCTT TAAATACGGC GGTGCAAGTG GTGAGCGCGG
6451  TCTTGTATGG CGTAATGAAT TAAGTATGCC AAAATACACC CGCTTTCAAA
6501  TCAGCCCTTA TGCGTTTTAT GATGCAGGTC AGTCCGTTA TAATAGCGAA
6551  AATGCTAAAA CTTACGGCGA AGATATGCAC ACGGTATCCT CTGCGGGTTT
```

FIG. 6I.

```
6601  AGGCATTAAA ACCTCTCCTA CACAAAACTT AAGCTTAGAT GCTTTTGTTG
6651  CTCGTCGCTT TGCAAATGCC AATAGTGACA ATTTGAATGG CAACAAAAAA
6701  CGCACAAGCT CACCTACAAC CTTCTGGGGT AGATTAACAT TCAGTTTCTA
6751  ACCCTGAAAT TTAATCAACT GGTAAGCGTT CCGCCTACCA GTTTATAACT
6801  ATATGCTTTA CCCGCCAATT TACAGTCTAT ACGCAACCCT GTTTTCATCC
6851  TTATATATCA AACAAACTAA GCAAACCAAG CAAACCAAGC AAACCAAGCA
6901  AACCAAGCAA ACCAAGCAAA CCAAGCAAAC CAAGCAAACC AAGCAAACCA
6951  AGCAAACCAA GCAAACCAAG CAAACCAAGC AAACCAAGCA ATGCTAAAAA
7001  ACAATTTATA TGATAAACTA AAACATACTC CATACCATGG CAATACAAGG
7051  GATTTAATAA TATGACAAAA GAAAATTTAC AAAGTGTTCC ACAAAATACG
7101  ACCGCTTCAC TTGTAGAATC AAACAACGAC CAAACTTCCC TGCAAATACT
7151  TAAACAACCA CCCAAACCCA ACCTATTACG CCTGAACAA CATGTCGCCA
7201  AAAAAGATTA TGAGCTTGCT TGCCGCGAAT TAATGGCGAT TTTGGAAAAA
7251  ATGGACGCTA ATTTTGGAGG CGTTCACGAT ATTGAATTTG ACGCACCTGC
7301  TCAGCTGGCA TATCTACCCG AAAAACTACT AATTCATTTT GCCACTCGTC
7351  TCGCTAATGC AATTACAACA CTCTTTTCCG ACCCGAATT GGCAATTTCC
```

FIG. 6J.

```
7401 GAAGAAGGGG CATTAAAGAT GATTAGCCTG CAACGCTGGT TGACGCTGAT
7451 TTTGCCTCT TCCCCCTACG TTAACGCAGA CCATATTCTC AATAAATATA
7501 ATATCAACCC AGATTCCGAA GGTGGCTTTC ATTTAGCAAC AGACAACTCT
7551 TCTATTGCTA AATTCTGTAT TTTTTACTTA CCCGAATCCA ATGTCAATAT
7601 GAGTTTAGAT GCGTTATGGG CAGGGAATCA ACAACTTTGT GCTTCATTGT
7651 GTTTTGCGTT GCAGTCTTCA CGTTTTATTG GTACTGCATC TGCGTTTCAT
7701 AAAAGAGCGG TGGTTTTACA GTGGTTTCCT AAAAAACTCG CCGAAATTGC
7751 TAATTTAGAT GAATTGCCTG CAAATATCCT TCATGATGTA TATATGCACT
7801 GCAGTTATGA TTTAGCAAAA AACAAGCACG ATGTTAAGCG TCCATTAAAC
7851 GAACTTGTCC GCAAGCATAT CCTCACGCAA GGATGGCAAG ACCGCTACCT
7901 TTACACCTTA GGTAAAAAGG ACGGCAAACC TGTGATGATG GTACTGCTTG
7951 AACATTTAA TTCGGGACAT CTATTTAGTC GCACGCATTC AACTTCAATG
8001 ATTGCTGCTC GAGAAAAATT GGCTTAGGCC ATGAGGGCGT
8051 TGATAACATA GGTCGAGAAG TGTTTGACGA GTTCTTTGAA ATCAGTAGCA
8101 ATAATATAAT GGAGAGACTG TTTTTTATCC GTAAACAGTG CGAAACTTTC
8151 CAACCCGCAG TGTTCTATAT GCCAAGCATT GGCATGGATA TTACCACGAT
```

FIG. 6K.

```
8201  TTTGTGAGC AACACTCGGC TTGCCCCTAT TCAAGCTGTA GCCTTGGGTC
8251  ATCCTGCCAC TACGCATTCT GAATTTATTG ATTATGTCAT CGTAGAAGAT
8301  GATTATGTGG GCAGTGAAGA TTGTTTAGC  GAAACCCTTT TACGCTTACC
8351  CAAAGATGCC CTACCTTATG TACCATCTGC ACTCGCCCCA CAAAAAGTGG
8401  ATTATGTACT CAGGGAAAAC CCTGAAGTAG TCAATATCGG TATTGCCGCT
8451  ACCACAATGA AATTAAACCC TGAATTTTTG CTAACATTGC AAGAAATCAG
8501  AGATAAAGCT AAAGTCAAAA TACATTTTCA TTTCGCACTT GGACAATCAA
8551  CAGGCTTGAC ACACCCTTAT GTCAAATGGT TTATCGAAAG CTATTTAGGT
8601  GACGATGCCA CTGCACATCC CCACGCACCT TATCACGATT ATCTGGCAAT
8651  ATTGCGTGAT TGCGATATGC TACTAAATCC GTTTCCTTTC GGTAATACTA
8701  ACGGCATAAT TGATGAACA ACATTAGGTT TAGTTGGTGT ATGCAAAACG
8751  GGGGATGAAG TACATGAACA TATTGATGAA GGTCTGTTTA AACGCTTAGG
8801  ACTACCAGAA TGGCTGATAG CCGACACACG AGAAACATAT ATTGAATGTG
8851  CTTTGCGTCT AGCAGAAAAC CATCAAGAAC GCCTTGAACT CCGTCGTTAC
8901  ATCATAGAAA ACAACGCTT  ACAAAAGCTT TTTACAGGCG ACCCTCGTCC
8951  ATTGGGCAAA ATACTGCTTA AGAAAACAAA TGAATGGAAG CGGAAGCACT
9001  TGAGTAAAAA ATAACGGTTT TTTAAAGTAA AAGTGCGGTT AATTTTCAAA
```

FIG. 6L.

| | | | | | |
|---|---|---|---|---|---|
| 9051 | GCGTTTTAAA | AACCTCTCAA | AAATCAACCG | CACTTTTATC | TTTATAACGC |
| 9101 | TCCCGGCGGC | TGACAGTTTA | TCTCTTTCTT | AAAATACCCA | TAAAATTGTG |
| 9151 | GCAATAGTTG | GGTAATCAAA | TTCAATTGTT | GATACGGCAA | ACTAAAGACG |
| 9201 | GCGCGTTCTT | CGGCAGTCAT | C | | |

FIG. 7A.

```
  1 CGCCACTTCA ATTTTGGATT GTTGAAATTC AACTAACCAA AAAGTGCGGT
 51 TAAAATCTGT GGAGAAAATA GGTTGTAGTG AAGAACGAGG TAATTGTTCA
101 AAAGGATAAA GCTCTCTTAA TTGGGCATTG GTTGGCGTTT CTTTTTCGGT
151 TAATAGTAAA TTATATTCTG GACGACTATG CAATCCACCA ACAACTTTAC
201 CGTTGGTTTT AAGCGTTAAT GTAAGTTCTT GCTCTTCTTG GCGAATACGT
251 AATCCCATTT TTTGTTTAGC AAGAAAATGA TCGGGATAAT CATAATAGGT
301 GTTGCCCAAA AATAAATTTT GATGTTCTAA AATCATAAAT TTTGCAAGAT
351 ATTGTGGCAA TTCAATACCT ATTTGTGGCG AAATCGCCAA TTTTAATTCA
401 ATTTCTTGTA GCATAATATT TCCCACTCAA ATCAACTGGT TAAATATACA
451 AGATAATAAA AATAAATCAA GATTTTTGTG ATGACAAACA ACAATTACAA
501 CACCTTTTTT GCAGTCTATA TGCAAATATT TTAAAAAAAT AGTATAAATC
551 CGCCATATAA AATGGTATAA TCTTTCATCT CTTTCATCTT ATCTTTCATC
601 TTTCATCTTT CATCTTTCAT ATCTTTCATC TTTCATCTTT TCATTTCATCT
651 TTCATCTTTC ATCTTTCATC TTTCATCTTT CACATGAAAT GATGAACCGA
701 GGGAAGGGAG GGAGGGGCAA GAATGAAGAG GGAGCTGAAC GAACGCAAAT
751 GATAAAGTAA TTTAATTGTT CAACTAACCT TAGGAGAAAA TATGAACAAG
```

FIG. 7B.

```
801  ATATATCGTC TCAAATTCAG CAAACGCCTG AATGCTTTGG TTGCTGTGTC
851  TGAATTGGCA CGGGGTTGTG ACCATTCCAC AGAAAAAGGC AGCGAAAAAC
901  CTGCTCGCAT GAAAGTGCGT CACTTAGCGT TAAAGCCACT TTCCGCTATG
951  TTACTATCTT TAGGTGTAAC ATCTATTCCA CAATCTGTTT TAGCAAGCGG
1001 CAATTTAACA TCGACCAAAA TGAAATGGTG CAGTTTTTAC AAGAAAACAA
1051 GTAATAAAAC CATTATCCGC AACAGTGTTG ACGCTATCAT TAATTGGAAA
1101 CAATTTAACA TCGACCAAAA TGAAATGGTG CAGTTTTTAC AAGAAAACAA
1151 CAACTCCGCC GTATTCAACC GTGTTACATC TAACCAAATC TCCCAATTAA
1201 AAGGGATTTT AGATTCTAAC GGACAAGTCT TTTTAATCAA CCCAAATGGT
1251 ATCACAATAG GTAAAGACGC AATTATTAAC ACTAATGGCT TTACGGCTTC
1301 TACGCTAGAC ATTTCTAACG AAAACATCAA GGCGCGTAAT TTCACCTTCG
1351 AGCAAACCAA AGATAAAGCG CTCGCTGAAA TTGTGAATCA CGGTTTAATT
1401 ACTGTCGGTA AAGACGGCAG TGTAAATCTT ATTGGTGGCA AAGTGAAAAA
1451 CGAGGGTGTG ATTAGCGTAA ATGGTGGCAG CATTTCTTTA CTCGCAGGGC
1501 AAAAAATCAC CATCAGCGAT ATAATAAACC CAACCATTAC TTACAGCATT
1551 GCCGCGCCTG AAAATGAAGC GGTCAATCTG TTGCCAAAGG
```

FIG. 7C.

```
1601  CGGTAACATT  AATGTCCGTG  CTGCCACTAT  TCGAAACCAA  GGTAAACTTT
1651  CTGCTGATTC  TGTAAGCAAA  GATAAAGCG   GCAATATTGT  TCTTTCCGCC
1701  AAAGAGGGTG  AAGCGGAAAT  TGGCGGTGTA  ATTTCCGCTC  AAAATCAGCA
1751  AGCTAAAGGC  GGCAAGCTGA  TGATTACAGG  CGATAAAGTC  ACATTAAAAA
1801  CAGGTGCAGT  TATCGACCTT  TCAGGTAAAG  AAGGGGGAGA  AACTTACCTT
1851  GGCGGTGACG  AGCGCGGCGA  AGGTAAAAAC  GGCATTCAAT  TAGCAAAGAA
1901  AACCTCTTTA  GAAAAAGGCT  CAACCATCAA  TGTATCAGGC  AAAGAAAAAG
1951  GCGGACGCGC  TATTGTGTGG  GGCGATATTG  CGTTAATTGA  CGGCAATATT
2001  AACGCTCAAG  GTAGTGGTGA  TATCGCTAAA  ACCGGTGGTT  TTGTGGAGAC
2051  ATCGGGGCAT  TATTTATCCA  TTGACAGCAA  TGCAATTGTT  AAAACAAAAG
2101  AGTGGTTGCT  AGACCCTGAT  GATGTAACAA  TTGAAGCCGA  AGACCCCTT
2151  CGCAATAATA  CCGGTATAAA  TGATGAATTC  CCAACAGGCA  CCGGTGAAGC
2201  AAGCGACCCT  AAAAAAAATA  GCGAACTCAA  AACAACGCTA  ACCAATACAA
2251  CTATTTCAAA  TTATCTGAAA  AACGCCTGGA  CAATGAATAT  AACGGCATCA
2301  AGAAAACTTA  CCGTTAATAG  CTCAATCAAC  ATCGGAAGCA  ACTCCCACTT
2351  AATTCTCCAT  AGTAAAGGTC  AGCGTGGCGG  AGGCGTTCAG  ATTGATGGAG
2401  ATATTACTTC  TAAAGGCGGA  AATTTAACCA  TTTATTCTGG  CGGATGGGTT
```

FIG. 7D.

```
2451  GATGTTCATA  AAAATATTAC  GCTTGATCAG  GGTTTTTTAA  ATATTACCGC
2501  CGCTTCCGTA  GCTTTTGAAG  GTGGAAATAA  CAAAGCACGC  GACGCGGCAA
2551  ATGCTAAAAT  TGTCGCCCAG  GGCACTGTAA  CCATTACAGG  AGAGGAAAA
2601  GATTTCAGGG  CTAACAACGT  ATCTTTAAAC  GGAACGGGTA  AAGGTCTGAA
2651  TATCATTTCA  TCAGTGAATA  ATTTAACCCA  CAATCTTAGT  GGCACAATTA
2701  ACATATCTGG  GAATATAACA  ATTAACCAAA  CTACGAGAAA  GAACACCTCG
2751  TATTGGCAAA  CCAGCCATGA  TTCGCACTGG  AACGTCAGTG  CTCTTAATCT
2801  AGAGACAGGC  GCAAATTTTA  CCTTTATTAA  ATACATTTCA  AGCAATAGCA
2851  AAGGCTTAAC  AACACAGTAT  AGAAGCTCTG  CAGGGGTGAA  TTTTAACGGC
2901  GTAAATGGCA  ACATGTCATT  CAATCTCAAA  GAAGGAGCGA  AAGTTAATTT
2951  CAAATTAAAA  CCAAACGAGA  ACATGAACAC  AAGCAAACCT  TTACCAATTC
3001  GGTTTTTAGC  CAATATCACA  GCCACTGGTG  GGGCTCTGT  TTTTTTTGAT
3051  ATATATGCCA  ACCATTCTGG  CAGAGGGGCT  GAGTTAAAAA  TGAGTGAAAT
3101  TAATATCTCT  AACGGCGCTA  ATTTTACCTT  AAATTCCCAT  GTTCGCGGCG
3151  ATGACGCTTT  TAAAATCAAC  AAAGACTTAA  CCATAAATGC  AACCAATTCA
3201  AATTTCAGCC  TCAGACAGAC  GAAAGATGAT  TTTTATGACG  GGTACGCCACG
```

FIG. 7E.

```
3251  CAATGCCATC AATTCAACCT ACAACATATC CATTCTGGGC GGTAATGTCA
3301  CCCTTGGTGG ACAAAACTCA AGCAGCAGCA TTACGGGGAA TATTACTATC
3351  GAGAAAGCAG CAAATGTTAC GCTAGAAGCC AATAACGCCC CTAATCAGCA
3401  AAACATAAGG GATAGAGTTA TAAAACTTGG CAGCTTGCTC GTTAATGGGA
3451  GTTTAAGTTT AACTGGCGAA AATGCAGATA TTAAAGGCAA TCTCACTATT
3501  TCAGAAAGCG CCACTTTTAA AGGAAAGACT AGAGATACCC TAAATATCAC
3551  CGGCAATTTT ACCAATAATG GCACTGCCGA AATTAATATA ACACAAGGAG
3601  TGGTAAAACT TGGCAATGTT ACCAATGATG GTGATTTAAA CATTACCACT
3651  CACGCTAAAC GCAACCAAAG AAGCATCATC GGCGGAGATA TAATCAACAA
3701  AAAAGGAAGC TTAAATATTA CAGACAGTAA TAATGATGCT GAAATCCAAA
3751  TTGGGCGGCAA TATCTCGCAA AAAGAAGGCA ACCTCACGAT TTCTTCCGAT
3801  AAAATTAATA TCACCAAACA GATAACAATC AAAAAGGGTA TTGATGGAGA
3851  GGACTCTAGT TCAGATGCGA CAAGTAATGC CAACCTAACT ATTAAAACCA
3901  AAGAATTGAA ATTGACAGAA GACCTAAGTA TTTCAGGTTT CAATAAAGCA
3951  GAGATTACAG TAGAGATTTA ACTATTGGCA ACAGTAATGA
4001  CGGTAACAGC GGTGCCGAAG CCAAAACAGT AACTTTTAAC AATGTTAAAG
```

FIG. 7F.

```
4051  ATTCAAAAAT CTCTGCTGAC GGTCACAATG TGACACTAAA TAGCAAAGTG
4101  AAAACATCTA GCAGCAATGG CGGACGTGAA AGCAATAGCG ACAACGATAC
4151  CGGCTTAACT ATTACTGCAA AAAATGTAGA AGTAAACAAA GATATTACTT
4201  CTCTCAAAAC AGTAAATATC ACCGCGTCGG AAAAGGTTAC CACCACAGCA
4251  GGCTCGACCA TTAACGCAAC AAATGGCAAA GCAAGTATTA CAACCAAAAC
4301  AGGTGATATC AGCGGTACGA TTTCCGGTAA CACGGTAAGT GTTAGCGCGA
4351  CTGGTGATTT AACCACTAAA TCCGGCTCAA AAATTGAAGC GAAATCGGGT
4401  GAGGCTAATG TAACAAGTGC AACAGGTACA ATTGGCGGTA CAATTTCCGG
4451  TAATACGGTA AATGTTACGG CAAACGCTGG CGATTTAACA GTTGGAATG
4501  GCGCAGAAAT TAATGCGACA GAAGGAGCTG CAACCTTAAC CGCAACAGGG
4551  AATACCTTGA CTACTGAAGC CGGTTCTAGC ATCACTTCAA CTAAGGGTCA
4601  GGTAGACCTC TTGGCTCAGA ATGGTAGCAT CGCAGGAAGC ATTAATGCTG
4651  CTAATGTGAC ATTAAATACT ACAGGCACCT TAACCACCGT GGCAGGCTCG
4701  GATATTAAAG CAACCAGCGG CACCTTGGTT ATTAACGCAA AAGATGCTAA
4751  GCTAAATGGT GATGCATCAG GTGATAGTAC AGAAGTGAAT GCAGTCAACG
4801  ACTGGGGATT TGGTAGTGTG ACTGCGGCAA CCTCAAGCAG TGTGAATATC
4851  ACTGGGGATT TAAACACAGT AAATGGGTTA AATATCATTT CGAAAGATGG
```

FIG. 7G.

```
4901  TAGAAACACT GTGCGCTTAA GAGGCAAGGA AATTGAGGTG AAATATATCC
4951  AGCCAGGTGT AGCAAGTGTA GAAGAAGTAA TTGAAGCGAA ACGCGTCCTT
5001  GAAAAAGTAA AAGATTTATC TGATGAAGAA AGAGAAACAT TAGCTAAACT
5051  TGGTGTAAGT GCTGTACGTT TTGTTGAGCC AAATAATACA ATTACAGTCA
5101  ATACACAAAA TGAATTTACA ACCAGACCGT CAAGTCAAGT GATAATTTCT
5151  GAAGGTAAGG CGTGTTCTC AAGTGGTAAT GGCGCACGAG TATGTACCAA
5201  TGTTGCTGAC GATGGACAGC CGTAGTCAGT AATTGACAAG GTAGATTTCA
5251  TCCTGCAATG AAGTCATTTT ATTTTCGTAT TATTTACTGT GTGGGTTAAA
5301  GTTCAGTACG GGCTTTACCC ATCTTGTAAA AAATTACGGA GAATACAATA
5351  AAGTATTTTT AACAGGTTAT TATTATGAAA AATATAAAAA GCAGATTAAA
5401  ACTCAGTGCA ATATCAGTAT TGCTTGGCCT GGCTTCTTCA TCATTGTATG
5451  CAGAAGAAGC GTTTTAGTA AAAGGCTTTC AGTTATCTGG TGCACTTGAA
5501  ACTTTAAGTG AAGACGCCCA ACTGTCTGTA GCAAAATCTT TATCTAAATA
5551  CCAAGGCTCG CAAACTTTAA CAAACCTAAA AACAGCACAG CTTGAATTAC
5601  AGCTGTGCT AGATAAGATT GAGCCAAATA AATTTGATGT GATATTGCCG
5651  CAACAAACCA TTACGGATGG CAATATCATG TTTGAGCTAG TCTCGAAATC
```

FIG. 7H.

```
5701  AGCCGCAGAA AGCCAAGTTT TTTATAAGGC GAGCCAGGGT TATAGTGAAG
5751  AAAATATCGC TCGTAGCCTG CCATCTTTGA AACAAGGAAA AGTGTATGAA
5801  GATGGTCGTC AGTGGTTCGA TTTGCCGTGA TTTAATATGG CAAAAGAAAA
5851  CCCGCTTAAG GTTACCCGTG TACATTACGA ACTAAACCCT AAAAACAAAA
5901  CCTCTAATTT GATAATTGCG GGCTTCTCGC CTTTTGGTAA AACGCGTAGC
5951  TTTATTTCTT ATGATAATTT CGGCGCGAGA GAGTTTAACT ACCAACGTGT
6001  AAGCTTGGGT TTTGTTAATG CCAATTTAAC TGGTCATGAT GATGTGTTAA
6151  TTATACCAGT ATGAGTTATG CTGATTCTAA TGATATCGAC GGCTTACCAA
6201  GTGCGATTAA TCGTAAATTA TCAAAAGGTC AATCTATCTC TGCGAATCTG
6251  AAATGGAGTT ATTATCTCCC AACATTTAAC CTTGGCATGG AAGACCAATT
6301  TAAAATTAAT TTAGGCTACA ACTACCGCCA TATTAATCAA ACCTCCGCGT
6351  TAAATCGCTT GGGTGAAACG AAGAAAAAAT TTGCAGTATC AGGGCGTAAGT
6401  GCAGGCATTG ATGGACATAT CCAATTTACC CCTAAAACAA TCTTTAATAT
6451  TGATTAACT CATCATTATT ACGCGAGTAA ATTACCAGGC TCTTTTGGAA
6501  TGGAGCGCAT TGGCGAAACA TTTAATCGCA GCTATCACAT TAGCACAGCC
6551  AGTTTAGGGT TGAGTCAAGA GTTGCTCAA GGTTGGCATT TTAGCAGTCA
6601  ATTATCAGGT CAATTTACTC TACAAGATAT TAGCAGTATA GATTATTCT
```

FIG. 7I.

```
6651  CTGTAACAGG  TACTTATGGC  GTCAGAGGCT  TTAAATACGG  CGGTGCAAGT
6701  GGTGAGCGCG  GTCTTGTATG  GCGTAATGAA  TTAAGTATGC  CAAAATACAC
6751  CCGCTTCCAA  ATCAGCCCTT  ATGCGTTTTA  TGATGCAGGT  CAGTTCCGTT
6801  ATAATAGCGA  AAATGCTAAA  ACTTACGGCG  AAGATATGCA  CACGGTATCC
6851  TCTGCGGGTT  TAGGCATTAA  AACCTCTCCT  ACACAAAACT  TAAGCCTAGA
6901  TGCTTTTGTT  GCTCGTCGCT  TTGCAAATGC  CAATAGTGAC  AATTTGAATG
6951  GCAACAAAAA  ACGCACAAGC  TCACCTACAA  CCTTCTGGGG  GAGATTAACA
7001  TTCAGTTTCT  AACCCTGAAA  TTTAATCAAC  TGGTAAGCGT  TCCGCCTACC
7051  AGTTTATAAC  TATATGCTTT  ACCCGCCAAT  TTACAGTCTA  TAGGCAACCC
7101  TGTTTTTACC  CTTATATATC  AAATAAACAA  GCTAAGCTGA  ATTTATATGA
7151  CCAAGCAAAC  TCAAGCAAGC  CAAGTAATAC  TAAAAAAACA  TTAATAATAT
7201  TAAACTAAAG  TATACTCCAT  GCCATGGCGA  TACAAGGGAT  GCTTTACTTG
7251  GACAAAAGAA  AATTGCAAA   ACGCTCCTCA  AGATGCGACC  ACAACCACGC
7301  CGGAATTAAG  CAACAATCAA  ACTCCCCTGC  GAATATTTAA  ATCGCAAAAA
7351  AAGCCCAGCC  TATTACGCTT  GGAACAACAT  ATCGCAAAAA  AAGATTATGA
7401  GTTTGCTTGT  CGTGAATTAA  TGGTGATTCT  GGAAAAAATG  GACGCTAATT
```

FIG. 7J.

```
7451  TTGGAGGCGT  TCACGATATT  GAATTTGACG  CACCCGCTCA  GCTGGCATAT
7501  CTACCCGAAA  AATTACTAAT  TTATTTTGCC  ACTCGTCTCG  CTAATGCAAT
7551  TACAACACTC  TTTTCCGACC  CCGAATTGGC  AATTTCTGAA  GAAGGGGCGT
7601  TAAAGATGAT  TAGCCTGCAA  CGCTGGTTGA  CGCTGATTTT  TGCCTCTTCC
7651  CCCTACGTTA  ACGCAGACCA  TATTCTCAAT  AAATATAATA  TCAACCCAGA
7701  TTCCGAAGGT  GGCTTTCATT  TAGCAACAGA  CAACTCTTCT  ATTGCTAAAT
7751  TCTGTATTTT  TTACTTACCC  GAATCCAATG  ACTTTGTGCT  TTTAGATGCG
7801  TTATGGGCAG  GGAATCAACA  ACTTTGTGTT  TCATTGTGTT  TTGCGTTGCA
7851  GTCTTCACGT  TTTATTGGTA  CCGCATCTGC  AAACTCGCCG  AGAGCGGTGG
7901  TTTTACAGTG  GTTTCCTAAA  AAACTCGCCG  AAATTGCTAA  TTTAGATGAA
7951  TTGCCTGCAA  ATATCCTTCA  TGATGTATAT  ATGCACTGCA  GTTATGATTT
8001  AGCAAAAAAC  AAGCACGATG  TTAAGCGTCC  ATTAAACGAA  CTTGTCCGCA
8051  AGCATATCCT  CACGCAAGGA  TGGCAAGACC  GCTACCTTTA  CACCTTAGGT
8101  AAAAGGACG   GCAAACCTGT  GATGATGGTA  CTGCTTGAAC  ATTTTAATTC
8151  GGGACATTCG  ATTTATCGTA  CACATTCAAC  TTCAATGATT  GCTGCTCGAG
8201  AAAAATTCTA  TTTAGTCGGC  TTAGGCCATG  AGGGCGTTGA  TAAAATAGGT
```

FIG. 7K.

```
8251  CGAGAAGTGT TTGACGAGTT CTTTGAAATC AGTAGCAATA ATATAATGGA
8301  GAGACTGTTT TTTATCCGTA AACAGTGCGA AACTTTCCAA CCCGCAGTGT
8351  TCTATATGCC AAGCATTGGC ATGGATATTA CCACGATTTT TGTGAGCAAC
8401  ACTCGGCTTG CCCCTATTCA AGCTGTAGCC CTGGGTCATC CTGCCACTAC
8451  GCATTCTGAA TTTATTGATT ATGTCATCGT AGAAGATGAT TATGTGGGCA
8501  GTGAAGATTG TTTCAGCGAA ACCCTTTTAC GCTTACCCAA AGATGCCCTA
8551  CCTTATGTAC CTTCTGCACT CGCCCCACAA AAAGTGGATT ATGTACTCAG
8601  GGAAAACCCT GAAGTAGTCA ATATCGGTAT TGCCGCTACC ACAATGAAAT
8651  TAAACCCTGA ATTTTGCTA ACATTGCAAG AAATCAGAGA TAAAGCTAAA
8701  GTCAAAATAC ATTTTCATTT CGCACTTGGA CAATCAACAG GCTTGACACA
8751  CCCTTATGTC AAATGGTTTA TCGAAAGCTA CACGATTATC GATGCCACTG
8801  CACATCCCCA CGCACCTTAT TCCTTTCGGT TGGCAATATT GCGTGATTGC
8851  GATATGCTAC TAAATCCGTT TTGGTGTATG AATACTAACG GCATAATTGA
8901  TATGGTTACA TTAGGTTTAG TTGGTGTATG CAAAACGGGG GATGAAGTAC
8951  ATGAACATAT TGATGAAGGT CTGTTTAAAC GCTTAGGACT ACCAGAATGG
9001  CTGATAGCCG ACACACGAGA AACATATATT GAATGTGCTT TGCGTCTAGC
9051  AGAAAACCAT CAAGAACGCC TTGAACTCCG TCGTTACATC ATAGAAAACA
```

FIG. 7L.

```
9101  ACGGCTTACA  AAAGCTTTTT  ACAGGCGACC  CTCGTCCATT  GGGCAAAATA
9151  CTGCTTAAGA  AAACAAATGA  ATGGAAGCGG  AAGCACTTGA  GTAAAAAATA
9201  ACGGTTTTTT  AAAGTAAAAG  TGCGGTTAAT  TTTCAAAGCG  TTTTAAAAAC
9251  CTCTCAAAAA  TCAACCGCAC  TTTTATCTTT  ATAACGATCC  CGCACGCTGA
9301  CAGTTTATCA  GCCTCCCGCC  ATAAAACTCC  GCCTTTCATG  GCGGAGATTT
9351  TAGCCAAAAC  TGGCAGAAAT  TAAAGGCTAA  AATCACCAAA  TTGCACCACA
9401  AAATCACCAA  TACCCACAAA  AAA
```

FIG. 8A.

```
  1 GATCAATCTG GGCGATATTT TTGCCAAAGG TGGTAACATT AATGTCCGCG
 51 CTGCCACTAT TCGCAATAAA GGTAAACTTT CTGCCGACTC TGTAAGCAAA
101 GATAAAAGTG GTAACATTGT TCTCTCTGCC AAAGAAGGTG AAGCGGAAAT
151 TGGCGGTGTA ATTTCCGCTC AAAATCAGCA AGCCAAAGGT GGTAAGTTGA
201 TGATTACAGG CGATAAAGTT ACATTGAAAA CGGGTGCAGT TATCGACCTT
251 TCGGGTAAAG AAGGGGGAGA AACTTATCTT GGCGGTGACG AGCGTGGCGA
301 AGGTAAAAAC GGCATTCAAT TAGCAAAGAA AACCACTTTA GAAAAAGGCT
351 CAACAATTAA TGTGTCAGGT AAAGAAAAAG GTGGGCGCGC TATTGTATGG
401 GGCGATATTG CGTTAATTGA CGGCAATATT AATGCCCAAG GTAAAGATAT
451 CGCTAAAACT GGTGGTTTTG TGGAGACGTC GGGGCATTAC TTATCCATTG
501 ATGATAACGC AATTGTTAAA ACAAAAGAAT GGCTACTAGA CCCAGAGAAT
551 GTGACTATTG AAGCTCCTTC CGCTTCTCGC GTCGAGCTGG GTGCCGATAG
601 GAATTCCCAC TCGGCAGAGG TGATAAAAGT GACCCTAAAA AAAATAACA
651 CCTCCTTGAC AACACTAACC AATACAACCA TTTCAAATCT TCTGAAAAGT
701 GCCCACGTGG TGAACATAAC GGCAAGGAGA AAACTTACCG TTAATAGCTC
751 TATCAGTATA GAAAGAGGCT CCCACTTAAT TCTCCACAGT GAAGGTCAGG
```

FIG. 8B.

```
 801  GCGGTCAAGG TGTTCAGATT GATAAAGATA TTACTTCTGA AGGCGGAAAT
 851  TTAACCATTT ATTCTGGCGG ATGGGTTGAT GTTCATAAAA ATATTACGCT
 901  TGGTAGCGGC TTTTTAAACA TCACAACTAA AGAAGGAGAT ATCGCCTTCG
 951  AAGACAAGTC TGGACGGAAC AACCTAACCA TTACAGCCCA AGGGACCATC
1001  ACCTCAGGTA ATAGTAACGG CTTTAGATTT AACAACGTCT CTCTAAACAG
1051  CCTTGGCGGA AAGCTGAGCT TTACTGACAG CAGAGAGGAC AGAGGTAGAA
1101  GAACTAAGGG TAATATCTCA AACAAATTTG ACGGAACGTT AAACATTTCC
1151  GGAACTGTAG ATATCTCAAT GAAAGCACCC AAAGTCAGCT GGTTTTACAG
1201  AGACAAAGGA CGCACCTACT GGAACGTAAC CACTTTAAAT GTTACCTCGG
1251  GTAGTAAATT TAACCTCTCC ATTGACAGCA CAGGAAGTGG CTCAACAGGT
1301  CCAAGCATAC GCAATGCAGA ATTAAATGGC ATAACATTTA ATAAAGCCAC
1351  TTTTAATATC GCACAAGGCT CAACAGCTAA CTTTAGCATC AAGGCATCAA
1401  TAATGCCCTT TAAGAGTAAC GCTAACTACG CATTATTTAA TGAAGATATT
1451  TCAGTCTCAG GGGGGGGTAG CGTTAATTTC AAACTTAACG CCTCATCTAG
1501  CAACATACAA ACCCCTGGCG TAATTATAAA ATCTCAAAAC TTTAATGTCT
1551  CAGGAGGGTC AACTTTAAAT CTCAAGGCTG AAGGTTCAAC AGAAACCGCT
1601  TTTCAATAG AAAATGATTT AAACTTAAAC GCCACCGGTG GCAATATAAC
```

FIG. 8C.

```
1651  AATCAGACAA  GTCGAGGGTA  CCGATTCACG  CGTCAACAAA  GGTGTCGCAG
1701  CCAAAAAAAA  CATAACTTTT  AAAGGGGGTA  ATATCACCTT  CGGCTCTCAA
1751  AAAGCCACAA  CAGAAATCAA  AGGCAATGTT  ACCATCAATA  AAAACACTAA
1801  CGCTACTCTT  CGTGGTGCGA  ATTTTGCCGA  AAACAAATCG  CCTTTAAATA
1851  TAGCAGGAAA  TGTTATTAAT  AATGGCAACC  TTACCACTGC  CGGCTCCATT
1901  ATCAATATAG  CCGAAATCT   TACTGTTTCA  AAAGGCGCTA  ACCTTCAAGC
1951  TATAACAAAT  TACACTTTTA  ATGTAGCCGG  CTCATTTGAC  AACAATGGCG
2001  CTTCAAACAT  TTCCATTGCC  AGAGGAGGGG  CTAAATTTAA  AGATATCAAT
2051  AACACCAGTA  GCTTAAATAT  TACCACCAAC  TCTGATACCA  CTTACCGCAC
2101  CATTATAAAA  GGCAATATAT  CCAACAAATC  AGGTGATTTG  AATATTATTG
2151  ATAAAAAAAG  CGACGCTGAA  ATCCAAATTG  GCGGCAATAT  CTCACAAAAA
2201  GAAGGCAATC  TCACAATTTC  TTCTGATAAA  GTAAATATTA  CCAATCAGAT
2251  AACAATCAAA  GCAGGCCGTTG  AAGGGGGCG   TTCTGATTCA  AGTGAGGCAG
2301  AAAATGCTAA  CCTAACTATT  CAAACCAAAG  AGTTAAAATT  GGCAGGAGAC
2351  CTAAATATTT  CAGGCTTTAA  TAAAGCAGAA  ATTACAGCTA  AAATGGCAG
2401  TGATTTAACT  ATTGGCAATG  CTAGCGGTGG  TAATGCTGAT  GCTAAAAAAG
```

FIG. 8D.

```
2451  TGACTTTTGA CAAGGTTAAA GATTCAAAAA TCTCGACTGA CGGTCACAAT
2501  GTAACACTAA ATAGCGAAGT GAAAACGTCT AATGGTAGTA GCAATGCTGG
2551  TAATGATAAC AGCACCGGTT TAACCATTTC CGCAAAAGAT GTAACGGTAA
2601  ACAATAAACGT TACCTCCCAC AAGACAATAA ATATCTCTGC CGCAGCAGGA
2651  AATGTAACAA CCAAAGAAGG CACAACTATC AATGCAACCA CAGGCAGCGT
2701  GGAAGTAACT GCTCAAAATG GTACAATTAA AGGCAACATT ACCTCGCAAA
2751  ATGTAACAGT GACAGCAACA GAAAATCTTG TTACCACAGA GAATGCTGTC
2801  ATTAATGCAA CCAGCGGCAC AGTAAACATT AGTACAAAAA CAGGGATAT
2851  TAAAGGTGGA ATTGAATCAA CTTCCGGTAA TGTAAATATT ACAGCGAGCG
2901  GCAATACACT TAAGGTAAGT AATATCACTG GTCAAGATGT AACAGTAACA
2951  GCGGATGCAG GAGCCCTTGAC AACTACAGCA GGCTCAACCA TTAGTGCGAC
3001  AACAGGCAAT GCAAATATTA CAACCAAAAC AGGTGATATC AACGGTAAAG
3051  TTGAATCCAG CTCCGGCTCT GTAACACTTG TTGCAACTGG AGCAACTCTT
3101  GCTGTAGGTA ATATTCAGG TAACACTGTT ACTATTACTG CGGATAGCGG
3151  TAAATTAACC TCCACAGTAG GTTCTACAAT TAATGGGACT AATAGTGTAA
3201  CCACCTCAAG CCAATCAGGC GATATTGAAG GTACAATTTC TGGTAATACA
3251  GTAAATGTTA CAGCAAGCAC TGGTGATTTA ACTATTGGAA ATAGTGCAAA
```

FIG. 8E.

```
3301  AGTTGAAGCG AAAAATGGAG CTGCAACCTT AACTGCTGAA TCAGGCAAAT
3351  TAACCACCCA AACAGGCTCT AGCATTACCT CAAGCAATGG TCAGACAACT
3401  CTTACAGCCA AGGATAGCAG TATCGCAGGA AACATTAATG CTGCTAATGT
3451  GACGTTAAAT ACCACAGGCA CTTTAACTAC TACAGGGGAT TCAAAGATTA
3501  ACGCAACCAG TGGTACCTTA ACAATCAATG CAAAAGATGC CAAATTAGAT
3551  GGTGCTGCAT CAGGTGACCG CACAGTAGTA AATGCAACTA ACGCAAGTGG
3601  CTCTGGTAAC GTGACTGCCA AAACCTCAAG CAGCGTGAAT ATCACCGGGG
3651  ATTTAAACAC AATAAATGGG TTAAATATCA TTTCGGAAAA TGGTAGAAAC
3701  ACTGTGCGCT TAAGAGGCAA GGAAATTGAT GTGAAATATA TCCAACCAGG
3751  TGTAGCAAGC ACAACCAAAC TAATTGAAGC GAAACGCGTC CTTGAGAAGG
3801  TAAAAGATTT ATCTGATGAA GTAGAAGAGG GAAAGAGAAA CACTAGCCAA ACTTGGTGTA
3851  AGTGCTGTAC GTTTCGTTGA GCCAAATAAT GCCATTACGG TTAATACACA
3901  AAACGAGTTT ACAACCAAAC CATCAAGTCA AGTGACAATT TCTGAAGGTA
3951  AGGCGTGTTT CTCAAGTGGT AATGGCGCAC AGTGACAATT TCTGAAGGTA
4001  GACGATGGAC AGCAGTAGTC AGTAATTGAC AAGGTAGATT TCATCCTGCA
4051  ATGAAGTCAT TTTATTTTCG TATTATTTAC TGTGTGGGTT AAAGTTCAGT
```

FIG. 8F.

```
4101  ACGGGCTTTA CCCACCTTGT AAAAAATTAC GAAAAATACA ATAAAGTATT
4151  TTTAACAGGT TATTATTATG AAAAACATAA AAAGCAGATT AAAACTCAGT
4201  GCAATATCAA TATTGCTTGG CTTGGCTTCT TCATCGACGT ATGCAGAAGA
4251  AGCGTTTTTA GTAAAAGGCT TTCAGTTATC TGGCGCG
```

FIG. 9A.

```
  1  GGGAATGAGC GTCGTACACG GTACAGCAAC CATGCAAGTA GACGGCAATA
 51  AAACCACTAT CCGTAATAGC GTCAATGCTA TCATCAATTG GAAACAATTT
101  AACATTGACC AAAATGAAAT GGAGCAGTTT TTACAAGAAA GCAGCAACTC
151  TGCCGTTTTC AACCGTGTTA CATCTGACCA AATCTCCCAA TTAAAGGGA
201  TTTTAGATTC TAACGGACAA GTCTTTTTAA TCAACCCAAA TGGTATCACA
251  ATAGGTAAAG ACGCAATTAT TAACACTAAT GGCTTTACTG CTTCTACGCT
301  AGACATTTCT AACGAAAACA TCAAGGGCGC TAATTTCACC CTTGAGCAAA
351  CCAAGGATAA AGCACTCGCT GAAATCGTGA ATCACGGTTT AATTACCGTT
401  GGTAAAGACG GTAGCGTAAA CCTTATTGGT GGCAAAGTGA AAAACGAGGG
451  CGTGATTAGC GTAAATGGCG GTAGTATTTC TTTACTTGCA GGGCAAAAAA
501  TCACCATCAG CGATATAATA AATCCAACCA TCACTTACAG CATTGCTGCA
551  CCTGAAAACG AAGCGATCAA TCTGGGCGAT ATTTTTGCCA AAGGTGGTAA
601  CATTAATGTC CGCGCTGCCA CTATTCGCAA TAAAGGTAAA CTTTCTGCCG
651  ACTCTGTAAG CAAAGATAAA AGTGGTAACA TTGTTCTCTC TGCCAAAGAA
701  GGTGAAGCGG AAATTGGCGG TGTAATTTCC GCTCAAAATC AGCAAGCCAA
751  AGGTGGTAAG TTGATGATTA CAGGTGATAA AGTCACATTA AAAACAGGTG
```

FIG. 9B.

```
 801  CAGTTATCGA CCTTTCAGGT AAAGAAGGGG GAGAGACTTA TCTTGGCGGT
 851  GATGAGCGTG GCGAAGGTAA AAATGGTATT CAATTAGCGA AGAAAACCTC
 901  TTTAGAAAAA GGCTCGACAA TTAATGTATC AGGCAAAGAA AAAGGCGGGC
 951  GCGCTATTGT ATGGGGCGAT ATTGCATTAA TTAATGGTAA CATTAATGCT
1001  CAAGGTAGCG ATATTGCTAA AACTGGCGGC TTTGTGAAAA CATCAGGACA
1051  TGACTTATCC ATTGGTGATG ATGTGATTGT TGACGCTAAA GAGTGGTTAT
1101  TAGACCCAGA TGATGTGTCC ATTGAAACTC TTACATCTGG ACGCAATAAT
1151  ACCGGCGAAA ACCAAGGATA TACAACAGGA GATGGGACTA AAGAGTCACC
1201  TAAAGGTAAT AGTATTTCTA AACCTACATT AACAAACTCA ACTCTTGAGC
1251  AAATCCTAAG AAGAGGTTCT TATGTTAATA TCACTGCTAA TAATAGAATT
1301  TATGTTAATA GCTCCATCAA CTTATCTAAT GGCAGTTTAA CACTTCACAC
1351  TAAACGAGAT GGAGTTAAAA TTAACGGTGA TATTACCTGA AACGAAAATG
1401  GTAATTTAAC CATTAAAGCA GGCTCTTGGG TTGATGTTCA TAAAAACATC
1451  ACGCTTGGTA CGGGTTTTTT GAATATTGTC GCTGGGGATT CTGTAGCTTT
1501  TGAGAGAGAG GGCGATAAAG CACGTAACGC AACAGATGCT CAAATTACCG
1551  CACAAGGGAC GATAACCGTC AATAAAGATG ATAAACAATT TAGATTCAAT
1601  AATGTATCTA TTAACGGGAC GGGCAAGGGT TTAAAGTTTA TTGCAAATCA
```

FIG. 9C.

```
1651  AAATAATTTC  ACTCATAAAT  TTGATGGCGA  AATTAACATA  TCTGGAATAG
1701  TAACAATTAA  CCAAACCACG  AAAAAGATG   TTAAATACTG  GAATGCATCA
1751  AAAGACTCTT  ACTGGAATGT  TTCTTCTCTT  ACTTTGAATA  CGGTGCAAAA
1801  ATTTACCTTT  ATAAAATTCG  TTGATAGCGG  CTCAAATTCC  CAAGATTTGA
1851  GGTCATCACG  TAGAAGTTTT  GCAGGCGTAC  ATTTTAACGG  CATCGGAGGC
1901  AAAACAAACT  TCAACATCGG  AGCTAACGCA  AAAGCCTTAT  TTAAATTAAA
1951  ACCAAACGCC  GCTACAGACC  CAAAAAAAGA  ATTACCTATT  ACTTTTAACG
2001  CCAACATTAC  AGCTACCGGT  AACAGTGATA  GCTCTGTGAT  GTTGACATA
2051  CACGCCAATC  TTACCTCTAG  AGCTGCCGGC  ATAAACATGG  ATTCAATTAA
2101  CATTACCGGC  GGGCTTGACT  TTTCCATAAC  ATCCCATAAT  CGCAATAGTA
2151  ATGCTTTTGA  AATCAAAAAA  GACTTAACTA  TAAATGCAAC  TGGCTCGAAT
2201  TTTAGTCTTA  AGCAAACGAA  AGATTCTTTT  TATAATGAAT  ACAGCAAACA
2251  CGCCATTAAC  TCAAGTCATA  ATCTAACCAT  TCTTGGCGGC  AATGTCACTC
2301  TAGGTGGGA   AAATTCAAGC  AGTAGCATTA  CGGGCAATAT  CAATATCACC
2351  AATAAAGCAA  ATGTTACATT  ACAAGCTGAC  ACCAGCAACA  GCAACACAGG
2401  CTTGAAGAAA  AGAACTCTAA  CTCTTGGCAA  TATATCTGTT  GAGGGAATT
```

FIG. 9D.

| | | | | | |
|---|---|---|---|---|---|
| 2451 | TAAGCCTAAC | TGGTGCAAAT | GCAAACATTG | TCGGCAATCT | TTCTATTGCA |
| 2501 | GAAGATTCCA | CATTTAAAGG | AGAAGCCAGT | GACAACCTAA | ACATCACCGG |
| 2551 | CACCTTTACC | AACAACGGTA | CCGCCAACAT | TAATATAAAA | CAAGGAGTGG |
| 2601 | TAAAACTCCA | AGGCGATATT | ATCAATAAAG | GTGGTTTAAA | TATCACTACT |
| 2651 | AACGCCTCAG | GCACTCAAAA | AACCATTATT | AACGGAAATA | TAACTAACGA |
| 2701 | AAAAGGCGAC | TTAAACATCA | AGAATATTAA | AGCCGACGCC | GAAATCCAAA |
| 2751 | TTGGCGGCAA | TATCTCACAA | AAAGAAGGCA | ATCTCACAAT | TTCTTCTGAT |
| 2801 | AAAGTAAATA | TTACCAATCA | GATAACAATC | AAAGCAGGCG | TTGAAGGGGG |
| 2851 | GCGTTCTGAT | TCAAGTGAGG | CAGAAAATGC | TAACCTAACT | ATTCAAACCA |
| 2901 | AAGAGTTAAA | ATTGGCAGGA | GACCTAAATA | TTTCAGGCTT | TAATAAAGCA |
| 2951 | GAAATTACAG | CTAAAAAATGG | CAGTGATTTA | ACTATTGGCA | ATGCTAGCGG |
| 3001 | TGGTAATGCT | GATGCTAAAA | AAGTGACTTT | TGACAAGGTT | AAAGATTCAA |
| 3051 | AAATCTCGAC | TGACGGTCAC | AATGTAACAC | TAAATAGCGA | AGTGAAAACG |
| 3101 | TCTAATGGTA | GTAGCAATGC | TGGTAATGAT | AACAGCACCG | GTTTAACCAT |
| 3151 | TTCCGCAAAA | GATGTAACGG | TAAACAATAA | CGTTACCTCC | CACAAGACAA |
| 3201 | TAAATATCTC | TGCCGCAGCA | GGAAATGTAA | CAACCAAAGA | AGGCACAACT |
| 3251 | ATCAATGCAA | CCACAGGCAG | CGTGGAAGTA | ACTGCTCAAA | ATGGTACAAT |

FIG. 9E.

```
3301 TAAAGGCAAC ATTACCTCGC AAAATGTAAC AGTGACAGCA ACAGAAAATC
3351 TTGTTACCAC AGAGAATGCT GTCATTAATG CAACCAGCGG CACAGTAAAC
3401 ATTAGTACAA AAACAGGGGA TATTAAAGGT GGAATTGAAT CAACTTCCGG
3451 TAATGTAAAT ATTACAGCGA GCGGCAATAC ACTTAAGGTA AGTAATATCA
3501 CTGGTCAAGA TGTAACAGTA ACAGCGGATG CAGGAGCCTT GACAACTACA
3551 GCAGGCTCAA CCATTAGTGC GACAACAGGC AATGCAAATA TTACAACCAA
3601 AACAGGTGAT ATCAACGTTA AAGTTGAATC CAGCTCCGGC TCTGTAACAC
3651 TTGTTGCAAC TGGAGCAACT CTTGCTGTAG GTAATATTTC AGGTAACACT
3701 GTTACTATTG CTGCGGATAG CGGTAAATTA ACCTCCACAG TAGGTTCTAC
3751 AATTAATGGG ACTAATAGTG TAACCACCTC AAGCCAATCA GGCGATATTG
3801 AAGGTACAAT TTCTGGTAAT ACAGTAAATG TTACAGCAAG CACTGGTGAT
3851 TTAACTATTG GAAATAGTGC AAAAGTTGAA GCGAAAAATG GAGCTGCAAC
3901 CTTAACTGCT GAATCAGGCA AATTAACCAC CCAAACAGGC TCTAGCATTA
3951 CCTCAAGCAA TGGTCAGACA ACTCTTACAG CCAAGGATAG CAGTATCGCA
4001 GGAAACATTA ATGCTGCTAA TGTGACGTTA AATACCACAG GCACTTTAAC
4051 TACTACAGGG GATTCAAAGA TTAACGCAAC CAGTGGTACC TTAACAATCA
```

FIG. 9F.

```
4101 ATGCAAAAGA TGCCAAATTA GATGGTGCTG CATCAGGTGA CCGCACAGTA
4151 GTAAATGCAA CTAACGCAAG TGGCTCTGGT AACGTGACTG CGAAACCTC
4201 AAGCAGCGTG AATATCACCG GGGATTTAAA CACAATAAAT GGGTTAAATA
4251 TCATTTCGGA AAATGGTAGA AACACTGTGC GCTTAAGAGG CAAGGAAATT
4301 GATGTGAAAT ATATCCAACC AGGTGTAGCA AGCGTAGAAG AGTAATTGA
4351 AGCGAAACGC GTCCTTGAGA AGGTAAAAGA TTTATCTGAT GAAGAAAGAG
4401 AAACACTAGC CAAACTTGGT GTAAGTGCTG TACGTTTCGT TGAGCCAAAT
4451 AATGCCATTA CGGTTAATAC ACAAAACGAG TTTACAACCA AACCATCAAG
4501 TCAAGTGACA ATTTCTGAAG GTAAGGCGTG TTTCTCAAGT GGTAATGGCG
4551 CACGAGTATG TACCAATGTT GCTGACGATG GACAGCAGTA GTCAGTAATT
4601 GACAAGGTAG ATTTCATCCT GCAATGAAGT CATTTTATTT TCGTATTATT
4651 TACTGTGTGG GTTAAAGTTC AGTACGGGCT TTACCCACCT TGTAAAAAAT
4701 TA
```

FIG. 10A. COMPARISON OF DERIVED AMINO ACID SEQUENCE

```
                   1                                                          50
Hmw3com   ..........  ..........  ..........  ..........  ..........
Hmw4com   ..........  ..........  ..........  ..........  ..........
Hmw1com   MNKIYRLKFS  KRLNALVAVS  ELARGCDHST  EKGSEKPARM  KVRHLALKPL
Hmw2com   MNKIYRLKFS  KRLNALVAVS  ELARGCDHST  EKGSEKPARM  KVRHLALKPL 51                                                         100
Hmw3com   ..........  ..........  ..........  ..........  ..........
Hmw4com   ..........  ..........  ..GMSVVHGT  ATMQVDGNKT  TIRNSVNAII
Hmw1com   SAMLLSLGVT  SIPQSVLASG  LQGMSVVHGT  ATMQVDGNKT  TIRNSVNAII
Hmw2com   SAMLLSLGVT  SIPQSVLASG  LQGMSVVHGT  ATMQVDGNKT  TIRNSVNAII 101                                                         150
Hmw3com   ..........  ..........  ..........  ..........  ..........
Hmw4com   NWKQFNIDQN  EMEQFLQESS  NSAVFNRVTS  DQISQLKGIL  DSNGQVFLIN
```

FIG. 10B.

```
Hmw1com   NWKQFNIDQN  EMVQFLQENN  NSAVFNRVTS  NQISQLKGIL  DSNGQVFLIN
Hmw2com   NWKQFNIDQN  EMVQFLQENN  NSAVFNRVTS  NQISQLKGIL  DSNGQVFLIN
                                                                 200
          151
Hmw3com   ..........  ..........  ..........  ..........  ..........
Hmw4com   PNGITIGKDA  IINTNGFTAS  TLDISNENIK  ARNFTLEQTK  DKALAEIVNH
Hmw1com   PNGITIGKDA  IINTNGFTAS  TLDISNENIK  ARNFTLEQTK  DKALAEIVNH
Hmw2com   PNGITIGKDA  IINTNGFTAS  TLDISNENIK  ARNFTLEQTK  DKALAEIVNH
                                                                 250
          201
Hmw3com   ..........  ..........  ..........  ..........  ..........
Hmw4com   GLITVGKDGS  VNLIGGKVKN  EGVISVNGGS  ISLLAGQKIT  ISDIINPTIT
Hmw1com   GLITVGKDGS  VNLIGGKVKN  EGVISVNGGS  ISLLAGQKIT  ISDIINPTIT
Hmw2com   GLITVGKDGS  VNLIGGKVKN  EGVISVNGGS  ISLLAGQKIT  ISDIINPTIT
                                                                 300
          251
Hmw3com   ..........  INLGDIFAKG  GNINVRAATI  RNKGKLSADS  VSKDKSGNIV
```

FIG. 10C.

| | | | | | | |
|---|---|---|---|---|---|---|
| Hmw4com | YSIAAPENEA | INLGDIFAKG | GNINVRAATI | RNKGKLSADS | VSKDKSGNIV | |
| Hmw1com | YSIAAPENEA | VNLGDIFAKG | GNINVRAATI | RNKGKLSADS | VSKDKSGNIV | |
| Hmw2com | YSIAAPENEA | VNLGDIFAKG | GNINVRAATI | RNKGKLSADS | VSKDKSGNIV | |

301                                                                    350

| | | | | | | |
|---|---|---|---|---|---|---|
| Hmw3com | LSAKEGEAEI | GGVISAQNQQ | AKGGKLMITG | DKVTLKTGAV | IDLSGKEGGE | |
| Hmw4com | LSAKEGEAEI | GGVISAQNQQ | AKGGKLMITG | DKVTLKTGAV | IDLSGKEGGE | |
| Hmw1com | LSAKEGEAEI | GGVISAQNQQ | AKGGKLMITG | DKVTLKTGAV | IDLSGKEGGE | |
| Hmw2com | LSAKEGEAEI | GGVISAQNQQ | AKGGKLMITG | DKVTLKTGAV | IDLSGKEGGE | |

351                                                                    400

| | | | | | | |
|---|---|---|---|---|---|---|
| Hmw3com | TYLGGDERGE | GKNGIQLAKK | TTLEKGSTIN | VSGKEKGGRA | IVWGDIALID | |
| Hmw4com | TYLGGDERGE | GKNGIQLAKK | TTLEKGSTIN | VSGKEKGGRA | IVWGDIALID | |
| Hmw1com | TYLGGDERGE | GKNGIQLAKK | TTLEKGSTIN | VSGKEKGGRA | IVWGDIALID | |
| Hmw2com | TYLGGDERGE | GKNGIQLAKK | TTLEKGSTIN | VSGKEKGGRA | IVWGDIALID | |

FIG. 10D.

```
        401
Hmw3com  GNINAQGK.D  IAKTGGFVET  SGHYLSIDDN  AIVKTKEWLL  DPENVTIEAP
Hmw4com  GNINAQGS.D  IAKTGGFVET  SGHDLSIGDD  VIVDAKEWLL  DPDDVSIETL
Hmw1com  GNINAQGSGD  IAKTGGFVET  SGHDLFIKDN  AIVDAKEWLL  DPDNVTINAE
Hmw2com  GNINAQGSGD  IAKTGGFVET  SGHYLSIESN  AIVKTKEWLL  DPDDVTIEAE
                                                              450

451                                                   500
Hmw3com  SASRVELGAD  RNSHSAEVIK  VTLKKNNTSL  TTLTNTTISN  LLKSAHVVNI
Hmw4com  TSGRNNTGEN  QGYTTGDGTK  ESPKGNSISK  PTLTNSTLEQ  ILRRGSYVNI
Hmw1com  TAGRSNTSED  DEYTGSGNSA  STPKRNKE.K  TTLTNTTLES  ILKKGTFVNI
Hmw2com  DPLRNNTGIN  DEFPTGTGEA  SDPKKNSELK  TTLTNTTISN  YLKNAWTMNI 501                                                   550
Hmw3com  TARRKLTVNS  SISIERGSHL  ILHSEGQGGQ  GVQIDKDITS  .E...GGNLT
Hmw4com  TANNRIYVNS  SINLSNGS.L  TLHTK...RD  GVKINGDITS  NE...NGNLT
Hmw1com  TANQRIYVNS  SINL.SNGSL  TLWSEGRSGG  GVEINNDITT  GDDTRGANLT
Hmw2com  TASRKLTVNS  SINGSNGSHL  ILHSKGQRGG  GVQIDGDIT.  ...SKGGNLT
```

FIG. 10E.

```
         551
Hmw3com  IYSGGWVDVH  KNITLGS.GF  LNITTKEGDI  AFEDKSGR..  ..NNLTITAQ
Hmw4com  IKAGSWVDVH  KNITLGT.GF  LNIVAGDS.V  AFEREGDKAR  NATDAQITAQ
Hmw1com  IYSGGWVDVH  KNISLGAQGN  INITAKQD.I  AFEKGSNQV.  ......ITGQ
Hmw2com  IYSGGWVDVH  KNITLD.QGF  LNITA.AS.V  AFEGGNNKAR  DANNLTITAQ
                                                              600

601                                                  650
Hmw3com  GTITSG.NSN  GFRFNNVSLN  SLGGKLSFTD  SREDRGRRTK  GNISNKFDGT
Hmw4com  GTITVNKDDK  QFRFNNVSIN  GTGKGLKFIA  NQN.......  .NFTHKFDGE
Hmw1com  GTIT.SGNQK  GFRFNNVSLN  GTGSGLQFTT  KRTN......K  YAITNKFEGT
Hmw2com  GTVTITGEGK  DFRANNVSLN  GTGKGLNIIS  SVNN......  ..LTHNLSGT 651                                                  700
Hmw3com  LNISGTVDIS  MKAPKVSWFY  RD.KGRTYWN  VTTLNVTSGS  KFNLSIDSTG
Hmw4com  INISGIVTIN  QTTKKDVKYW  NA.SKDSYWN  VSSLTLNTVQ  KFTF.IKFVD
Hmw1com  LNISGKVNIS  MVLPKNESGY  DKFKGRTYWN  LTSLNVSESG  EFNLTIDSRG
```

FIG. 10F.

```
Hmw2com  INISGNITIN QTTRKNTSYW QTSHD.SHWN VSALNLETGA NFTF.IKYIS 701                                             750
Hmw3com  SGSTG...PS IRNA..ELNG ITFN....KA TFNIAQGSTA NFSIKASIMP
Hmw4com  SGSNS...QD LRSSRRSFAG VHFNGIGGKT NFNIGANAKA LFKLKPNAAT
Hmw1com  SDSAGTLTQ. ....PYNLNG ISFN...KDT TFNVERNARV NFDIKAPIGI
Hmw2com  SNSKGLTTQY RSSAGVNFNG V..N...GNM SFNLKEGAKV NFKLKPNENM 751                                             800
Hmw3com  FKSNANYAL. FNEDISVSG. .GGSVNFKLN ASSSNIQTPG VIIKSQNFNV
Hmw4com  DPKKELPIT. FNANITATGN SDSSVMFDIH A...NLTSRA AGINMDSINI
Hmw1com  NKYSSLNYAS FNGNISVSG. .GGSVDFTLL ASSSNVQTPG VVINSKYFNV
Hmw2com  NTSKPLPI.R FLANITATG. .GGSVFFDIY ANHS...GRG AELKMSEINI 801                                             850
Hmw3com  SGGSTLNLKA EGSTETAFSI ENDLNLNATG GNITIRQVEG T..DSRVNKG
Hmw4com  TGGLDFSITS HNRNSNAFEI KKDLTINATG SNFSLKQTKD SFYNEYSKHA
```

FIG. 10G.

```
Hmw1com  STGSSLRFKT  SGSTKTGFSI  EKDLTLNATG  GNITLLQVEG  T..DGMIGKG
Hmw2com  SNGANFTLNS  HVRGDDAFKI  NKDLTINATN  SNFSLRQTKD  DFYDGYARNA
                     851                                        900

Hmw3com  VAAKKNITFK  GGNITFGSQK  ATTEIKGNVT  INKNTNATLR  GANFAEN....
Hmw4com  INSSHNLTIL  GGNVTLGGEN  SSSSITGNIN  ITNKANVTLQ  ADTSNSNTGL
Hmw1com  IVAKKNITFE  GGNITFGSRK  AVTEIEGNVT  INNNANVTLI  GSDFDNHQ...
Hmw2com  INSTYNISIL  GGNVTLGGQN  SSSSITGNIT  IEKAANVTLE  ANNAPNQQNI
                     901                                        950

Hmw3com  KSPLNIAGNV  INNGNLTTAG  SIINIAGNLT  VSKGANLQAI  TNYTFNVAGS
Hmw4com  KKRTLTLGNI  SVEGNLSLTG  ANANIVGNLS  IAEDSTFKGE  ASDNLNITGT
Hmw1com  KPLTIKKDVI  INSGNLTAGG  NIVNIAGNLT  VESNANFKAI  TNFTFNVGGL
Hmw2com  RDRVIKLGSL  LVNGSLSLTG  ENADIKGNLT  ISESATFKGK  TRDTLNITGN
         951                                                  1000
```

FIG. 10H.

```
Hmw3com  FDNNGASNIS  IARGGAKFK.  DINNTSSLNI  TTNSDTTYRT  IIKGNISNKS
Hmw4com  FTNNGTANIN  IKQGVVKLQG  DINNKGGLNI  TTNASGTQKT  IINGNITNEK
Hmw1com  FDNKGNSNIS  IAKGGARFK.  DIDNSKNLSI  TTNSSSTYRT  IISGNITNKN
Hmw2com  FTNNGTAEIN  ITQGVVKLG.  NVTNDGDLNI  TTHAKRNQRS  IIGGDIINNK 1001                                           1050
Hmw3com  GDLNIIDKKS  DAEIQIGGNI  SQKEGNLTIS  SDKVNITNQI  TIKAGVEGGR
Hmw4com  GDLNIKNIKA  DAEIQIGGNI  SQKEGNLTIS  SDKVNITNQI  TIKAGVEGGR
Hmw1com  GDLNITNEGS  DTEMQIGGDI  SQKEGNLTIS  SDKINITKQI  TIKAGVDGEN
Hmw2com  GSLNITDSNN  DAEIQIGGNI  SQKEGNLTIS  SDKINITKQI  TIKKGIDGED 1051                                           1100
Hmw3com  SDSSEAENAN  LTIQTKELKL  AGDLNISGFN  KAEITAKNGS  DLTIGNASGG
Hmw4com  SDSSEAENAN  LTIQTKELKL  AGDLNISGFN  KAEITAKNGS  DLTIGNASGG
Hmw1com  SDSDATNNAN  LTIKTKELKL  TQDLNISGFN  KAEITAKDGS  DLTIGNTNSA
Hmw2com  SSSDATSNAN  LTIKTKELKL  TEDLSISGFN  KAEITAKDGR  DLTIGNSNDG
```

FIG. 10I.

```
          1101                                                      1150
Hmw3com   N..ADAKKVT  FDKVKDSKIS  TDGHNVTLNS  EVKT..SNGS  SNAGNDNSTG
Hmw4com   N..ADAKKVT  FDKVKDSKIS  TDGHNVTLNS  EVKT..SNGS  SNAGNDNSTG
Hmw1com   D.GTNAKKVT  FNQVKDSKIS  ADGHKVTLHS  KVETSGSNNN  TEDSSDNNAG
Hmw2com   NSGAEAKKVT  FNNVKDSKIS  ADGHNVTLNS  KVKTSSSNGG  RESNSDNDTG 1151                                                      1200
Hmw3com   LTISAKDVTV  NNNVTSHKTI  NISAAAGNVT  TKEGTTINAT  TGSVEVTAQN
Hmw4com   LTISAKDVTV  NNNVTSHKTI  NISAAAGNVT  TKEGTTINAT  TGSVEVTAQN
Hmw1com   LTIDAKNVTV  NNNITSHKAV  SISATSGEIT  TKTGTTINAT  TGNVEIT...
Hmw2com   LTITAKNVEV  NKDVTSLKTV  NITA.SEKVT  TTAGSTINAT  NGKASIT...

1201                                                      1250
Hmw3com   GTIKGNITSQ  NVTVTATENL  VTTENAVINA  TSGTVNISTK  TGDIKGGIES
Hmw4com   GTIKGNITSQ  NVTVTATENL  VTTENAVINA  TSGTVNISTK  TGDIKGGIES
Hmw1com   ..........  ..........  ..........  ........AQ  TGDIKGGIES
```

FIG. 10J.

```
Hmw2com  ........  ........  ........  ........  ........  .....TK T.......

1251                                                      1300
Hmw3com  TSGNVNITAS GNTLKVSNIT GQDVTVTADA GALTTTAGST ISATTGNANI
Hmw4com  TSGNVNITAS GNTLKVSNIT GQDVTVTADA GALTTTAGST ISATTGNANI
Hmw1com  SSGSVTLTAT EGALAVSNIS GNTVTVTANS GALTTLAGST IKG.TESVTT
Hmw2com  ........  ........  ........  ........  ........

1301                                                      1350
Hmw3com  TTKTGDINGK VESSSGSVTL VATGATLAVG NISGNTVTIT ADSGKLTSTV
Hmw4com  TTKTGDINGK VESSSGSVTL VATGATLAVG NISGNTVTIT ADSGKLTSTV
Hmw1com  SSQSGDIG..  ........  ........ ......G TISGGTVEVK ATESLTTQSN
Hmw2com  ....GDIS..  ........  ........ ......G TISGNTVSVS ATVDLTTKSG 1351                                                      1400
Hmw3com  GSTINGTNSV TTSSQSGDIE GTISGNTVNV TASTGDLTIG NSAKVEAKNG
Hmw4com  GSTINGTNSV TTSSQSGDIE GTISGNTVNV TASTGDLTIG NSAKVEAKNG
```

FIG. 10K.

```
Hmw1com  SKIKATTGEA NVTSATGTIG GTISGNTVNV TANAGDLTVG NGAEINATEG
Hmw2com  SKIEAKSGEA NVTSATGTIG GTISGNTVNV TANAGDLTVG NGAEINATEG
         1401                                              1450

Hmw3com  AATLTAESGK LTTQTGSSIT SSNGQTTLTA KDSSIAGNIN AANVTLNTTG
Hmw4com  AATLTAESGK LTTQTGSSIT SSNGQTTLTA KDSSIAGNIN AANVTLNTTG
Hmw1com  AATLTTSSGK LTTEASSHIT SAKGQVNLSA QDSSVAGSIN AANVTLNTTG
Hmw2com  AATLTATGNT LTTEAGSSIT STKGQVDLLA QNSSIAGNIN AANVTLNTTG
         1451                                              1500

Hmw3com  TLTTTGDSKI NATSGTLTIN AKDAKLDGAA SGDRTVVNAT NASGSGNVTA
Hmw4com  TLTTTGDSKI NATSGTLTIN AKDAKLDGAA SGDRTVVNAT NASGSGNVTA
Hmw1com  TLTTVKGSNI NATSGTLTIN AKDAELNGAA LGNHTVVNAT NANGSGSVIA
Hmw2com  TLTTVAGSDI KATSGTLTIN AKDAKLNGDA SGDSTEVNAV NASGSGVTA
         1501                                              1550
```

FIG.10L.

| | | | | | | |
|---|---|---|---|---|---|---|
| Hmw3com | KTSSSVNITG | DLNTINGLNI | ISENGRNTVR | LRGKEIDVKY | IQPGVASVEE |
| Hmw4com | KTSSSVNITG | DLNTINGLNI | ISENGRNTVR | LRGKEIDVKY | IQPGVASVEE |
| Hmw1com | TTSSRVNITG | DLITINGLNI | ISKNGINTVL | LKGVKIDVKY | IQPGIASVDE |
| Hmw2com | ATSSSVNITG | DLNTVNGLNI | ISKDGRNTVR | LRGKEIEVKY | IQPGVASVEE |

1551                                                           1600

| | | | | | | |
|---|---|---|---|---|---|---|
| Hmw3com | VIEAKRVLEK | VKDLSDEERE | TLAKLGVSAV | RFVEPNNAIT | VNTQNEFTTK |
| Hmw4com | VIEAKRVLEK | VKDLSDEERE | TLAKLGVSAV | RFVEPNNAIT | VNTQNEFTTK |
| Hmw1com | VIEAKRILEK | VKDLSDEERE | ALAKLGVSAV | RFIEPNNTIT | VDTQNEFATR |
| Hmw2com | VIEAKRVLEK | VKDLSDEERE | TLAKLGVSAV | RFVEPNNTIT | VNTQNEFTTR |

1601                                  1632

| | | | |
|---|---|---|---|
| Hmw3com | PSSQVTISEG | KACFSSGNGA | RVCTNVADDG | QQ |
| Hmw4com | PSSQVTISEG | KACFSSGNGA | RVCTNVADDG | QQ |
| Hmw1com | PLSRIVISEG | RACFSNSDGA | TVCVNIADNG | R. |
| Hmw2com | PSSQVIISEG | KACFSSGNGA | RVCTNVADDG | QP |

GENE ENCODING HIGH MOLECULAR SURFACE PROTEIN-2 NON-TYPEABLE HAEMOPHILUS

This is a continuation of application Ser. No. 08/302,832 filed Oct. 5, 1994 now U.S. Pat. No. 5,603,938, which is a national phase filing of International Appl. No. PCT/US93/02166, filed Mar. 16, 1993.

FIELD OF INVENTION

This invention relates to high molecular weight proteins of non-typeable haemophilus.

BACKGROUND TO THE INVENTION

Non-typeable *Haemophilus influenzae* are non-encapsulated organisms that are defined by their lack of reactivity with antisera against known *H. influenzae* capsular antigens.

These organisms commonly inhabit the upper respiratory tract of humans and are frequently responsible for infections, such as otitis media, sinusitis, conjunctivitis, bronchitis and pneumonia. Since these organisms do not have a polysaccharide capsule, they are not controlled by the present *Haemophilus influenzae* type b (Hib) vaccines, which are directed towards Hib bacterial capsular polysaccharides. The non-typeable strains, however, do produce surface antigens that can elicit bactericidal antibodies. Two of the major outer membrane proteins, P2 and P6, have been identified as targets of human serum bactericidal activity. However, it has been shown that the P2 protein sequence is variable, in particular in the non-typeable Haemophilus strains. Thus, a P2-based vaccine would not protect against all strains of the organism.

There have previously been identified by Barenkamp et al (*Pediatr. Infect. Dis. J.*, 9:333–339, 1990) a group of high-molecular-weight (HMW) proteins that appeared to be major targets of antibodies present in human convalescent sera. Examination of a series of middle ear isolates revealed the presence of one or two such proteins in most strains. However, prior to the present invention, the structures of these proteins were unknown as were pure isolates of such proteins.

SUMMARY OF INVENTION

The inventors, in an effort to further characterize the high molecular weight (HMW) Haemophilus proteins, have cloned, expressed and sequenced the genes coding for two immunodominant HMW proteins (designated HMW1 and HMW2) from a prototype non-typeable Haemophilus strain and have cloned, expressed and almost completely sequenced the genes coding for two additional immunodominant HMW proteins (designated HKW3 and HMW4) from another non-typeable Haemophilus strain.

In accordance with one aspect of the present invention, therefore, there is provided an isolated and purified gene coding for a high molecular weight protein of a non-typeable Haemophilus strain, particularly a gene coding for protein HMW1, HMW2, HMW3 or HMW4, as well as any variant or fragment of such protein which retains the immunological ability to protect against disease caused by a non-typeable Haemophilus strain. In another aspect, the invention provides a high molecular weight protein of non-typeable *Haemophilus influenzae* which is encoded by these genes.

BRIEF DESCRIPTION OF DRAWINGS

FIG. 1A–G is a DNA sequence of a gene coding for protein HMW1 (SEQ ID NO: 1);

FIG. 2A–B is a derived amino acid sequence of protein HMW1 (SEQ ID NO: 2);

FIG. 3A–G is a DNA sequence of a gene coding for protein HMW2 (SECLID NO: 3);

FIG. 4A–B is a derived amino acid sequence of HMW2 (SEQ ID NO: 4);

FIG. 5B shows the restriction map of the T7 expression vector pT7-7;

FIG. 6A–L contains the DNA sequence of a gene cluster for the hmw1 gene (SEQ ID NO: 5), comprising nucleotides 351 to 4958 (ORF a) (as in FIG. 1), as well as two additional downstream genes in the 3' flanking region, comprising ORFs b, nucleotides 5114–6748 and c nucleotides 7062–9011;

FIG. 7A–L contains the DNA sequence of a gene cluster for the hmw2 gene (SEQ ID NO: 6), comprising nucleotides 792 to 5222 (ORF a) (as in FIG. 3), as well as two additional downstream genes in the 3' flanking region, comprising ORFs b, nucleotides 5375–7009, and c, nucleotides 7249–9198;

FIG. 8A–F is a partial DNA sequence of a gene coding for protein HMW3 (SEQ ID NO: 7);

FIG. 9A–F is a partial DNA sequence of a gene coding for protein HMW4 (SEQ ID NO: 8); and FIG. 10A–L is a comparison table for the derived amino acid sequence for proteins HMW1, HMW2, HMW3 and HMW4.

GENERAL DESCRIPTION OF INVENTION

Figure 5A:
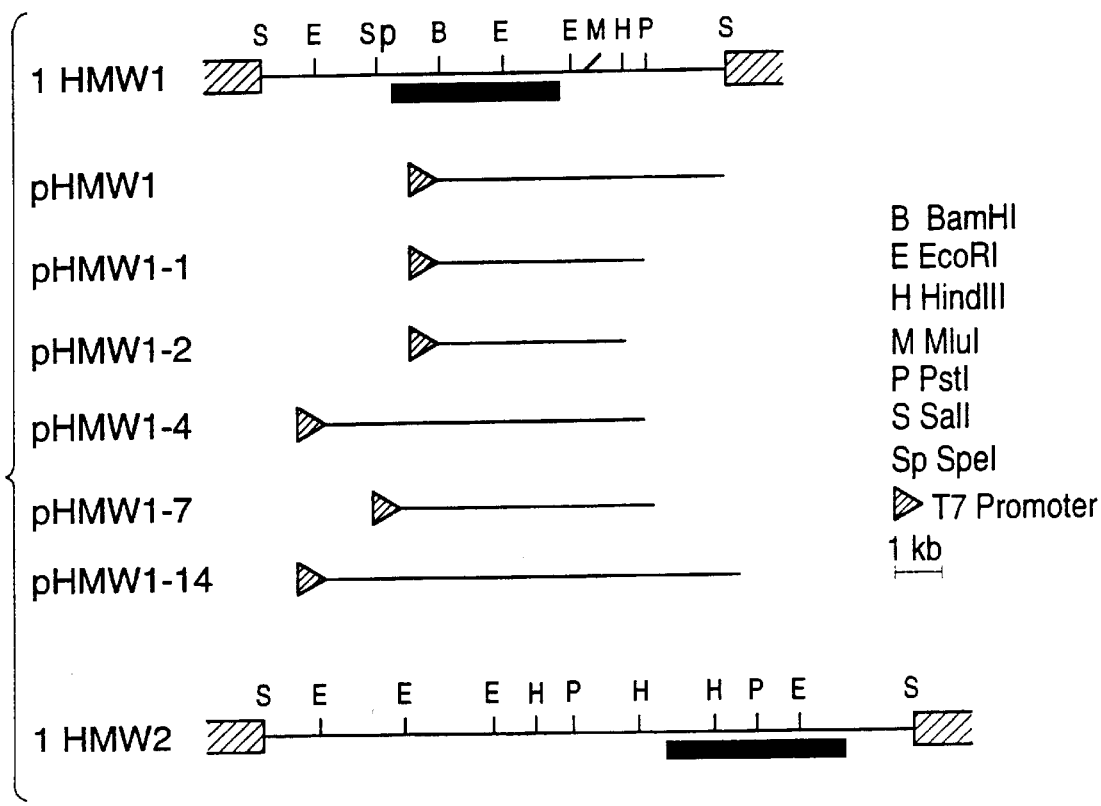
FIG. 5A shows restriction maps of representative recombinant phages which contained the HMW1 or HMW2 structural genes, the locations of the structural genes being indicated by the shaded bars.

The DNA sequences of the genes coding for HMW1 and HMW2, shown in FIGS. 1 and 3 respectively, were shown to be about 80% identical, with the first 1259 base pairs of the genes being identical. The derived amino acid sequences of the two HMW proteins, shown in FIGS. 2 and 4 respectively, are about 70% identical. Furthermore, the encoded proteins are antigenically related to the filamentous hemagglutinin surface protein of *Bordetella pertussis*. A monoclonal antibody prepared against filamentous hemagglutinin (FHA) of *Bordetella pertussis* was found to recognize both of the high molecular weight proteins. This data suggests that the HMW and FHA proteins may serve similar biological functions. The derived amino acid sequences of the HMW1 and HMW2 proteins show sequence similarity to that for the FHA protein. It has further been shown that these antigenically-related proteins are produced by the majority of the non-typeable strains of Haemophilus. Antisera raised against the protein expressed by the HMW1 gene recognizes both the HMW2 protein and the *B. pertussis* FHA. The present invention includes an isolated and purified high molecular weight protein of non-typeable haemophilus which is antigenically related to the *B. pertussis* FHA, which may be obtained from natural sources or produced recombinantly.

A phage genomic library of a known strain of non-typeable Haemophilus was prepared by standard methods and the library was screened for clones expressing high molecular weight proteins, using a high titre antiserum against HMW's. A number of strongly reactive DNA clones were plaque-purified and sub-cloned into a T7 expression plasmid. It was found that they all expressed either one or the other of the two high-molecular-weight proteins designated HMW1 and HMW2, with apparent molecular weights of 125 and 120 kDa, respectively, encoded by open reading frames of 4.6 kb and 4.4 kb, respectively.

Representative clones expressing either HMW1 or HMW2 were further characterized and the genes isolated, purified and sequenced. The DNA sequence of HMW1 is shown in FIG. 1 and the corresponding derived amino acid sequence in FIG. 2. Similarly, the DNA sequence of HMW2 is shown in FIG. 3 and the corresponding derived amino acid sequence in FIG. 4. Partial purification of the isolated proteins and N-terminal sequence analysis indicated that the expressed proteins are truncated since their sequence starts at residue number 442 of both full length HMW1 and HMW2 gene products.

Subcloning studies with respect to the hmw1 and hmw2 genes indicated that correct processing of the HMW proteins required the products of additional downstream genes. It has been found that both the hmw1 and hmw2 genes are flanked by two additional downstream open reading frames (ORFs), designated b and c, respectively, (see FIGS. 6 and 7).

The b ORFs are 1635 bp in length, extending from nucleotides 5114 to 6748 in the case of hmw1 and nucleotides 5375 to 7009 in the case of hmw2, with their derived amino acid sequences 99% identical. The derived amino acid sequences demonstrate similarity with the derived amino acid sequences of two genes which encode proteins required for secretion and activation of hemolysins of *P. mirabilis* and *S. marcescens*.

The c ORFs are 1950 bp in length, extending from nucleotides 7062 to 9011 in the case of hmw1 and nucleotides 7249 to 9198 in the case of hmw2, with their derived amino acid sequences 96% identical. The hmw1 c ORF is preceded by a series of 9 bp direct tandem repeats. In plasmid subclones, interruption of the hmw1 b or c ORF results in defective processing and secretion of the hmw1 structural gene product.

The two high molecular weight proteins have been isolated and purified and shown to be partially protective against otitis media in chinchillas and to function as adhesins. These results indicate the potential for use of such high molecular proteins and structurally-related proteins of other non-typeable strains of *Haemophilus influenzae* as components in non-typeable *Haemophilus influenzae* vaccines.

Since the proteins provided herein are good cross-reactive antigens and are present in the majority of non-typeable Haemophilus strains, it is evident that these HMW proteins may become integral constituents of a universal Haemophilus vaccine. Indeed, these proteins may be used not only as protective antigens against otitis, sinusitis and bronchitis caused by the non-typeable Haemophilus strains, but also may be used as carriers for the protective Hib polysaccharides in a conjugate vaccine against meningitis. The proteins also may be used as carriers for other antigens, haptens and polysaccharides from other organisms, so as to induce immunity to such antigens, haptens and polysaccharides.

The nucleotide sequences encoding two high molecular weight proteins of a different non-typeable Haemophilus strain (designated HMW3 and HMW4) have been largely elucidated, and are presented in FIGS. 8 and 9. HMW3 has an apparent molecular weight of 125 kDa while HMW4 has an apparent molecular weight of 123 kDa. These high molecular weight proteins are antigenically related to the HNW1 and HMW2 proteins and to FHA. Sequence analysis of HMW3 is approximately 85% complete and of HMW4 95% complete, with short stretches at the 5'-ends of each gene remaining to be sequenced.

FIG. 10 contains a multiple sequence comparison of the derived amino acid sequences for the four high molecular weight proteins identified herein. As may be seen from this comparison, stretches of identical peptide sequence may be found throughout the length of the comparison, with HMW3 more closely resembling HMW1 and HMW4 more closely resembling HMW2. This information is highly suggestive of a considerable sequence homology between high molecular weight proteins from various non-typeable Haemophilus strains.

In addition, mutants of non-typeable *H. influenzae* strains that are deficient in expression of HMW1 or HMW2 or both have been constructed and examined for their capacity to adhere to cultured human epithelial cells. The hmw1 and hmw2 gene clusters have been expressed in *E. coli* and have been examined for in vitro adherence. The results of such experimentation demonstrate that both HMW1 and HMW2 mediate attachment and hence are adhesins and that this function is present even in the absence of other *H. influenzae* surface structures.

With the isolation and purification of the high molecular weight proteins, the inventors are able to determine the major protective epitopes by conventional epitope mapping and synthesize peptides corresponding to these determinants to be incorporated in fully synthetic or recombinant vaccines. Accordingly, the invention also comprises a synthetic peptide having an amino acid sequence corresponding to at least one protective epitope of a high molecular weight protein of a non-typeable *Haemophilus influenzae*. Such peptides are of varying length that constitute portions of the high-molecular-weight proteins, that can be used to induce immunity, either directly or as part of a conjugate, against the relative organisms and thus constitute vaccines for protection against the corresponding diseases.

The present invention also provides any variant or fragment of the proteins that retains the potential immunological ability to protect against disease caused by non-typeable Haemophilus strains. The variants may be constructed by partial deletions or mutations of the genes and expression of the resulting modified genes to give the protein variations.

EXAMPLES

Example 1

Non-typeable *H. influenzae* strains 5 and 12 were isolated in pure culture from the middle ear fluid of children with acute otitis media. Chromosomal DNA from strain 12, providing genes encoding proteins HMW1 and HMW2, was prepared by preparing Sau3A partial restriction digests of chromosomal DNA and fractionating on sucrose gradients. Fractions containing DNA fragments in the 9 to 20 kbp range were pooled and a library was prepared by ligation into λEMBL3 arms. Ligation mixtures were packaged in vitro and plate-amplified in a P2 lysogen of *E. coli* LE392.

For plasmid subcloning studies, DNA from a representative recombinant phage was subcloned into the T7 expression plasmid pT7-7, containing the T7 RNA polymerase promoter Φ10, a ribosome-binding site and the translational start site for the T7 gene 10 protein upstream from a multiple cloning site (see FIG. 5B).

DNA sequence analysis was performed by the dideoxy method and both strands of the HMW1 gene and a single strand of the HMW2 gene were sequenced.

Western immunoblot analysis was performed to identify the recombinant proteins being produced by reactive phage clones. Phage lysates grown in LE392 cells or plaques picked directly from a lawn of LE392 cells on YT plates were solubilized in gel electrophoresis sample buffer prior to electrophoresis. Sodium dodecyl sulfate (SDS)-polyacrylamide gel electrophoresis was performed on 7.5% or 11% polyacrylamide modified Laemmli gels. After transfer of the proteins to nitrocellulose sheets, the sheets were probed sequentially with an *E. coli*-absorbed human serum sample containing high-titer antibody to the high-molecular-weight proteins and then with alkaline phosphatase-conjugated goat anti-human immunoglobulin G (IgG) second antibody. Sera from healthy adults contains high-titer antibody directed against surface-exposed high-molecular-weight proteins of non-typeable *H. influenzae*. One such serum sample was used as the screening antiserum after having been extensively absorbed with LE392 cells.

To identify recombinant proteins being produced by *E. coli* transformed with recombinant plasmids, the plasmids of interest were used to transform *E. coli* BL21 (DE3)/pLysS. The transformed strains were grown to an $A_{600}$ of 0.5 in L broth containing 50 μg of ampicillin per ml. IPTG was then added to 1 mM. One hour later, cells were harvested, and a sonicate of the cells was prepared. The protein concentrations of the samples were determined by the bicinchoninic acid method. Cell sonicates containing 100 μg of total protein were solubilized in electrophoresis sample buffer, subjected to SDS-polyacrylamide gel electrophoresis, and transferred to nitrocellulose. The nitrocellulose was then probed sequentially with the *E. coli*-absorbed adult serum sample and then with alkaline phosphatase-conjugated goat anti-human IgG second antibody.

Western immunoblot analysis also was performed to determine whether homologous and heterologous non-typeable *H. influenzae* strains expressed high-molecular-weight proteins antigenically related to the protein encoded by the cloned HMW1 gene (rHMW1). Cell sonicates of bacterial cells were solubilized in electrophoresis sample buffer, subjected to SDS-polyacrylamide gel electrophoresis, and transferred to nitrocellulose. Nitrocellulose was probed sequentially with polyclonal rabbit rHMW1 antiserum and then with alkaline phosphatase-conjugated goat anti-rabbit IgG second antibody.

Finally, Western immunoblot analysis was performed to determine whether non-typeable Haemophilus strains expressed proteins antigenically related to the filamentous hemagglutinin protein of *Bordetella pertussis*. Monoclonal antibody X3C, a murine immunoglobulin G (IgG) antibody which recognizes filamentous hemagglutinin, was used to probe cell sonicates by Western blot. An alkaline phosphatase-conjugated goat anti-mouse IgG second antibody was used for detection.

To generate recombinant protein antiserum, *E. coli* BL21 (DE3)/pLysS was transformed with pHMW1-4, and expression of recombinant protein was induced with IPTG, as described above. A cell sonicate of the bacterial cells was prepared and separated into a supernatant and pellet fraction by centrifugation at 10,000×g for 30 min. The recombinant protein fractionated with the pellet fraction. A rabbit was subcutaneously immunized on biweekly schedule with 1 mg of protein from the pellet fraction, the first dose given with Freund's complete adjuvant and subsequent doses with Freund's incomplete adjuvant. Following the fourth injection, the rabbit was bled. Prior to use in the Western blot assay, the antiserum was absorbed extensively with sonicates of the host *E. coli* strain transformed with cloning vector alone.

To assess the sharing of antigenic determinants between HMW1 and filamentous hemagglutinin, enzyme-linked immunosorbent assay (ELISA) plates (Costar, Cambridge, Mass.) were coated with 60 μl of a 4-ug/ml solution of filamentous hemagglutinin in Dulbecco's phosphate-buffered saline per well for 2 h at room temperature. Wells were blocked for 1 h with 1% bovine serum albumin in Dulbecco's phosphate-buffered saline prior to addition of serum dilutions. rHMW1 antiserum was serially diluted in 0.1% Brij (Sigma, St. Louis, Mo.) in Dulbecco's phosphate-buffered saline and incubated for 3 h at room temperature. After being washed, the plates were incubated with peroxidase-conjugated goat anti-rabbit lgG antibody (Bio-Rad) for 2 h at room temperature and subsequently developed with 2,2'-azino-bis(3-ethylbenzthiazoline-6-sulfonic acid) (Sigma) at a concentration of 0.54 in mg/ml in 0.1M sodium citrate buffer, pH 4.2, containing 0.03% $H_2O_2$. Absorbances were read on an automated ELISA reader.

Recombinant phage expressing HMW1 or HMW2 were recovered as follows. The non-typeable *H. influenzae* strain 12 genomic library was screened for clones expressing high-molecular-weight proteins with an *E. coli*-absorbed human serum sample containing a high titer of antibodies directed against the high-molecular-weight proteins.

Numerous strongly reactive clones were identified along with more weakly reactive ones. Twenty strongly reactive clones were plaque-purified and examined by Western blot for expression of recombinant proteins. Each of the strongly reactive clones expressed one of two types of high-molecular-weight proteins, designated HMW1 and HMW2. The major immunoreactive protein bands in the HMW1 and HMW2 lysates migrated with apparent molecular masses of 125 and 120 kDa, respectively. In addition to the major bands, each lysate contained minor protein bands of higher apparent molecular weight. Protein bands seen in the HMW2 lysates at molecular masses of less than 120 kDa were not regularly observed and presumably represent proteolytic degradation products. Lysates of LE392 infected with the λEMBL3 cloning vector alone were non-reactive when immunologically screened with the same serum sample. Thus, the observed activity was not due to cross-reactive *E. coli* proteins or λEMBL3-encoded proteins. Furthermore, the recombinant proteins were not simply binding immunoglobulin nonspecifically, since the proteins were not reactive with the goat anti-human IgG conjugate alone, with normal rabbit sera, or with serum from a number of healthy young infants.

Representative clones expressing either the HMW1 or HMW2 recombinant proteins were characterized further. The restriction maps of the two phage types were different from each other, including the regions encoding the HMW1 and HMW2 structural genes. FIG. 5A shows restriction maps of representative recombinant phage which contained the HMW1 or HMW2 structural genes. The locations of the structural genes are indicated by the shaded bars.

HMW1 plasmid subclones were constructed by using the T7 expression plasmid T7-7 (FIG. 5A and B). HMW2 plasmid subclones also were constructed, and the results with these latter subclones were similar to those observed with the HMW1 constructs.

The approximate location and direction of transcription of the HMW1 structure gene were initially determined by using plasmid pHMW1 (FIG. 5A). This plasmid was constructed by inserting the 8.5-kb BamHI-SalI fragment from λHMW1 into PHI- and SalI-cut pT7-7. *E. coli* transformed with pHNW1 expressed an immunoreactive recombinant protein with an apparent molecular mass of 115 kDa, which was strongly inducible with IPTG. This protein was significantly smaller than the 125-kDa major protein expressed by the parent phage, indicating that it either was being expressed as a fusion protein or was truncated at the carboxy terminus.

To more precisely localize the 3' end of the structural gene, additional plasmids were constructed with progressive deletions from the 3' end of the pHMW1 construct. Plasmid pHMW1-1 was constructed by digestion of pHMW1 with PstI, isolation of the resulting 8.8-kb fragment, and religation. Plasmid pHMW1-2 was constructed by digestion of pHMW1 with HindIII, isolation of the resulting 7.5-kb fragment, and religation. E. coli transformed with either plasmid pHMW1-1 or pHMW1-2 also expressed an immunoreactive recombinant protein with an apparent molecular mass of 115 kDa. These results indicated that the 3' end of the structural gene was 5' of the HindIII site.

To more precisely localize the 5' end of the gene, plasmids pHMW1-4 and pHMW1-7 were constructed. Plasmid pHMW1-4 was constructed by cloning the 5.1-kb BamHI-HindIII fragment from λHMW1 into a pT7-7-derived plasmid containing the upstream 3.8-kb ERI-BamHI fragment. E. coli transformed with pHMW1-4 expressed an immunoreactive protein with an apparent molecular mass of approximately 160 kDa. Although protein production was inducible with IPTG, the levels of protein production in these transformants were substantially lower than those with the pHMW1-2 transformants described above. Plasmid pHMW1-7 was constructed by digesting pHMW1-4 with NdeI and SpeI. The 9.0-kbp fragment generated by this double digestion was isolated, blunt ended, and religated. E. coli transformed with pHMW1-7 also expressed an immunoreactive protein with an apparent molecular mass of 160 kDa, a protein identical in size to that expressed by the pHMW1-4 transformants. The result indicated that the initiation codon for the HMW1 structural gene was 3' of the SpeI site. DNA sequence analysis confirmed this conclusion.

As noted above, the λHMW1 phage clones expressed a major immunoreactive band of 125 kDa, whereas the HMW1 plasmid clones pHMW1-4 and pHMW1-7, which contained what was believed to be the full-length gene, expressed an immunoreactive protein of approximately 160 kDa. This size discrepancy was disconcerting. One possible explanation was that an additional gene or genes necessary for correct processing of the HMW1 gene product were deleted in the process of subcloning. To address this possibility, plasmid pHMW1-14 was constructed. This construct was generated by digesting pHMW1 with NdeI and MluI and inserting the 7.6-kbp NdeI-MluI fragment isolated from pHMW1-4. Such a construct would contain the full-length HMW1 gene as well as the DNA 3' of the HMW1 gene which was present in the original HMW1 phage. E. coli transformed with this plasmid expressed major immunoreactive proteins with apparent molecular masses of 125 and 160 kDa as well as additional degradation products. The 125- and 160-kDa bands were identical to the major and minor immunoreactive bands detected in the HMW1 phage lysates. Interestingly, the pHMW1-14 construct also expressed significant amounts of protein in the uninduced condition, a situation not observed with the earlier constructs.

The relationship between the 125- and 160-kDa proteins remains somewhat unclear. Sequence analysis, described below, reveals that the HMW1 gene would be predicted to encode a protein of 159 kDa. It is believed that the 160-kDa protein is a precursor form of the mature 125-kDa protein, with the conversion from one protein to the other being dependent on the products of the two downstream genes.

Sequence analysis of the HMW1 gene (FIG. 1) revealed a 4,608-bp open reading frame (ORF), beginning with an ATG codon at nucleotide 351 and ending with a TAG stop codon at nucleotide 4959. A putative ribosome-binding site with the sequence AGGAG begins 10 bp upstream of the putative initiation codon. Five other inframe ATG codons are located within 250 bp of the beginning of the ORF, but none of these is preceded by a typical ribosome-binding site. The 5'-flanking region of the ORF contains a series of direct tandem repeats, with the 7-bp sequence ATCTTTC repeated 16 times. These tandem repeats stop 100 bp 5' of the putative initiation codon. An 8-bp inverted repeat characteristic of a rhoindependent transcriptional terminator is present, beginning at nucleotide 4983, 25 bp 3' of the presumed translational stop. Multiple termination codons are present in all three reading frames both upstream and downstream of the ORF. The derived amino acid sequence of the protein encoded by the HMW1 gene (FIG. 2) has a molecular weight of 159,000, in good agreement with the apparent molecular weights of the proteins expressed by the HMW1-4 and HMW1-7 transformants. The derived amino acid sequence of the amino terminus does not demonstrate the characteristics of a typical signal sequence. The BamHI site used in generation of pHMW1 comprises bp 1743 through 1748 of the nucleotide sequence. The ORF downstream of the BamHI site would be predicted to encode a protein of 111 kDa, in good agreement with the 115 kDa estimated for the apparent molecular mass of the pHMW1-encoded fusion protein.

The sequence of the HMW2 gene (FIG. 3) consists of a 4,431-bp ORF, beginning with an ATG codon at nucleotide 352 and ending with a TAG stop codon at nucleotide 4783. The first 1,259 bp of the ORF of the HMW2 gene are identical to those of the HMW1 gene. Thereafter, the sequences begin to diverge but are 80% identical overall. With the exception of a single base addition at nucleotide 93 of the HMW2 sequence, the 5'-flanking regions of the HMW1 and HMW2 genes are identical for 310 bp upstream from the respective initiation codons. Thus, the HMW2 gene is preceded by the same set of tandem repeats and the same putative ribosome-binding site which lies 5' of the HMW1 gene. A putative transcriptional terminator identical to that identified 3' of the HMW1 ORF is noted, beginning at nucleotide 4804. The discrepancy in the lengths of the two genes is principally accounted for by a 186-bp gap in the HMW2 sequence, beginning at nucleotide position 3839. The derived amino acid sequence of the protein encoded by the HMW2 gene (FIG. 4) has a molecular weight of 155,000 and is 71% identical with the derived amino acid sequence of the HMW1 gene.

The derived amino acid sequences of both the HMW1 and HMW2 genes (FIGS. 2 and 4) demonstrated sequence similarity with the derived amino acid sequence of filamentous hemagglutinin of Bordetella pertussis, a surface-associated protein of this organism. The initial and optimized TFASTA scores for the HMW1-filamentous hemagglutinin sequence comparison were 87 and 186, respectively, with a word size of 2. The z score for the comparison was 45.8. The initial and optimized TFASTA scores for the HMW2-filamehtous hemagglutinin sequence comparison were 68 and 196, respectively. The z score for the latter comparison was 48.7. The magnitudes of the initial and optimized TFASTA scores and the z scores suggested that a biologically significant relationship existed between the HMW1 and HMW2 gene products and filamentous hemagglutinin. When the derived amino acid sequences of HMW1, HMW2, and filamentous hemagglutinin genes were aligned and compared, the similarities were most notable at the amino-terminal ends of the three sequences. Twelve of the first 22 amino acids in the predicted peptide sequences were identical. In additional, the sequences demonstrated a common five-amino-acid stretch, Asn-Pro-Asn-Gly-Ile, and several shorter stretches of sequence identity within the first 200 amino acids.

Example 2

To further explore the HMW1-filamentous hemagglutinin relationship, the ability of antiserum prepared against the HMW1-4 recombinant protein (rHMW1) to recognize purified filamentous hemagglutinin was assessed. The rHMW1 antiserum demonstrated ELISA reactivity with filamentous hemagglutinin in a dose-dependent manner. Preimmune rabbit serum had minimal reactivity in this assay. The rHMW1 antiserum also was examined in a Western blot assay and demonstrated weak but positive reactivity with purified filamentous hemagglutinin in this system also.

To identify the native Haemophilus protein corresponding to the HMW1 gene product and to determine the extent to which proteins antigenically related to the HMW1 cloned gene product were common among other non-typeable *H. influenzae* strains, a panel of Haemophilus strains was screened by Western blot with the rHMW1 antiserum. The antiserum recognized both a 125- and a 120-kDa protein band in the homologous strain 12, the putative mature protein products of the HMW1 and HMW2 genes, respectively.

When used to screen heterologous non-typeable *H. influenzae* strains, rHMW1 antiserum recognized high-molecular-weight proteins in 75% of 125 epidemiologically unrelated strains. In general, the antiserum reacted with one or two protein bands in the 100- to 150-kDa range in each of the heterologous strains in a pattern similar but not identical to that seen in the homologous strain.

Monoclonal antibody X3C is a murine IgG antibody directed against the filamentous hemagglutinin protein of *B. pertussis*. This antibody can inhibit the binding of *B. pertussis* cells to Chinese hamster ovary cells and HeLa cells in culture and will inhibit hemagglutination of erythrocytes by purified filamentous hemagglutinin. A Western blot assay was performed in which this monoclonal antibody was screened against the same panel of non-typeable *H. influenzae* strains discussed above. Monoclonal antibody X3C recognized both the high-molecular-weight proteins in non-typeable *H. influenzae* strain 12 which were recognized by the recombinant-protein antiserum. In addition, the monoclonal antibody recognized protein bands in a subset of heterologous non-typeable *H. influenzae* strains which were identical to those recognized by the recombinant-protein antiserum. On occasion, the filamentous hemagglutinin monoclonal antibody appeared to recognize only one of the two bands which had been recognized by the recombinant-protein antiserum. Overall, monoclonal antibody X3C recognized high-molecular-weight protein bands identical to those recognized by the rHMW1 antiserum in approximately 35% of our collection of non-typeable *H. influenzae* strains.

Example 3

Mutants deficient in expression of HMW1, MW2 or both proteins were constructed to examine the role of these proteins in bacterial adherence. The following strategy was employed. pHMW1-14 (see Example 1, FIG. 5A) was digested with BamHI and then ligated to a kanamycin cassette isolated on a 1.3-kb BamHl fragment from pUC4K. The resultant plasmid (pHMW1-17) was linearized by digestion with XbaI and transformed into non-typeable *H. influenzae* strain 12, followed by selection for kanamycin resistant colonies. Southern analysis of a series of these colonies demonstrated two populations of transformants, one with an insertion in the HMW1 structural gene and the other with an insertion in the HMW2 structural gene. One mutant from each of these classes was selected for further studies.

Mutants deficient in expression of both proteins were recovered using the following protocol. After deletion of the 2.1-kb fragment of DNA between two EcoRI sites spanning the 3'-portion of the HMW1 structural gene in pHMW-15, the kanamycin cassette from pUC4K was inserted as a 1.3-kb EcoRl fragment. The resulting plasmid (pHMW1-16) was linearized by digestion with XbI and transformed into strain 12, followed again by selection for kanamycin resistant colonies. Southern analysis of a representative sampling of these colonies demonstrated that in seven of eight cases, insertion into both the HMW1 and HMW2 loci had occurred. One such mutant was selected for further studies.

To confirm the intended phenotypes, the mutant strains were examined by Western blot analysis with a polyclonal antiserum against recombinant HMW1 protein. The parental strain expressed both the 125-kD HMW1 and the 120-kD HMW2 protein. In contrast, the HMW2$^-$ mutant failed to express the 120-kD protein, and the HMW1 mutant failed to express the 125-kD protein. The double mutant lacked expression of either protein. On the basis of whole cell lysates, outer membrane profiles, and colony morphology, the wild type strain and the mutants were otherwise identical with one another. Transmission electron microscopy demonstrated that none of the four strains expressed pili.

The capacity of wild type strain 12 to adhere to Chang epithelial cells was examined. In such assays, bacteria were inoculated into broth and allowed to grow to a density of ~$2 \times 10^9$ cfu/ml. Approximately $2 \times 10^7$ cfu were inoculated onto epithelial cell monolayers, and plates were gently centrifuged at 165×g for 5 minutes to facilitate contact between bacteria and the epithelial surface. After incubation for 30 minutes at 37° C. in 5% $CO_2$, monolayers were rinsed 5 times with PBS to remove nonadherent organisms and were treated with trypsin-EDTA (0.05% trypsin, 0.5% EDTA) in PBS to release them from the plastic support. Well contents were agitated, and dilutions were plated on solid medium to yield the number of adherent bacteria per monolayer. Percent adherence was calculated by dividing the number of adherent cfu per monolayer by the number of inoculated cfu.

As depicted in Table 1 below (the Tables appear at the end of the descriptive text), this strain adhered quite efficiently, with nearly 90% of the inoculum binding to the monolayer. Adherence by the mutant expressing HMW1 but not HMW2 (HMW2$^-$) was also quite efficient and comparable to that by the wild type strain. In contrast, attachment by the strain expressing HMW2 but deficient in expression of HMW1 (HMW1$^-$) was decreased about 15-fold relative to the wild type. Adherence by the double mutant (HMW1$^-$/HMW2$^-$) was decreased even further, approximately 50-fold compared with the wild type and approximately 3-fold compared with the HMW1 mutant. Considered together, these results suggest that both the HMW1 protein and the, HMW2 protein influence attachment to Chang epithelial cells. Interestingly, optimal adherence to this cell line appears to require HMW1 but not HMW2.

Example 4

Using the plasmids pHMW1-16 and pHMW1-17 (see Example 3) and following a scheme similar to that employed with strain 12 as described in Example 3, three non-typeable Haemoghilus strain 5 mutants were isolated, including one with the kanamycin gene inserted into the hmw1-like (designated hmw3) locus, a second with an insertion in the hmw2-like (designated hmw4) locus, and a third with insertions in both loci. As predicted, Western immunoblot analysis demonstrated that the mutant with insertion of the kanamycin cassette into the hmw1-like locus had lost expression of the HMW3 125-kD protein, while the mutant with insertion into the hmw2-like locus failed to express the HMW4 123-kD protein. The mutant with a double insertion was unable to express either of the high molecular weight proteins.

As shown in Table 1 below, wild type strain 5 demonstrated high level adherence, with almost 80% of the inoculum adhering per monolayer. Adherence by the mutant deficient in expression of the HMW2-like protein was also quite high. In contrast, adherence by the mutant unable to express the, HMW1-like protein was reduced about 5-fold relative to the wild type, and attachment by the double mutant was diminished even further (approximately 25-fold). Examination of Giemsa-stained samples confirmed these observations (not shown). Thus, the results with strain 5 corroborate the findings with strain 12 and the HMW1 and HMW2 proteins.

Example 5

To confirm an adherence function for the HMW1 and HMW2 proteins and to examine the effect of HMW1 and HMW2 independently of other *H. influenzae* surface structures, the hmw1 and the hmw2 gene clusters were introduced into *E. coli* DH5α, using plasmids pHMW1-14 and pHMW2-21, respectively. As a control, the cloning vector, pT7-7, was also transformed into *E. coli* DH5α. Western blot analysis demonstrated that *E. coli* DH5α containing the hmw1 genes expressed a 125 kDa protein, while the same strain harboring the hmw2 genes expressed a 120-kDa protein. *E. coli* DH5α containing pT7-7 failed to react with antiserum against recombinant HMW1. Transmission electron microscopy revealed no pili or other surface appendages on any of the *E. coli* strains.

Adherence by the *E. coli* strains was quantitated and compared with adherence by wild type non-typeable *H. influenzae* strain 12. As shown in Table 2 below, adherence by *E. coli* DH5α containing vector alone was less than 1% of that for strain 12. In contrast, *E. coli* DH5α harboring the hmw1 gene cluster demonstrated adherence levels comparable to those for strain 12. Adherence by *E. coli* DH5α containing the hmw2 genes was approximately 6-fold lower than attachment by strain 12 but was increased 20-fold over adherence by *E. coli* DH5α with pT7-7 alone. These results indicate that the HMW1 and HMW2 proteins are capable of independently mediating attachment to Chang conjunctival cells. These results are consistent with the results with the *H. influenzae* mutants reported in Examples 3 and 4, providing further evidence that, with Chang epithelial cells, HMW1 is a more efficient adhesin than is HMW2.

Experiments with *E. coli* HB101 harboring pT7-7, pHMW1-14, or pHMW2-21 confirmed the results obtained with the DH5α derivatives (see Table 2).

Example 6

HMW1 and HMW2 were isolated and purified from non-typeable *H. influenzae* (NTHI) strain 12 in the following manner. Non-typeable Haemophilus bacteria from frozen stock culture were streaked onto a chocolate plate and grown overnight at 37° C. in an incubator with 5% $CO_2$. 50ml starter culture of brain heart infusion (BHI) broth, supplemented with 10 µg/ml each of hemin and NAD was inoculated with growth on chocolate plate. The starter culture was grown until the optical. density (O.D.—600 nm) reached 0.6 to 0.8 and then the bacteria in the starter culture was used to inoculate six 500 ml flasks of supplemented BHI using 8 to 10 ml per flask. The bacteria were grown in 500 ml flasks for an additional 5 to 6 hours at which time the O.D. was 1.5 or greater. Cultures were centrifuged at 10,000 rpm for 10 minutes.

Bacterial pellets were resuspended in a total volume of 250 ml of an extraction solution comprising 0.5M NaCl, 0.01M $Na_2EDTA$, 0.01M Tris 50 µM 1,10-phenanthroline, pH 7.5. The cells were not sonicated or otherwise disrupted. The resuspended cells were allowed to sit on ice at 0° C. for 60 minutes. The resuspended cells were centrifuged at 10,000 rpm for 10 minutes at 4° C. to remove the majority of intact cells and cellular debris. The supernatant was collected and centrifuged at 100,000×g for 60 minutes at 4° C. The supernatant again was collected and dialyzed overnight at 4° C. against 0.01M sodium phosphate, pH 6.0.

The sample was centrifuged at 10,000 rpm for 10 minutes at 4° C. to remove insoluble debris precipitated from solution during dialysis. The supernatant was applied to a 10 ml CM Sepharose column which has been pre-equilibrated with 0.01M sodium phosphate, pH 6. Following application to this column, the column was washed with 0.01M sodium phosphate. Proteins were elevated from the column with a 0–0.5M KCl gradient in 0.01M Na phosphate, pH 6 and fractions were collected for gel examination. Coomassie gels of column fractions were carried out to identify those fractions containing high molecular weight proteins. The fractions containing high molecular weight proteins were pooled and concentrated to a 1 to 3 ml volume in preparation for application of sample to gel filtration column.

A Sepharose CL-4B gel filtration column was equilibrated with phosphate-buffered saline, pH 7.5. The concentrated high molecular weight protein sample was applied to the gel filtration column and column fractions were collected. Coomassie gels were performed on the column fractions to identify those containing high molecular weight proteins. The column fractions containing high molecular weight proteins were pooled.

The proteins were tested to determine whether they would protect against experimental otitis media caused by the homologous strain.

Chinchillas received three monthly subcutaneous injections with 40 µg of an HMW1-HMW2 protein mixture in Freund's adjuvant. One month after the last injection, the animals were challenged by intrabullar inoculation with 300 cfu of NTHI,strain 12.

Infection developed in 5 of 5 control animals versus 5 of 10 immunized animals. Among infected animals, geometric mean bacterial counts in middle ear fluid 7 days post-challenge were $7.4 \times 10^6$ in control animals verus $1.3 \times 10^5$ in immunized animals.

Serum antibody titres following immunization were comparable in uninfected and infected animals. However, infection in immunized animals was uniformly associated with the appearance of bacteria down-regulated in expression of the HMW proteins, suggesting bacterial selection in response to immunologic pressure.

Although this data shows that protection following immunization was not complete, this data suggests the HMW adhesin proteins are potentially important protective antigens which may comprise one component of a multi-component NTHI vaccine.

Example 7

A number of synthetic peptides were derived from HMW1. Antisera then was raised to these peptides. The anti-peptide antisera to peptide HMW1-P5 was shown to recognize HMW1. Peptide HMW1-P5 covers amino acids 1453 to 1481 of HMW1, has the sequence VDEVIEAKRILEKVKDLSDEEREALAKLG (SEQ ID NO:9), and represents bases 1498 to 1576 in FIG. 10.

This finding demonstrates that the DNA sequence and the derived protein is being interpreted in the correct reading frame and that peptides derived from the sequence can be produced which will be immunogenic.

SUMMARY OF DISCLOSURE

In summary of this disclosure, the present invention provides high molecular weight proteins of non-typeable Haemophilus, genes coding for the same and vaccines incorporating such proteins. Modifications are possible within the scope of this invention.

TABLE 1

Effect of mutation of high molecular weight proteins on adherence to Chang epithelial cells by nontypable H. influenzae

| | ADHERENCE* | |
|---|---|---|
| Strain | % inoculum | relative to wild type† |
| Strain 12 derivatives | | |
| wild type | 87.7 ± 5.9 | 100.0 ± 6.7 |
| HMW1-mutant | 6.0 ± 0.9 | 6.8 ± 1.0 |
| HMW2-mutant | 89.9 ± 10.8 | 102.5 ± 12.3 |

TABLE 1-continued

Effect of mutation of high molecular weight proteins on adherence to Chang epithelial cells by nontypable H. influenzae

| | ADHERENCE* | |
|---|---|---|
| Strain | % inoculum | relative to wild type† |
| HMW1-/HMW2-mutant Strain 5 derivatives | 2.0 ± 0.3 | 2.3 ± 0.3 |
| wild type | 78.7 ± 3.2 | 100.0 ± 4.1 |
| HMW1-like mutant | 15.7 ± 2.6 | 19.9 ± 3.3 |
| HMW2-like mutant | 103.7 ± 14.0 | 131.7 ± 17.8 |
| double mutant | 3.5 ± 0.6 | 4.4 ± 0.8 |

*Numbers represent mean (± standard error of the mean) of measurements in triplicate or quadruplicate from representative experiments.
†Adherence values for strain 12 derivatives are relative to strain 12 wild type; values for strain 5 derivatives are relative to strain 5 wild type.

TABLE 2

Adherence by E. coli DH5α and HB101 harboring hmw1 or hmw2 gene clusters

| Strain* | Adherence relative to H. influenzae strain 12† |
|---|---|
| DH5α (pT7-7) | 0.7 ± 0.02 |
| DH5α (pHMW1-14) | 114.2 ± 15.9 |
| DH5α (pHMW2-21) | 14.0 ± 3.7 |
| HB101 (pT7-7) | 1.2 ± 0.5 |
| HB101 (pHMW1-14) | 93.6 ± 15.8 |
| HB101 (pHMW2-21) | 3.6 ± 0.9 |

*The plasmid pHMW1-14 contains the hmw1 gene cluster, while pHMW2-21 contains the hmw2 gene cluster; pT7-7 is the cloning vector used in these constructs.
†Numbers represent the mean (± standard error of the mean) of measurements made in triplicate from representative experiments.

What I claim is:

1. An isolated and purified gene which encodes a high molecular weight protein having the amino acid sequence of SEQ ID NO: 4.

2. The gene of claim 1 having the DNA sequence of SEQ ID NO: 3.

3. An isolated and purified gene cluster of a non-typeable Haemophilus strain comprising the sequence of SEQ ID No: 6.

* * * * *

```
                            SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
         (A) LENGTH: 5116 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:1:

ACAGCGTTCT CTTAATACTA GTACAAACCC ACAATAAAAT ATGACAAACA ACAATTACAA      60

CACCTTTTTT GCAGTCTATA TGCAAATATT TTAAAAAATA GTATAAATCC GCCATATAAA    120

ATGGTATAAT CTTTCATCTT TCATCTTTCA TCTTTCATCT TTCATCTTTC ATCTTTCATC    180

TTTCATCTTT CATCTTTCAT CTTTCATCTT TCATCTTTCA TCTTTCATCT TTCATCTTTC    240

ACATGCCCTG ATGAACCGAG GGAAGGGAGG GAGGGGCAAG AATGAAGAGG GAGCTGAACG    300

AACGCAAATG ATAAAGTAAT TTAATTGTTC AACTAACCTT AGGAGAAAAT ATGAACAAGC    360
```

-continued

| | |
|---|---|
| TATATCGTCT CAAATTCAGC AAACGCCTGA ATGCTTTGGT TGCTGTGTCT GAATTGGCAC | 420 |
| GGGGTTGTGA CCATTCCACA GAAAAGGCA GCGAAAAACC TGCTCGCATG AAAGTGCGTC | 480 |
| ACTTAGCGTT AAAGCCACTT TCCGCTATGT TACTATCTTT AGGTGTAACA TCTATTCCAC | 540 |
| AATCTGTTTT AGCAAGCGGC TTACAAGGAA TGGATGTAGT ACACGGCACA GCCACTATGC | 600 |
| AAGTAGATGG TAATAAAACC ATTATCCGCA ACAGTGTTGA CGATATCATT AATTGGAAAC | 660 |
| AATTTAACAT CGACCAAAAT GAAATGGTGC AGTTTTTACA AGAAAACAAC AACTCCGCCG | 720 |
| TATTCAACCG TGTTACATCT AACCAAATCT CCCAATTAAA AGGGATTTTA GATTCTAACG | 780 |
| GACAAGTCTT TTTAATCAAC CCAAATGGTA TCACAATAGG TAAAGACGCA ATTATTAACA | 840 |
| CTAATGGCTT TACGGCTTCT ACGCTAGACA TTTCTAACGA AAACATCAAG GCGCGTAATT | 900 |
| TCACCTTCGA GCAAACCAAA GATAAAGCGC TCGCTGAAAT TGTGAATCAC GGTTTAATTA | 960 |
| CTGTCGGTAA AGACGGCAGT GTAAATCTTA TTGGTGGCAA AGTGAAAAAC GAGGGTGTGA | 1020 |
| TTAGCGTAAA TGGTGGCAGC ATTTCTTTAC TCGCAGGGCA AAAAATCACC ATCAGCGATA | 1080 |
| TAATAAACCC AACCATTACT TACAGCATTG CCGCGCCTGA AAATGAAGCG GTCAATCTGG | 1140 |
| GCGATATTTT TGCCAAAGGC GGTAACATTA ATGTCCGTGC TGCCACTATT CGAAACCAAG | 1200 |
| GTAAACTTTC TGCTGATTCT GTAAGCAAAG ATAAAAGCGG CAATATTGTT CTTTCCGCCA | 1260 |
| AAGAGGGTGA AGCGGAAATT GGCGGTGTAA TTTCCGCTCA AAATCAGCAA GCTAAAGGCG | 1320 |
| GCAAGCTGAT GATTACAGGC GATAAAGTCA CATTAAAAAC AGGTGCAGTT ATCGACCTTT | 1380 |
| CAGGTAAAGA AGGGGAGAA ACTTACCTTG GCGGTGACGA GCGCGGCGAA GGTAAAAAGG | 1440 |
| GCATTCAATT AGCAAAGAAA ACCTCTTTAG AAAAAGGCTC AACCATCAAT GTATCAGGCA | 1500 |
| AAGAAAAAGG CGGACGCGCT ATTGTGTGGG GCGATATTGC GTTAATTGAC GGCAATATTA | 1560 |
| ACGCTCAAGG TAGTGGTGAT ATCGCTAAAA CCGGTGGTTT TGTGGAGACG TCGGGGCATG | 1620 |
| ATTTATTCAT CAAAGACAAT GCAATTGTTG ACGCCAAAGA GTGGTTGTTA GACCCGGATA | 1680 |
| ATGTATCTAT TAATGCAGAA ACAGCAGGAC GCAGCAATAC TTCAGAAGAC GATGAATACA | 1740 |
| CGGGATCCGG GAATAGTGCC AGCACCCCAA AACGAAACAA AGAAAAGACA ACATTAACAA | 1800 |
| ACACAACTCT TGAGAGTATA CTAAAAAAAG GTACCTTTGT TAACATCACT GCTAATCAAC | 1860 |
| GCATCTATGT CAATAGCTCC ATTAATTTAT CCAATGGCAG CTTAACTCTT TGGAGTGAGG | 1920 |
| GTCGGAGCGG TGGCGGCGTT GAGATTAACA ACGATATTAC CACCGGTGAT GATACCAGAG | 1980 |
| GTGCAAACTT AACAATTTAC TCAGGCGGCT GGGTTGATGT TCATAAAAAT ATCTCACTCG | 2040 |
| GGGCGCAAGG TAACATAAAC ATTACAGCTA AACAAGATAT CGCCTTTGAG AAAGGAAGCA | 2100 |
| ACCAAGTCAT TACAGGTCAA GGGACTATTA CCTCAGGCAA TCAAAAAGGT TTTAGATTTA | 2160 |
| ATAATGTCTC TCTAAACGGC ACTGGCAGCG GACTGCAATT CACCACTAAA AGAACCAATA | 2220 |
| AATACGCTAT CACAAATAAA TTTGAAGGGA CTTTAAATAT TTCAGGGAAA GTGAACATCT | 2280 |
| CAATGGTTTT ACCTAAAAAT GAAAGTGGAT ATGATAAATT CAAAGGACGC ACTTACTGGA | 2340 |
| ATTTAACCTC CTTAAATGTT TCCGAGAGTG GCGAGTTTAA CCTCACTATT GACTCCAGAG | 2400 |
| GAAGCGATAG TGCAGGCACA CTTACCCAGC CTTATAATTT AAACGGTATA TCATTCAACA | 2460 |
| AAGACACTAC CTTTAATGTT GAACGAAATG CAAGAGTCAA CTTTGACATC AAGGCACCAA | 2520 |
| TAGGGATAAA TAAGTATTCT AGTTTGAATT ACGCATCATT TAATGAAAC ATTTCAGTTT | 2580 |
| CGGGAGGGGG GAGTGTTGAT TTCACACTTC TCGCCTCATC CTCTAACGTC CAAACCCCCG | 2640 |
| GTGTAGTTAT AAATTCTAAA TACTTTAATG TTTCAACAGG GTCAAGTTTA AGATTTAAAA | 2700 |
| CTTCAGGCTC AACAAAAACT GGCTTCTCAA TAGAGAAAGA TTTAACTTTA AATGCCACCG | 2760 |

-continued

```
GAGGCAACAT AACACTTTTG CAAGTTGAAG GCACCGATGG AATGATTGGT AAAGGCATTG    2820

TAGCCAAAAA AAACATAACC TTTGAAGGAG GTAACATCAC CTTTGGCTCC AGGAAAGCCG    2880

TAACAGAAAT CGAAGGCAAT GTTACTATCA ATAACAACGC TAACGTCACT CTTATCGGTT    2940

CGGATTTTGA CAACCATCAA AAACCTTTAA CTATTAAAAA AGATGTCATC ATTAATAGCG    3000

GCAACCTTAC CGCTGGAGGC AATATTGTCA ATATAGCCGG AAATCTTACC GTTGAAAGTA    3060

ACGCTAATTT CAAAGCTATC ACAAATTTCA CTTTTAATGT AGGCGGCTTG TTTGACAACA    3120

AAGGCAATTC AAATATTTCC ATTGCCAAAG GAGGGGCTCG CTTTAAAGAC ATTGATAATT    3180

CCAAGAATTT AAGCATCACC ACCAACTCCA GCTCCACTTA CCGCACTATT ATAAGCGGCA    3240

ATATAACCAA TAAAAACGGT GATTTAAATA TTACGAACGA AGGTAGTGAT ACTGAAATGC    3300

AAATTGGCGG CGATGTCTCG CAAAAAGAAG GTAATCTCAC GATTTCTTCT GACAAAATCA    3360

ATATTACCAA ACAGATAACA ATCAAGGCAG GTGTTGATGG GGAGAATTCC GATTCAGACG    3420

CGACAAACAA TGCCAATCTA ACCATTAAAA CCAAAGAATT GAAATTAACG CAAGACCTAA    3480

ATATTTCAGG TTTCAATAAA GCAGAGATTA CAGCTAAAGA TGGTAGTGAT TTAACTATTG    3540

GTAACACCAA TAGTGCTGAT GGTACTAATG CCAAAAAAGT AACCTTTAAC CAGGTTAAAG    3600

ATTCAAAAAT CTCTGCTGAC GGTCACAAGG TGACACTACA CAGCAAAGTG GAAACATCCG    3660

GTAGTAATAA CAACACTGAA GATAGCAGTG ACAATAATGC CGGCTTAACT ATCGATGCAA    3720

AAAATGTAAC AGTAAACAAC AATATTACTT CTCACAAAGC AGTGAGCATC TCTGCGACAA    3780

GTGGAGAAAT TACCACTAAA ACAGGTACAA CCATTAACGC AACCACTGGT AACGTGGAGA    3840

TAACCGCTCA AACAGGTAGT ATCCTAGGTG GAATTGAGTC CAGCTCTGGC TCTGTAACAC    3900

TTACTGCAAC CGAGGGCGCT CTTGCTGTAA GCAATATTTC GGGCAACACC GTTACTGTTA    3960

CTGCAAATAG CGGTGCATTA ACCACTTTGG CAGGCTCTAC AATTAAAGGA ACCGAGAGTG    4020

TAACCACTTC AAGTCAATCA GGCGATATCG GCGGTACGAT TTCTGGTGGC ACAGTAGAGG    4080

TTAAAGCAAC CGAAAGTTTA ACCACTCAAT CCAATTCAAA AATTAAAGCA ACAACAGGCG    4140

AGGCTAACGT AACAAGTGCA ACAGGTACAA TTGGTGGTAC GATTTCCGGT AATACGGTAA    4200

ATGTTACGGC AAACGCTGGC GATTTAACAG TTGGGAATGG CGCAGAAATT AATGCGACAG    4260

AAGGAGCTGC AACCTTAACT ACATCATCGG GCAAATTAAC TACCGAAGCT AGTTCACACA    4320

TTACTTCAGC CAAGGGTCAG GTAAATCTTT CAGCTCAGGA TGGTAGCGTT GCAGGAAGTA    4380

TTAATGCCGC CAATGTGACA CTAAATACTA CAGGCACTTT AACTACCGTG AAGGGTTCAA    4440

ACATTAATGC AACCAGCGGT ACCTTGGTTA TTAACGCAAA AGACGCTGAG CTAAATGGCG    4500

CAGCATTGGG TAACCACACA GTGGTAAATG CAACCAACGC AAATGGCTCC GGCAGCGTAA    4560

TCGCGACAAC CTCAAGCAGA GTGAACATCA CTGGGGATTT AATCACAATA AATGGATTAA    4620

ATATCATTTC AAAAAACGGT ATAAACACCG TACTGTTAAA AGGCGTTAAA ATTGATGTGA    4680

AATACATTCA ACCGGGTATA GCAAGCGTAG ATGAAGTAAT TGAAGCGAAA CGCATCCTTG    4740

AGAAGGTAAA AGATTTATCT GATGAAGAAA GAGAAGCGTT AGCTAAACTT GGAGTAAGTG    4800

CTGTACGTTT TATTGAGCCA AATAATACAA TTACAGTCGA TACACAAAAT GAATTTGCAA    4860

CCAGACCATT AAGTCGAATA GTGATTTCTG AAGGCAGGGC GTGTTTCTCA ACAGTGATG    4920

GCGCGACGGT GTGCGTTAAT ATCGCTGATA ACGGGCGGTA GCGGTCAGTA ATTGACAAGG    4980

TAGATTTCAT CCTGCAATGA AGTCATTTTA TTTTCGTATT ATTTACTGTG TGGGTTAAAG    5040

TTCAGTACGG GCTTTACCCA TCTTGTAAAA AATTACGGAG AATACAATAA AGTATTTTA    5100

ACAGGTTATT ATTATG                                                   5116
```

(2) INFORMATION FOR SEQ ID NO:2:

(i) SEQUENCE CHARACTERISTICS:
        (A) LENGTH: 1536 amino acids
        (B) TYPE: amino acid
        (C) STRANDEDNESS: single
        (D) TOPOLOGY: linear (ii) MOLECULE TYPE:

(xi) SEQUENCE DESCRIPTION: SEQ ID NO:2:

```
Met Asn Lys Ile Tyr Arg Leu Lys Phe Ser Lys Arg Leu Asn Ala Leu
  1               5                  10                  15

Val Ala Val Ser Glu Leu Ala Arg Gly Cys Asp His Ser Thr Glu Lys
             20                  25                  30

Gly Ser Glu Lys Pro Ala Arg Met Lys Val Arg His Leu Ala Leu Lys
         35                  40                  45

Pro Leu Ser Ala Met Leu Leu Ser Leu Gly Val Thr Ser Ile Pro Gln
 50                  55                  60

Ser Val Leu Ala Ser Gly Leu Gln Gly Met Asp Val Val His Gly Thr
 65                  70                  75                  80

Ala Thr Met Gln Val Asp Gly Asn Lys Thr Ile Ile Arg Asn Ser Val
                 85                  90                  95

Asp Ala Ile Ile Asn Trp Lys Gln Phe Asn Ile Asp Gln Asn Glu Met
                100                 105                 110

Val Gln Phe Leu Gln Glu Asn Asn Ser Ala Val Phe Asn Arg Val
             115                 120                 125

Thr Ser Asn Gln Ile Ser Gln Leu Lys Gly Ile Leu Asp Ser Asn Gly
            130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Phe Glu Gln Thr Lys Asp Lys
                180                 185                 190

Ala Leu Ala Glu Ile Val Asn His Gly Leu Ile Thr Val Gly Lys Asp
            195                 200                 205

Gly Ser Val Asn Leu Ile Gly Gly Lys Val Lys Asn Glu Gly Val Ile
        210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Val Asn Leu Gly Asp Ile Phe Ala Lys Gly Gly Asn
            260                 265                 270

Ile Asn Val Arg Ala Ala Thr Ile Arg Asn Gln Gly Lys Leu Ser Ala
        275                 280                 285

Asp Ser Val Ser Lys Asp Lys Ser Gly Asn Ile Val Leu Ser Ala Lys
    290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
                325                 330                 335

Thr Gly Ala Val Ile Asp Leu Ser Gly Lys Glu Gly Gly Glu Thr Tyr
            340                 345                 350

Leu Gly Gly Asp Glu Arg Gly Glu Gly Lys Asn Gly Ile Gln Leu Ala
```

```
                    355                 360                 365
Lys Lys Thr Ser Leu Glu Lys Gly Ser Thr Ile Asn Val Ser Gly Lys
    370                 375                 380

Glu Lys Gly Gly Arg Ala Ile Val Trp Gly Asp Ile Ala Leu Ile Asp
385                 390                 395                 400

Gly Asn Ile Asn Ala Gln Gly Ser Gly Asp Ile Ala Lys Thr Gly Gly
                405                 410                 415

Phe Val Glu Thr Ser Gly His Asp Leu Phe Ile Lys Asp Asn Ala Ile
            420                 425                 430

Val Asp Ala Lys Glu Trp Leu Leu Asp Phe Asp Asn Val Ser Ile Asn
        435                 440                 445

Ala Glu Thr Ala Gly Arg Ser Asn Thr Ser Glu Asp Glu Tyr Thr
    450                 455                 460

Gly Ser Gly Asn Ser Ala Ser Thr Pro Lys Arg Asn Lys Glu Lys Thr
465                 470                 475                 480

Thr Leu Thr Asn Thr Thr Leu Glu Ser Ile Leu Lys Lys Gly Thr Phe
                485                 490                 495

Val Asn Ile Thr Ala Asn Gln Arg Ile Tyr Val Asn Ser Ser Ile Asn
                500                 505                 510

Leu Ser Asn Gly Ser Leu Thr Leu Trp Ser Glu Gly Arg Ser Gly Gly
            515                 520                 525

Gly Val Glu Ile Asn Asn Asp Ile Thr Thr Gly Asp Asp Thr Arg Gly
        530                 535                 540

Ala Asn Leu Thr Ile Tyr Ser Gly Gly Trp Val Asp Val His Lys Asn
545                 550                 555                 560

Ile Ser Leu Gly Ala Gln Gly Asn Ile Asn Ile Thr Ala Lys Gln Asp
                565                 570                 575

Ile Ala Phe Glu Lys Gly Ser Asn Gln Val Ile Thr Gly Gln Gly Thr
            580                 585                 590

Ile Thr Ser Gly Asn Gln Lys Gly Phe Arg Phe Asn Asn Val Ser Leu
        595                 600                 605

Asn Gly Thr Gly Ser Gly Leu Gln Phe Thr Thr Lys Arg Thr Asn Lys
    610                 615                 620

Tyr Ala Ile Thr Asn Lys Phe Glu Gly Thr Leu Asn Ile Ser Gly Lys
625                 630                 635                 640

Val Asn Ile Ser Met Val Leu Pro Lys Asn Glu Ser Gly Tyr Asp Lys
                645                 650                 655

Phe Lys Gly Arg Thr Tyr Trp Asn Leu Thr Ser Leu Asn Val Ser Glu
            660                 665                 670

Ser Gly Glu Phe Asn Leu Thr Ile Asp Ser Arg Gly Ser Asp Ser Ala
        675                 680                 685

Gly Thr Leu Thr Gln Pro Tyr Asn Leu Asn Gly Ile Ser Phe Asn Lys
    690                 695                 700

Asp Thr Thr Phe Asn Val Glu Arg Asn Ala Arg Val Asn Phe Asp Ile
705                 710                 715                 720

Lys Ala Pro Ile Gly Ile Asn Lys Tyr Ser Ser Leu Asn Tyr Ala Ser
                725                 730                 735

Phe Asn Gly Asn Ile Ser Val Ser Gly Gly Ser Val Asp Phe Thr
            740                 745                 750

Leu Leu Ala Ser Ser Ser Asn Val Gln Thr Pro Gly Val Val Ile Asn
        755                 760                 765

Ser Lys Tyr Phe Asn Val Ser Thr Gly Ser Ser Leu Arg Phe Lys Thr
    770                 775                 780
```

-continued

```
Ser Gly Ser Thr Lys Thr Gly Phe Ser Ile Glu Lys Asp Leu Thr Leu
785                 790                 795                 800

Asn Ala Thr Gly Gly Asn Ile Thr Leu Leu Gln Val Glu Gly Thr Asp
            805                 810                 815

Gly Met Ile Gly Lys Gly Ile Val Ala Lys Lys Asn Ile Thr Phe Glu
            820                 825                 830

Gly Gly Asn Ile Thr Phe Gly Ser Arg Lys Ala Val Thr Glu Ile Glu
            835                 840                 845

Gly Asn Val Thr Ile Asn Asn Asn Ala Asn Val Thr Leu Ile Gly Ser
850                 855                 860

Asp Phe Asp Asn His Gln Lys Pro Leu Thr Ile Lys Lys Asp Val Ile
865                 870                 875                 880

Ile Asn Ser Gly Asn Leu Thr Ala Gly Gly Asn Ile Val Asn Ile Ala
            885                 890                 895

Gly Asn Leu Thr Val Glu Ser Asn Ala Asn Phe Lys Ala Ile Thr Asn
            900                 905                 910

Phe Thr Phe Asn Val Gly Gly Leu Phe Asp Asn Lys Gly Asn Ser Asn
            915                 920                 925

Ile Ser Ile Ala Lys Gly Gly Ala Arg Phe Lys Asp Ile Asp Asn Ser
            930                 935                 940

Lys Asn Leu Ser Ile Thr Thr Asn Ser Ser Thr Tyr Arg Thr Ile
945                 950                 955                 960

Ile Ser Gly Asn Ile Thr Asn Lys Asn Gly Asp Leu Asn Ile Thr Asn
            965                 970                 975

Glu Gly Ser Asp Thr Glu Met Gln Ile Gly Asp Val Ser Gln Lys
            980                 985                 990

Glu Gly Asn Leu Thr Ile Ser Ser Asp Lys Ile Asn Ile Thr Lys Gln
            995                 1000                1005

Ile Thr Ile Lys Ala Gly Val Asp Gly Glu Asn Ser Asp Ser Asp Ala
        1010                1015                1020

Thr Asn Asn Ala Asn Leu Thr Ile Lys Thr Lys Glu Leu Lys Leu Thr
1025                1030                1035                1040

Gln Asp Leu Asn Ile Ser Gly Phe Asn Lys Ala Glu Ile Thr Ala Lys
            1045                1050                1055

Asp Gly Ser Asp Leu Thr Ile Gly Asn Thr Asn Ser Ala Asp Gly Thr
        1060                1065                1070

Asn Ala Lys Lys Val Thr Phe Asn Gln Val Lys Asp Ser Lys Ile Ser
        1075                1080                1085

Ala Asp Gly His Lys Val Thr Leu His Ser Lys Val Glu Thr Ser Gly
        1090                1095                1100

Ser Asn Asn Asn Thr Glu Asp Ser Ser Asp Asn Asn Ala Gly Leu Thr
1105                1110                1115                1120

Ile Asp Ala Lys Asn Val Thr Val Asn Asn Ile Thr Ser His Lys
        1125                1130                1135

Ala Val Ser Ile Ser Ala Thr Ser Gly Glu Ile Thr Thr Lys Thr Gly
        1140                1145                1150

Thr Thr Ile Asn Ala Thr Thr Gly Asn Val Glu Ile Thr Ala Gln Thr
        1155                1160                1165

Gly Ser Ile Leu Gly Gly Ile Glu Ser Ser Ser Gly Ser Val Thr Leu
        1170                1175                1180

Thr Ala Thr Glu Gly Ala Leu Ala Val Ser Asn Ile Ser Gly Asn Thr
1185                1190                1195                1200

Val Thr Val Thr Ala Asn Ser Gly Ala Leu Thr Thr Leu Ala Gly Ser
        1205                1210                1215
```

```
Thr Ile Lys Gly Thr Glu Ser Val Thr Thr Ser Ser Gln Ser Gly Asp
        1220                1225                1230

Ile Gly Gly Thr Ile Ser Gly Gly Thr Val Glu Val Lys Ala Thr Glu
        1235                1240                1245

Ser Leu Thr Thr Gln Ser Asn Ser Lys Ile Lys Ala Thr Thr Gly Glu
        1250                1255                1260

Ala Asn Val Thr Ser Ala Thr Gly Thr Ile Gly Gly Thr Ile Ser Gly
1265                1270                1275                1280

Asn Thr Val Asn Val Thr Ala Asn Ala Gly Asp Leu Thr Val Gly Asn
        1285                1290                1295

Gly Ala Glu Ile Asn Ala Thr Glu Gly Ala Ala Thr Leu Thr Thr Ser
        1300                1305                1310

Ser Gly Lys Leu Thr Thr Glu Ala Ser Ser His Ile Thr Ser Ala Lys
        1315                1320                1325

Gly Gln Val Asn Leu Ser Ala Gln Asp Gly Ser Val Ala Gly Ser Ile
        1330                1335                1340

Asn Ala Ala Asn Val Thr Leu Asn Thr Thr Gly Thr Leu Thr Thr Val
1345                1350                1355                1360

Lys Gly Ser Asn Ile Asn Ala Thr Ser Gly Thr Leu Val Ile Asn Ala
        1365                1370                1375

Lys Asp Ala Glu Leu Asn Gly Ala Ala Leu Gly Asn His Thr Val Val
        1380                1385                1390

Asn Ala Thr Asn Ala Asn Gly Ser Gly Ser Val Ile Ala Thr Thr Ser
        1395                1400                1405

Ser Arg Val Asn Ile Thr Gly Asp Leu Ile Thr Ile Asn Gly Leu Asn
        1410                1415                1420

Ile Ile Ser Lys Asn Gly Ile Asn Thr Val Leu Leu Lys Gly Val Lys
1425                1430                1435                1440

Ile Asp Val Lys Tyr Ile Gln Pro Gly Ile Ala Ser Val Asp Glu Val
        1445                1450                1455

Ile Glu Ala Lys Arg Ile Leu Glu Lys Val Lys Asp Leu Ser Asp Glu
        1460                1465                1470

Glu Arg Glu Ala Leu Ala Lys Leu Gly Val Ser Ala Val Arg Phe Ile
        1475                1480                1485

Glu Pro Asn Asn Thr Ile Thr Val Asp Thr Gln Asn Glu Phe Ala Thr
        1490                1495                1500

Arg Pro Leu Ser Arg Ile Val Ile Ser Glu Gly Arg Ala Cys Phe Ser
1505                1510                1515                1520

Asn Ser Asp Gly Ala Thr Val Cys Val Asn Ile Ala Asp Asn Gly Arg
        1525                1530                1535
```

(2) INFORMATION FOR SEQ ID NO:3:

(i) SEQUENCE CHARACTERISTICS:
        (A) LENGTH: 4937 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
TAAATATACA AGATAATAAA AATAAATCAA GATTTTGTG ATGACAAACA ACAATTACAA      60

CACCTTTTTT GCAGTCTATA TGCAAATATT TTAAAAAAAT AGTATAAATC CGCCATATAA     120

AATGGTATAA TCTTTCATCT TTCATCTTTA ATCTTTCATC TTTCATCTTT CATCTTTCAT     180
```

```
CTTTCATCTT TCATCTTTCA TCTTTCATCT TTCATCTTTC ATCTTTCATC TTTCATCTTT      240

CACATGAAAT GATGAACCGA GGGAAGGGAG GGAGGGGCAA GAATGAAGAG GGAGCTGAAC      300

GAACGCAAAT GATAAAGTAA TTTAATTGTT CAACTAACCT TAGGAGAAAA TATGAACAAG      360

ATATATCGTC TCAAATTCAG CAAACGCCTG AATGCTTTGG TTGCTGTGTC TGAATTGGCA      420

CGGGGTTGTG ACCATTCCAC AGAAAAAGGC TTCCGCTATG TTACTATCTT TAGGTGTAAC      480

CACTTAGCGT TAAAGCCACT TTCCGCTATG TTACTATCTT TAGGTGTAAC ATCTATTCCA      540

CAATCTGTTT TAGCAAGCGG CTTACAAGGA ATGGATGTAG TACACGGCAC AGCCACTATG      600

CAAGTAGATG GTAATAAAAC CATTATCCGC AACAGTGTTG ACGCTATCAT TAATTGGAAA      660

CAATTTAACA TCGACCAAAA TGAAATGGTG CAGTTTTTAC AAGAAAACAA CAACTCCGCC      720

GTATTCAACC GTGTTACATC TAACCAAATC TCCCAATTAA AAGGGATTTT AGATTCTAAC      780

GGACAAGTCT TTTTAATCAA CCCAAATGGT ATCACAATAG GTAAAGACGC AATTATTAAC      840

ACTAATGGCT TTACGGCTTC TACGCTAGAC ATTTCTAACG AAAACATCAA GGCGCGTAAT      900

TTCACCTTCG AGCAAACCAA AGATAAAGCG CTCGCTGAAA TTGTGAATCA CGGTTTAATT      960

ACTGTCGGTA AAGACGGCAG TGTAAATCTT ATTGGTGGCA AAGTGAAAAA CGAGGGTGTG     1020

ATTAGCGTAA ATGGTGGCAG CATTTCTTTA CTCGCAGGGC AAAAAATCAC CATCAGCGAT     1080

ATAATAAACC CAACCATTAC TTACAGCATT GCCGCGCCTG AAAATGAAGC GGTCAATCTG     1140

GGCGATATTT TTGCCAAAGG CGGTAACATT AATGTCCGTG CTGCCACTAT TCGAAACCAA     1200

GGTAAACTTT CTGCTGATTC TGTAAGCAAA GATAAAGCG GCAATATTGT TCTTTCCGCC      1260

AAAGAGGGTG AAGCGGAAAT TGGCGGTGTA ATTTCCGCTC AAAATCAGCA AGCTAAAGGC     1320

GGCAAGCTGA TGATTACAGG CGATAAAGTC ACATTAAAAA CAGGTGCAGT TATCGACCTT     1380

TCAGGTAAAG AAGGGGAGA AACTTACCTT GGCGGTGACG AGCGCGGCGA AGGTAAAAAC      1440

GGCATTCAAT TAGCAAAGAA AACCTCTTTA GAAAAAGGCT CAACCATCAA TGTATCAGGC     1500

AAAGAAAAAG GCGGACGCGC TATTGTGTGG GGCGATATTG CGTTAATTGA CGGCAATATT     1560

AACGCTCAAG GTAGTGGTGA TATCGCTAAA ACCGGTGGTT TTGTGGAGAC ATCGGGGCAT     1620

TATTTATCCA TTGACAGCAA TGCAATTGTT AAAACAAAAG AGTGGTTGCT AGACCCTGAT     1680

GATGTAACAA TTGAAGCCGA AGACCCCCTT CGCAATAATA CCGGTATAAA TGATGAATTC     1740

CCAACAGGCA CCGGTGAAGC AAGCGACCCT AAAAAAAATA GCGAACTCAA AACAACGCTA     1800

ACCAATACAA CTATTTCAAA TTATCTGAAA AACGCCTGGA CAATGAATAT AACGGCATCA     1860

AGAAAACTTA CCGTTAATAG CTCAATCAAC ATCGGAAGCA ACTCCCACTT AATTCTCCAT     1920

AGTAAAGGTC AGCGTGGCGG AGGCGTTCAG ATTGATGGAG ATATTACTTC TAAAGGCGGA     1980

AATTTAACCA TTTATTCTGG CGGATGGGTT GATGTTCATA AAAATATTAC GCTTGATCAG     2040

GGTTTTTTAA ATATTACCGC CGCTTCCGTA GCTTTTGAAG GTGGAAATAA CAAAGCACGC     2100

GACGCGGCAA ATGCTAAAAT TGTCGCCCAG GGCACTGTAA CCATTACAGG AGAGGGAAAA     2160

GATTTCAGGG CTAACAACGT ATCTTTAAAC GGAACGGGTA AAGGTCTGAA TATCATTTCA     2220

TCAGTGAATA ATTTAACCCA CAATCTTAGT GGCACAATTA ACATATCTGG GAATATAACA     2280

ATTAACCAAA CTACGAGAAA GAACACCTCG TATTGGCAAA CCAGCCATGA TTCGCACTGG     2340

AACGTCAGTG CTCTTAATCT AGAGACAGGC GCAAATTTTA CCTTTATTAA ATACATTTCA     2400

AGCAATAGCA AAGGCTTAAC AACACAGTAT AGAAGCTCTG CAGGGGTGAA TTTTAACGGC     2460

GTAAATGCA ACATGTCATT CAATCTCAAA GAAGGAGCGA AAGTTAATTT CAAATTAAAA      2520

CCAAACGAGA ACATGAACAC AAGCAAACCT TTACCAATTC GGTTTTTAGC CAATATCACA     2580
```

```
GCCACTGGTG GGGGCTCTGT TTTTTTTGAT ATATATGCCA ACCATTCTGG CAGAGGGGCT      2640

GAGTTAAAAA TGAGTGAAAT TAATATCTCT AACGGCGCTA ATTTTACCTT AAATTCCCAT      2700

GTTCGCGGCG ATGACGCTTT TAAAATCAAC AAAGACTTAA CCATAAATGC AACCAATTCA      2760

AATTTCAGCC TCAGACAGAC GAAAGATGAT TTTTATGACG GGTACGCACG CAATGCCATC      2820

AATTCAACCT ACAACATATC CATTCTGGGC GGTAATGTCA CCCTTGGTGG ACAAAACTCA      2880

AGCAGCAGCA TTACGGGGAA TATTACTATC GAGAAAGCAG CAAATGTTAC GCTAGAAGCC      2940

AATAACGCCC CTAATCAGCA AAACATAAGG GATAGAGTTA TAAAACTTGG CAGCTTGCTC      3000

GTTAATGGGA GTTTAAGTTT AACTGGCGAA AATGCAGATA TTAAAGGCAA TCTCACTATT      3060

TCAGAAAGCG CCACTTTTAA AGGAAAGACT AGAGATACCC TAAATATCAC CGGCAATTTT      3120

ACCAATAATG GCACTGCCGA AATTAATATA ACACAAGGAG TGGTAAAACT TGGCAATGTT      3180

ACCAATGATG GTGATTTAAA CATTACCACT CACGCTAAAC GCAACCAAAG AAGCATCATC      3240

GGCGGAGATA TAATCAACAA AAAAGGAAGC TTAAATATTA CAGACAGTAA TAATGATGCT      3300

GAAATCCAAA TTGGCGGCAA TATCTCGCAA AAAGAAGGCA ACCTCACGAT TTCTTCCGAT      3360

AAAATTAATA TCACCAAACA GATAACAATC AAAAAGGGTA TTGATGGAGA GGACTCTAGT      3420

TCAGATGCGA CAAGTAATGC CAACCTAACT ATTAAAACCA AGAATTGAA ATTGACAGAA       3480

GACCTAAGTA TTTCAGGTTT CAATAAAGCA GAGATTACAG CCAAAGATGG TAGAGATTTA      3540

ACTATTGGCA ACAGTAATGA CGGTAACAGC GGTGCCGAAG CCAAAACAGT AACTTTTAAC      3600

AATGTTAAAG ATTCAAAAAT CTCTGCTGAC GGTCACAATG TGACACTAAA TAGCAAAGTG      3660

AAAACATCTA GCAGCAATGG CGGACGTGAA AGCAATAGCG ACAACGATAC CGGCTTAACT      3720

ATTACTGCAA AAAATGTAGA AGTAAACAAA GATATTACTT CTCTCAAAAC AGTAAATATC      3780

ACCGCGTCGG AAAAGGTTAC CACCACAGCA GGCTCGACCA TTAACGCAAC AAATGGCAAA      3840

GCAAGTATTA CAACCAAAAC AGGTGATATC AGCGGTACGA TTTCCGGTAA CACGGTAAGT      3900

GTTAGCGCGA CTGGTGATTT AACCACTAAA TCCGGCTCAA AAATTGAAGC GAAATCGGGT      3960

GAGGCTAATG TAACAAGTGC AACAGGTACA ATTGGCGGTA CAATTTCCGG TAATACGGTA      4020

AATGTTACGG CAAACGCTGG CGATTTAACA GTTGGGAATG GCGCAGAAAT TAATGCGACA      4080

GAAGGAGCTG CAACCTTAAC CGCAACAGGG AATACCTTGA CTACTGAAGC CGGTTCTAGC      4140

ATCACTTCAA CTAAGGGTCA GGTAGACCTC TTGGCTCAGA ATGGTAGCAT CGCAGGAAGC      4200

ATTAATGCTG CTAATGTGAC ATTAAATACT ACAGGCACCT TAACCACCGT GGCAGGCTCG      4260

GATATTAAAG CAACCAGCGG CACCTTGGTT ATTAACGCAA AGATGCTAA GCTAAATGGT       4320

GATGCATCAG GTGATAGTAC AGAAGTGAAT GCAGTCAACG CAAGCGGCTC TGGTAGTGTG      4380

ACTGCGGCAA CCTCAAGCAG TGTGAATATC ACTGGGGATT TAAACACAGT AAATGGGTTA      4440

AATATCATTT CGAAAGATGG TAGAAACACT GTGCGCTTAA GAGGCAAGGA AATTGAGGTG      4500

AAATATATCC AGCCAGGTGT AGCAAGTGTA GAAGAAGTAA TTGAAGCGAA ACGCGTCCTT      4560

GAAAAAGTAA AAGATTTATC TGATGAAGAA AGAGAAACAT TAGCTAAACT TGGTGTAAGT      4620

GCTGTACGTT TTGTTGAGCC AAATAATACA ATTACAGTCA ATACACAAAA TGAATTTACA      4680

ACCAGACCGT CAAGTCAAGT GATAATTTCT GAAGGTAAGG CGTGTTTCTC AAGTGGTAAT      4740

GGCGCACGAG TATGTACCAA TGTTGCTGAC GATGGACAGC CGTAGTCAGT AATTGACAAG      4800

GTAGATTTCA TCCTGCAATG AAGTCATTTT ATTTTCGTAT TATTTACTGT GTGGGTTAAA      4860

GTTCAGTACG GGCTTTACCC ATCTTGTAAA AAATTACGGA GAATACAATA AGTATTTTT      4920

AACAGGTTAT TATTATG                                                    4937
```

(2) INFORMATION FOR SEQ ID NO:4:

(i) SEQUENCE CHARACTERISTICS:
        (A) LENGTH: 1477 amino acids
        (B) TYPE: amino acid
        (C) STRANDEDNESS: single
        (D) TOPOLOGY: linear (xi) SEQUENCE DESCRIPTION: SEQ ID NO:4:

```
Met Asn Lys Ile Tyr Arg Leu Lys Phe Ser Lys Arg Leu Asn Ala Leu
 1               5                  10                  15

Val Ala Val Ser Glu Leu Ala Arg Gly Cys Asp His Ser Thr Glu Lys
            20                  25                  30

Gly Ser Glu Lys Pro Ala Arg Met Lys Val Arg His Leu Ala Leu Lys
        35                  40                  45

Pro Leu Ser Ala Met Leu Leu Ser Leu Gly Val Thr Ser Ile Pro Gln
50                  55                  60

Ser Val Leu Ala Ser Gly Leu Gln Gly Met Asp Val Val His Gly Thr
65                  70                  75                  80

Ala Thr Met Gln Val Asp Gly Asn Lys Thr Ile Ile Arg Asn Ser Val
                85                  90                  95

Asp Ala Ile Ile Asn Trp Lys Gln Phe Asn Ile Asp Gln Asn Glu Met
            100                 105                 110

Val Gln Phe Leu Gln Glu Asn Asn Ser Ala Val Phe Asn Arg Val
        115                 120                 125

Thr Ser Asn Gln Ile Ser Gln Leu Lys Gly Ile Leu Asp Ser Asn Gly
        130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Phe Glu Gln Thr Lys Asp Lys
            180                 185                 190

Ala Leu Ala Glu Ile Val Asn His Gly Leu Ile Thr Val Gly Lys Asp
        195                 200                 205

Gly Ser Val Asn Leu Ile Gly Gly Lys Val Lys Asn Glu Gly Val Ile
        210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Val Asn Leu Gly Asp Ile Phe Ala Lys Gly Gly Asn
            260                 265                 270

Ile Asn Val Arg Ala Ala Thr Ile Arg Asn Gln Gly Lys Leu Ser Ala
        275                 280                 285

Asp Ser Val Ser Lys Asp Lys Ser Gly Asn Ile Val Leu Ser Ala Lys
290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
            325                 330                 335

Thr Gly Ala Val Ile Asp Leu Ser Gly Lys Glu Gly Gly Glu Thr Tyr
        340                 345                 350

Leu Gly Gly Asp Glu Arg Gly Glu Gly Lys Asn Gly Ile Gln Leu Ala
        355                 360                 365
```

-continued

```
Lys Lys Thr Ser Leu Glu Lys Gly Ser Thr Ile Asn Val Ser Gly Lys
    370                 375                 380
Glu Lys Gly Gly Phe Ala Ile Val Trp Gly Asp Ile Ala Leu Ile Asp
385                 390                 395                 400
Gly Asn Ile Asn Ala Gln Gly Ser Gly Asp Ile Ala Lys Thr Gly Gly
                    405                 410                 415
Phe Val Glu Thr Ser Gly His Asp Leu Phe Ile Lys Asp Asn Ala Ile
                420                 425                 430
Val Asp Ala Lys Glu Trp Leu Leu Asp Phe Asp Asn Val Ser Ile Asn
                435                 440                 445
Ala Glu Asp Pro Leu Phe Asn Asn Thr Gly Ile Asn Asp Glu Phe Pro
                450                 455                 460
Thr Gly Thr Gly Glu Ala Ser Asp Pro Lys Lys Asn Ser Glu Leu Lys
465                 470                 475                 480
Thr Thr Leu Thr Asn Thr Thr Ile Ser Asn Tyr Leu Lys Asn Ala Trp
                485                 490                 495
Thr Met Asn Ile Thr Ala Ser Arg Lys Leu Thr Val Asn Ser Ser Ile
                500                 505                 510
Asn Ile Gly Ser Asn Ser His Leu Ile Leu His Ser Lys Gly Gln Arg
                515                 520                 525
Gly Gly Gly Val Gln Ile Asp Gly Asp Ile Thr Ser Lys Gly Gly Asn
530                 535                 540
Leu Thr Ile Tyr Ser Gly Gly Trp Val Asp Val His Lys Asn Ile Thr
545                 550                 555                 560
Leu Asp Gln Gly Phe Leu Asn Ile Thr Ala Ala Ser Val Ala Phe Glu
                565                 570                 575
Gly Gly Asn Asn Lys Ala Arg Asp Ala Ala Asn Ala Lys Ile Val Ala
                580                 585                 590
Gln Gly Thr Val Thr Ile Thr Gly Glu Gly Lys Asp Phe Arg Ala Asn
                595                 600                 605
Asn Val Ser Leu Asn Gly Thr Gly Lys Gly Leu Asn Ile Ile Ser Ser
                610                 615                 620
Val Asn Asn Leu Thr His Asn Leu Ser Gly Thr Ile Asn Ile Ser Gly
625                 630                 635                 640
Asn Ile Thr Ile Asn Gln Thr Thr Arg Lys Asn Thr Ser Tyr Trp Gln
                645                 650                 655
Thr Ser His Asp Ser His Trp Asn Val Ser Ala Leu Asn Leu Glu Thr
                660                 665                 670
Gly Ala Asn Phe Thr Phe Ile Lys Tyr Ile Ser Ser Asn Ser Lys Gly
                675                 680                 685
Leu Thr Thr Gln Tyr Arg Ser Ser Ala Gly Val Asn Phe Asn Gly Val
                690                 695                 700
Asn Gly Asn Met Ser Phe Asn Leu Lys Glu Gly Ala Lys Val Asn Phe
705                 710                 715                 720
Lys Leu Lys Pro Asn Glu Asn Met Asn Thr Ser Lys Pro Leu Pro Ile
                725                 730                 735
Arg Phe Leu Ala Asn Ile Thr Ala Thr Gly Gly Ser Val Phe Phe
                740                 745                 750
Asp Ile Tyr Ala Asn His Ser Gly Arg Gly Ala Glu Leu Lys Met Ser
                755                 760                 765
Glu Ile Asn Ile Ser Asn Gly Ala Asn Phe Thr Leu Asn Ser His Val
                770                 775                 780
Arg Gly Asp Asp Ala Phe Lys Ile Asn Lys Asp Leu Thr Ile Asn Ala
785                 790                 795                 800
```

-continued

```
Thr Asn Ser Asn Phe Ser Leu Arg Gln Thr Lys Asp Asp Phe Tyr Asp
                805                 810                 815
Gly Tyr Ala Arg Asn Ala Ile Asn Ser Thr Tyr Asn Ile Ser Ile Leu
        820                 825                 830
Gly Gly Asn Val Thr Leu Gly Gly Gln Asn Ser Ser Ser Ile Thr
            835                 840                 845
Gly Asn Ile Thr Ile Glu Lys Ala Ala Asn Val Thr Leu Glu Ala Asn
850                 855                 860
Asn Ala Pro Asn Gln Gln Asn Ile Arg Asp Arg Val Ile Lys Leu Gly
865                 870                 875                 880
Ser Leu Leu Val Asn Gly Ser Leu Ser Leu Thr Gly Glu Asn Ala Asp
                885                 890                 895
Ile Lys Gly Asn Leu Thr Ile Ser Glu Ser Ala Thr Phe Lys Gly Lys
                900                 905                 910
Thr Arg Asp Thr Leu Asn Ile Thr Gly Asn Phe Thr Asn Asn Gly Thr
            915                 920                 925
Ala Glu Ile Asn Ile Thr Gln Gly Val Val Lys Leu Gly Asn Val Thr
            930                 935                 940
Asn Asp Gly Asp Leu Asn Ile Thr Thr His Ala Lys Arg Asn Gln Arg
945                 950                 955                 960
Ser Ile Ile Gly Gly Asp Ile Ile Asn Lys Lys Gly Ser Leu Asn Ile
                965                 970                 975
Thr Asp Ser Asn Asn Asp Ala Glu Ile Gln Ile Gly Gly Asn Ile Ser
            980                 985                 990
Gln Lys Glu Gly Asn Leu Thr Ile Ser Ser Asp Lys Ile Asn Ile Thr
            995                 1000                1005
Lys Gln Ile Thr Ile Lys Lys Gly Ile Asp Gly Glu Asp Ser Ser Ser
    1010                1015                1020
Asp Ala Thr Ser Asn Ala Asn Leu Thr Ile Lys Thr Lys Glu Leu Lys
1025                1030                1035                1040
Leu Thr Glu Asp Leu Ser Ile Ser Gly Phe Asn Lys Ala Glu Ile Thr
                1045                1050                1055
Ala Lys Asp Gly Arg Asp Leu Thr Ile Gly Asn Ser Asn Asp Gly Asn
            1060                1065                1070
Ser Gly Ala Glu Ala Lys Thr Val Thr Phe Asn Asn Val Lys Asp Ser
        1075                1080                1085
Lys Ile Ser Ala Asp Gly His Asn Val Thr Leu Asn Ser Lys Val Lys
    1090                1095                1100
Thr Ser Ser Ser Asn Gly Gly Arg Glu Ser Asn Ser Asp Asn Asp Thr
1105                1110                1115                1120
Gly Leu Thr Ile Thr Ala Lys Asn Val Glu Val Asn Lys Asp Ile Thr
            1125                1130                1135
Ser Leu Lys Thr Val Asn Ile Thr Ala Ser Glu Lys Val Thr Thr Thr
        1140                1145                1150
Ala Gly Ser Thr Ile Asn Ala Thr Asn Gly Lys Ala Ser Ile Thr Thr
    1155                1160                1165
Lys Thr Gly Asp Ile Ser Gly Thr Ile Ser Gly Asn Thr Val Ser Val
    1170                1175                1180
Ser Ala Thr Val Asp Leu Thr Thr Lys Ser Gly Ser Lys Ile Glu Ala
1185                1190                1195                1200
Lys Ser Gly Glu Ala Asn Val Ser Ala Thr Gly Thr Ile Gly Gly
                1205                1210                1215
Thr Ile Ser Gly Asn Thr Val Asn Val Thr Ala Asn Ala Gly Asp Leu
```

```
            1220                1225                1230
    Thr Val Gly Asn Gly Ala Glu Ile Asn Ala Thr Glu Gly Ala Ala Thr
            1235                1240                1245

Leu Thr Ala Thr Gly Asn Thr Leu Thr Thr Glu Ala Gly Ser Ser Ile
            1250                1255                1260

Thr Ser Thr Lys Gly Gln Val Asp Leu Leu Ala Gln Asn Gly Ser Ile
    1265                1270                1275                1280

Ala Gly Ser Ile Asn Ala Ala Asn Val Thr Leu Asn Thr Thr Gly Thr
                1285                1290                1295

Leu Thr Thr Val Ala Gly Ser Asp Ile Lys Ala Thr Ser Gly Thr Leu
                1300                1305                1310

Val Ile Asn Ala Lys Asp Ala Lys Leu Asn Gly Asp Ala Ser Gly Asp
                1315                1320                1325

Ser Thr Glu Val Asn Ala Val Asn Ala Ser Gly Ser Gly Ser Val Thr
            1330                1335                1340

Ala Ala Thr Ser Ser Ser Val Asn Ile Thr Gly Asp Leu Asn Thr Val
    1345                1350                1355                1360

Asn Gly Leu Asn Ile Ile Ser Lys Asp Gly Arg Asn Thr Val Arg Leu
                1365                1370                1375

Arg Gly Lys Glu Ile Glu Val Lys Tyr Ile Gln Pro Gly Val Ala Ser
                1380                1385                1390

Val Glu Glu Val Ile Glu Ala Lys Arg Val Leu Glu Lys Val Lys Asp
                1395                1400                1405

Leu Ser Asp Glu Glu Arg Glu Thr Leu Ala Lys Leu Gly Val Ser Ala
                1410                1415                1420

Val Arg Phe Val Glu Pro Asn Asn Thr Ile Thr Val Asn Thr Gln Asn
    1425                1430                1435                1440

Glu Phe Thr Thr Arg Pro Ser Ser Gln Val Ile Ile Ser Glu Gly Lys
                1445                1450                1455

Ala Cys Phe Ser Ser Gly Asn Gly Ala Arg Val Cys Thr Asn Val Ala
                1460                1465                1470

Asp Asp Gly Gln Pro
            1475

(2) INFORMATION FOR SEQ ID NO:5:

(i) SEQUENCE CHARACTERISTICS:
        (A) LENGTH: 9171 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

ACAGCGTTCT CTTAATACTA GTACAAACCC ACAATAAAAT ATGACAAACA ACAATTACAA      60

CACCTTTTTT GCAGTCTATA TGCAAATATT TTAAAAAATA GTATAAATCC GCCATATAAA     120

ATGGTATAAT CTTTCATCTT TCATCTTTCA TCTTTTCATCT TTCATCTTTC ATCTTTCATC    180

TTTCATCTTT CATCTTTCAT CTTTCATCTT TCATCTTTCA TCTTTCATCT TTCATCTTTC     240

ACATGAAATG ATGAACCGAG GGAAGGGAGG GAGGGGCAAG AATGAAGAGG GAGCTGAACG     300

AACGCAAATG ATAAAGTAAT TTAATTGTTC AACTAACCTT AGGAGAAAAT ATGAACAAGA     360

TATATCGTCT CAAATTCAGC AAACGCCTGA ATGCTTTGGT TGCTGTGTCT GAATTGGCAC     420

GGGGTTGTGA CCATTCCACA GAAAAAGGCA GCGAAAAACC TGCTCGCATG AAAGTGCGTC     480

ACTTAGCGTT AAAGCCACTT TCCGCTATGT TACTATCTTT AGGTGTAACA TCTATTCCAC     540
```

```
AATCTGTTTT AGCAAGCGGC TTACAAGGAA TGGATGTAGT ACACGGCACA GCCACTATGC      600

AAGTAGATGG TAATAAAACC ATTATCCGCA ACAGTGTTGA CGCTATCATT AATTGGAAAC      660

AATTTAACAT CGACCAAAAT GAAATGGTGC AGTTTTTACA AGAAAACAAC AACTCCGCCG      720

TATTCAACCG TGTTACATCT AACCAAATCT CCCAATTAAA AGGGATTTTA GATTCTAACG      780

GACAAGTCTT TTTAATCAAC CCAAATGGTA TCACAATAGG TAAAGACGCA ATTATTAACA      840

CTAATGGCTT TACGGCTTCT ACGCTAGACA TTTCTAACGA AAACATCAAG GCGCGTAATT      900

TCACCTTCGA GCAAACCAAA GATAAAGCGC TCGCTGAAAT TGTGAATCAC GGTTTAATTA      960

CTGTCGGTAA AGACGGCAGT GTAAATCTTA TTGGTGGCAA AGTGAAAAAC GAGGGTGTGA     1020

TTAGCGTAAA TGGTGGCAGC ATTTCTTTAC TCGCAGGGCA AAAAATCACC ATCAGCGATA     1080

TAATAAACCC AACCATTACT TACAGCATTG CCGCGCCTGA AAATGAAGCG GTCAATCTGG     1140

GCGATATTTT TGCCAAAGGC GGTAACATTA ATGTCCGTGC TGCCACTATT CGAAACCAAG     1200

CTTTCCGCCA AAGAGGGTGA AGCGGAAATT GGCGGTGTAA TTTCCGCTCA AAATCAGCAA     1260

GCTAAAGGCG GCAAGCTGAT GATTACAGGC GATAAAGTCA CATTAAAAAC AGGTGCAGTT     1320

ATCGACCTTT CAGGTAAAGA AGGGGGAGAA ACTTACCTTG GCGGTGACGA GCGCGGCGAA     1380

GGTAAAAACG GCATTCAATT AGCAAAGAAA ACCTCTTTAG AAAAAGGCTC AACCATCAAT     1440

GTATCAGGCA AAGAAAAAGG CGGACGCGCT ATTGTGTGGG GCGATATTGC GTTAATTGAC     1500

GGCAATATTA ACGCTCAAGG TAGTGGTGAT ATCGCTAAAA CCGGTGGTTT TGTGGAGACG     1560

TCGGGGCATG ATTTATTCAT CAAAGACAAT GCAATTGTTG ACGCCAAAGA GTGGTTGTTA     1620

GACCCGGATA ATGTATCTAT TAATGCAGAA ACAGCAGGAC GCAGCAATAC TTCAGAAGAC     1680

GATGAATACA CGGGATCCGG GAATAGTGCC AGCACCCCAA AACGAAACAA AGAAAAGACA     1740

ACATTAACAA ACACAACTCT TGAGAGTATA CTAAAAAAAG GTACCTTTGT TAACATCACT     1800

GCTAATCAAC GCATCTATGT CAATAGCTCC ATTAATTTAT CCAATGGCAG CTTAACTCTT     1860

TGGAGTGAGG GTCGGAGCGG TGGCGGCGTT GAGATTAACA ACGATATTAC CACCGGTGAT     1920

GATACCAGAG GTGCAAACTT AACAATTTAC TCAGGCGGCT GGGTTGATGT TCATAAAAAT     1980

ATCTCACTCG GGGCGCAAGG TAACATAAAC ATTACAGCTA AACAAGATAT CGCCTTTGAG     2040

AAAGGAAGCA ACCAAGTCAT TACAGGTCAA GGGACTATTA CCTCAGGCAA TCAAAAAGGT     2100

TTTAGATTTA ATAATGTCTC TCTAAACGGC ACTGGCAGCG GACTGCAATT CACCACTAAA     2160

AGAACCAATA AATACGCTAT CACAAATAAA TTTGAAGGGA CTTTAAATAT TTCAGGGAAA     2220

GTGAACATCT CAATGGTTTT ACCTAAAAAT GAAAGTGGAT ATGATAAATT CAAAGGACGC     2280

ACTTACTGGA ATTTAACCTC GAAAGTGGAT ATGATAAATT CAAAGGACGC CCTCACTATT     2340

GACTCCAGAG GAAGCGATAG TGCAGGCACA CTTACCCAGC CTTATAATTT AAACGGTATA     2400

TCATTCAACA AAGACACTAC CTTTAATGTT GAACGAAATG CAAGAGTCAA CTTTGACATC     2460

AAGGCACCAA TAGGGATAAA TAAGTATTCT AGTTTGAATT ACGCATCATT TAATGGAAAC     2520

ATTTCAGTTT CGGGAGGGGG GAGTGTTGAT TTCACACTTC TCGCCTCATC CTCTAACGTC     2580

CAAACCCCCG GTGTAGTTAT AAATTCTAAA TACTTTAATG TTTCAACAGG GTCAAGTTTA     2640

AGATTTAAAA CTTCAGGCTC AACAAAAACT GGCTTCTCAA TAGAGAAAGA TTTAACTTTA     2700

AATGCCACCG GAGGCAACAT AACACTTTTG CAAGTTGAAG GCACCGATGG AATGATTGGT     2760

AAAGGCATTG TAGCCAAAAA AAACATAACC TTTGAAGGAG GTAAGATGAG GTTTGGCTCC     2820

AGGAAAGCCG TAACAGAAAT CGAAGGCAAT GTTACTATCA ATAACAACGC TAACGTCACT     2880

CTTATCGGTT CGGATTTTGA CAACCATCAA AAACCTTTAA CTATTAAAAA AGATGTCATC     2940
```

-continued

| | |
|---|---|
| ATTAATAGCG GCAACCTTAC CGCTGGAGGC AATATTGTCA ATATAGCCGG AAATCTTACC | 3000 |
| GTTGAAAGTA ACGCTAATTT CAAAGCTATC ACAAATTTCA CTTTTAATGT AGGCGGCTTG | 3060 |
| TTTGACAACA AAGGCAATTC AAATATTTCC ATTGCCAAAG GAGGGGCTCG CTTTAAAGAC | 3120 |
| ATTGATAATT CCAAGAATTT AAGCATCACC ACCAACTCCA GCTCCACTTA CCGCACTATT | 3180 |
| ATAAGCGGCA ATATAACCAA TAAAAACGGT GATTTAAATA TTACGAACGA AGGTAGTGAT | 3240 |
| ACTGAAATGC AAATTGGCGG CGATGTCTCG CAAAAAGAAG GTAATCTCAC GATTTCTTCT | 3300 |
| GACAAAATCA ATATTACCAA ACAGATAACA ATCAAGGCAG GTGTTGATGG GGAGAATTCC | 3360 |
| GATTCAGACG CGACAAACAA TGCCAATCTA ACCATTAAAA CCAAAGAATT GAAATTAACG | 3420 |
| CAAGACCTAA ATATTTCAGG TTTCAATAAA GCAGAGATTA CAGCTAAAGA TGGTAGTGAT | 3480 |
| TTAACTATTG GTAACACCAA TAGTGCTGAT GGTACTAATG CCAAAAAAGT AACCTTTAAC | 3540 |
| CAGGTTAAAG ATTCAAAAAT CTCTGCTGAC GGTCACAAGG TGACACTACA CAGCAAAGTG | 3600 |
| GAAACATCCG GTAGTAATAA CAACACTGAA GATAGCAGTG ACAATAATGC CGGCTTAACT | 3660 |
| ATCGATGCAA AAAATGTAAC AGTAAACAAC AATATTACTT CTCACAAAGC AGTGAGCATC | 3720 |
| TCTGCGACAA GTGGAGAAAT TACCACTAAA ACAGGTACAA CCATTAACGC AACCACTGGT | 3780 |
| AACGTGGAGA TAACCGCTCA AACAGGTAGT ATCCTAGGTG GAATTGAGTC CAGCTCTGGC | 3840 |
| TCTGTAACAC TTACTGCAAC CGAGGGCGCT CTTGCTGTAA GCAATATTTC GGGCAACACC | 3900 |
| GTTACTGTTA CTGCAAATAG CGGTGCATTA ACCACTTTGG CAGGCTCTAC AATTAAAGGA | 3960 |
| ACCGAGAGTG TAACCACTTC AAGTCAATCA GGCGATATCG GCGGTACGAT TTCTGGTGGC | 4020 |
| ACAGTAGAGG TTAAAGCAAC CGAAAGTTTA ACCACTCAAT CCAATTCAAA AATTAAAGCA | 4080 |
| ACAACAGGCG AGGCTAACGT AACAAGTGCA ACAGGTACAA TTGGTGGTAC GATTTCCGGT | 4140 |
| AATACGGTAA ATGTTACGGC AAACGCTGGC GATTTAACAG TTGGGAATGG CGCAGAAATT | 4200 |
| AATGCGACAG AAGGAGCTGC AACCTTAACT ACATCATCGG GCAAATTAAC TACCGAAGCT | 4260 |
| AGTTCACACA TTACTTCAGC CAAGGGTCAG GTAAATCTTT CAGCTCAGGA TGGTAGCGTT | 4320 |
| GCAGGAAGTA TTAATGCCGC CAATGTGACA CTAAATACTA CAGGCACTTT AACTACCGTG | 4380 |
| AAGGGTTCAA ACATTAATGC AACCAGCGGT ACCTTGGTTA TTAACGCAAA AGACGCTGAG | 4440 |
| CTAAATGGCG CAGCATTGGG TAACCACACA GTGGTAAATG CAACCAACGC AAATGGCTCC | 4500 |
| GGCAGCGTAA TCGCGACAAC CTCAAGCAGA GTGAACATCA CTGGGGATTT AATCACAATA | 4560 |
| AATGGATTAA ATATCATTTC AAAAAACGGT ATAAACACCG TACTGTTAAA AGGCGTTAAA | 4620 |
| ATTGATGTGA AATACATTCA ACCGGGTATA GCAAGCGTAG ATGAAGTAAT TGAAGCGAAA | 4680 |
| CGCATCCTTG AGAAGGTAAA AGATTTATCT GATGAAGAAA GAGAAGCGTT AGCTAAACTT | 4740 |
| GGCGTAAGTG CTGTACGTTT TATTGAGCCA AATAATACAA TTACAGTCGA TACACAAAAT | 4800 |
| GAATTTGCAA CCAGACCATT AAGTCGAATA GTGATTTCTG AAGGCAGGGC GTGTTTCTCA | 4860 |
| AACAGTGATG GCGCGACGGT GTGCGTTAAT ATCGCTGATA ACGGGCGGTA GCGGTCAGTA | 4920 |
| ATTGACAAGG TAGATTTCAT CCTGCAATGA AGTCATTTTA TTTTCGTATT ATTTACTGTG | 4980 |
| TGGGTTAAAG TTCAGTACGG GCTTTACCCA TCTTGTAAAA AATTACGGAG AATACAATAA | 5040 |
| AGTATTTTTA ACAGGTTATT ATTATGAAAA ATATAAAAAG CAGATTAAAA CTCAGTGCAA | 5100 |
| TATCAGTATT GCTTGGCCTG GCTTCTTCAT CATTGTATGC AGAAGAAGCG TTTTTAGTAA | 5160 |
| AAGGCTTTCA GTTATCTGGT GCACTTGAAA CTTTAAGTGA AGACGCCCAA CTGTCTGTAG | 5220 |
| CAAAATCTTT ATCTAAATAC CAAGGCTCGC AAACTTTAAC AAACCTAAAA ACAGCACAGC | 5280 |
| TTGAATTACA GGCTGTGCTA GATAAGATTG AGCCAAATAA GTTTGATGTG ATATTGCCAC | 5340 |

```
AACAAACCAT TACGGATGGC AATATTATGT TTGAGCTAGT CTCGAAATCA GCCGCAGAAA    5400

GCCAAGTTTT TTATAAGGCG AGCCAGGGTT ATAGTGAAGA AAATATCGCT CGTAGCCTGC    5460

CATCTTTGAA ACAAGGAAAA GTGTATGAAG ATGGTCGTCA GTGGTTCGAT TTGCGTGAAT    5520

TCAATATGGC AAAAGAAAAT CCACTTAAAG TCACTCGCGT GCATTACGAG TTAAACCCTA    5580

AAAACAAAAC CTCTGATTTG GTAGTTGCAG GTTTTTCGCC TTTTGGCAAA ACGCGTAGCT    5640

TTGTTTCCTA TGATAATTTC GGCGCAAGGG AGTTTAACTA TCAACGTGTA AGTCTAGGTT    5700

TTGTAAATGC CAATTTGACC GGACATGATG ATGTATTAAA TCTAAACGCA TTGACCAATG    5760

TAAAAGCACC ATCAAAATCT TATGCGGTAG GCATAGGATA TACTTATCCG TTTTATGATA    5820

AACACCAATC CTTAAGTCTT TATACCAGCA TGAGTTATGC TGATTCTAAT GATATCGACG    5880

GCTTACCAAG TGCGATTAAT CGTAAATTAT CAAAAGGTCA ATCTATCTCT GCGAATCTGA    5940

AATGGAGTTA TTATCTCCCG ACATTTAACC TTGGAATGGA AGACCAGTTT AAAATTAATT    6000

TAGGCTACAA CTACCGCCAT ATTAATCAAA CATCCGAGTT AAACACCCTG GGTGCAACGA    6060

AGAAAAAATT TGCAGTATCA GGCGTAAGTG CAGGCATTGA TGGACATATC CAATTTACCC    6120

CTAAAACAAT CTTTAATATT GATTTAACTC ATCATTATTA CGCGAGTAAA TTACCAGGCT    6180

CTTTTGGAAT GGAGCGCATT GGCGAAACAT TTAATCGCAG CTATCACATT AGCACAGCCA    6240

GTTTAGGGTT GAGTCAAGAG TTTGCTCAAG GTTGGCATTT TAGCAGTCAA TTATCGGGTC    6300

AGTTTACTCT ACAAGATATA AGTAGCATAG ATTTATTCTC TGTAACAGGT ACTTATGGCG    6360

TCAGAGGCTT TAAATACGGC GGTGCAAGTG GTGAGCGCGG TCTTGTATGG CGTAATGAAT    6420

TAAGTATGCC AAAATACACC CGCTTTCAAA TCAGCCCTTA TGCGTTTTAT GATGCAGGTC    6480

AGTTCCGTTA TAATAGCGAA AATGCTAAAA CTTACGGCGA AGATATGCAC ACGGTATCCT    6540

CTGCGGGTTT AGGCATTAAA ACCTCTCCTA CACAAAACTT AAGCTTAGAT GCTTTTGTTG    6600

CTCGTCGCTT TGCAAATGCC AATAGTGACA ATTTGAATGG CAACAAAAAA CGCACAAGCT    6660

CACCTACAAC CTTCTGGGGT AGATTAACAT TCAGTTTCTA ACCCTGAAAT TTAATCAACT    6720

GGTAAGCGTT CCGCCTACCA GTTTATAACT ATATGCTTTA CCCGCCAATT TACAGTCTAT    6780

ACGCAACCCT GTTTTCATCC TTATATATCA AACAAACTAA GCAAACCAAG CAAACCAAGC    6840

AAACCAAGCA AACCAAGCAA ACCAAGCAAA CCAAGCAAAC CAAGCAAACC AAGCAAACCA    6900

AGCAAACCAA GCAAACCAAG CAAACCAAGC AAACCAAGCA ATGCTAAAAA CAATTTATA    6960

TGATAAACTA AACATACTC CATACCATGG CAATACAAGG GATTAATAA TATGACAAAA    7020

GAAAATTTAC AAAGTGTTCC ACAAAATACG ACCGCTTCAC TTGTAGAATC AAACAACGAC    7080

CAAACTTCCC TGCAAATACT TAAACAACCA CCCAAACCCA ACCTATTACG CCTGGAACAA    7140

CATGTCGCCA AAAAGATTA TGAGCTTGCT TGCCGCGAAT TAATGGCGAT TTTGGAAAAA    7200

ATGGACGCTA ATTTTGGAGG CGTTCACGAT ATTGAATTTG ACGCACCTGC TCAGCTGGCA    7260

TATCTACCCG AAAAACTACT AATTCATTTT GCCACTCGTC TCGCTAATGC AATTACAACA    7320

CTCTTTTCCG ACCCCGAATT GGCAATTTCC GAAGAAGGGG CATTAAAGAT GATTAGCCTG    7380

CAACGCTGGT TGACGCTGAT TTTTGCCTCT TCCCCCTACG TTAACGCAGA CCATATTCTC    7440

AATAAATATA ATATCAACCC AGATTCCGAA GGTGGCTTTC ATTTAGCAAC AGACAACTCT    7500

TCTATTGCTA AATTCTGTAT TTTTTACTTA CCCGAATCCA ATGTCAATAT GAGTTTAGAT    7560

GCGTTATGGG CAGGGAATCA ACAACTTTGT GCTTCATTGT GTTTTGCGTT GCAGTCTTCA    7620

CGTTTTATTG GTACTGCATC TGCGTTTCAT AAAAGAGCGG TGGTTTTACA GTGGTTTCCT    7680

AAAAAACTCG CCGAAATTGC TAATTTAGAT GAATTGCCTG CAAATATCCT TCATGATGTA    7740
```

```
TATATGCACT GCAGTTATGA TTTAGCAAAA AACAAGCACG ATGTTAAGCG TCCATTAAAC       7800

GAACTTGTCC GCAAGCATAT CCTCACGCAA GGATGGCAAG ACCGCTACCT TTACACCTTA       7860

GGTAAAAAGG ACGGCAAACC TGTGATGATG GTACTGCTTG AACATTTTAA TTCGGGACAT       7920

TCGATTTATC GCACGCATTC AACTTCAATG ATTGCTGCTC GAGAAAAATT CTATTTAGTC       7980

GGCTTAGGCC ATGAGGGCGT TGATAACATA GGTCGAGAAG TGTTTGACGA GTTCTTTGAA       8040

ATCAGTAGCA ATAATATAAT GGAGAGACTG TTTTTTATCC GTAAACAGTG CGAAACTTTC       8100

CAACCCGCAG TGTTCTATAT GCCAAGCATT GGCATGGATA TTACCACGAT TTTTGTGAGC       8160

AACACTCGGC TTGCCCCTAT TCAAGCTGTA GCCTTGGGTC ATCCTGCCAC TACGCATTCT       8220

GAATTTATTG ATTATGTCAT CGTAGAAGAT GATTATGTGG GCAGTGAAGA TTGTTTTAGC       8280

GAAACCCTTT TACGCTTACC CAAAGATGCC CTACCTTATG TACCATCTGC ACTCGCCCCA       8340

CAAAAGTGG ATTATGTACT CAGGGAAAAC CCTGAAGTAG TCAATATCGG TATTGCCGCT        8400

ACCACAATGA AATTAAACCC TGAATTTTTG CTAACATTGC AAGAAATCAG AGATAAAGCT       8460

AAAGTCAAAA TACATTTTCA TTTCGCACTT GGACAATCAA CAGGCTTGAC ACACCCTAT        8520

GTCAAATGGT TTATCGAAAG CTATTTAGGT GACGATGCCA CTGCACATCC CCACGCACCT      8580

TATCACGATT ATCTGGCAAT ATTGCGTGAT TGCGATATGC TACTAAATCC GTTTCCTTTC       8640

GGTAATACTA ACGGCATAAT TGATATGGTT ACATTAGGTT TAGTTGGTGT ATGCAAAACG       8700

GGGGATGAAG TACATGAACA TATTGATGAA GGTCTGTTTA AACGCTTAGG ACTACCAGAA       8760

TGGCTGATAG CCGACACACG AGAAACATAT ATTGAATGTG CTTTGCGTCT AGCAGAAAAC       8820

CATCAAGAAC GCCTTGAACT CCGTCGTTAC ATCATAGAAA ACAACGGCTT ACAAAAGCTT       8880

TTTACAGGCG ACCCTCGTCC ATTGGGCAAA ATACTGCTTA AGAAAACAAA TGAATGGAAG       8940

CGGAAGCACT TGAGTAAAAA ATAACGGTTT TTTAAAGTAA AAGTGCGGTT AATTTTCAAA       9000

GCGTTTTAAA AACCTCTCAA AAATCAACCG CACTTTTATC TTTATAACGC TCCCGCGCGC       9060

TGACAGTTTA TCTCTTTCTT AAAATACCCA TAAAATTGTG GCAATAGTTG GGTAATCAAA       9120

TTCAATTGTT GATACGGCAA ACTAAAGACG GCGCGTTCTT CGGCAGTCAT C                9171

(2) INFORMATION FOR SEQ ID NO:6:

(i) SEQUENCE CHARACTERISTICS:
        (A) LENGTH: 9323 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CGCCACTTCA ATTTTGGATT GTTGAAATTC AACTAACCAA AAAGTGCGGT TAAAATCTGT         60

GGAGAAAATA GGTTGTAGTG AAGAACGAGG TAATTGTTCA AAAGGATAAA GCTCTCTTAA        120

TTGGGCATTG GTTGGCGTTT CTTTTTCGGT TAATAGTAAA TTATATTCTG GACGACTATG        180

CAATCCACCA ACAACTTTAC CGTTGGTTTT AAGCGTTAAT GTAAGTTCTT GCTCTTCTTG        240

GCGAATACGT AATCCCATTT TTTGTTTAGC AAGAAAATGA TCGGGATAAT CATAATAGGT        300

GTTGCCCAAA AATAAATTTT GATGTTCTAA AATCATAAAT TTTGCAAGAT ATTGTGGCAA        360

TTCAATACCT ATTTGTGGCG AAATCGCCAA TTTTAATTCA ATTTCTTGTA GCATAATATT        420

TCCCACTCAA ATCAACTGGT TAAATATACA AGATAATAAA AATAAATCAA GATTTTTGTG        480

ATGACAAACA ACAATTACAA CACCTTTTTT GCAGTCTATA TGCAAATATT TTAAAAAAAT        540
```

```
AGTATAAATC CGCCATATAA AATGGTATAA TCTTTCATCT TTCATCTTTC ATCTTTCATC      600

TTTCATCTTT CATCTTTCAT CTTTCATCTT TCATCTTTCA TCTTTCATCT TTCATCTTTC      660

ATCTTTCATC TTTCATCTTT CACATGAAAT GATGAACCGA GGGAAGGGAG GGAGGGGCAA      720

GAATGAAGAG GGAGCTGAAC GAACGCAAAT GATAAAGTAA TTTAATTGTT CAACTAACCT      780

TAGGAGAAAA TATGAACAAG ATATATCGTC TCAAATTCAG CAAACGCCTG AATGCTTTGG      840

TTGCTGTGTC TGAATTGGCA CGGGGTTGTG ACCATTCCAC AGAAAAAGGC AGCGAAAAAC      900

CTGCTCGCAT GAAAGTGCGT CACTTAGCGT TAAAGCCACT TTCCGCTATG TTACTATCTT      960

TAGGTGTAAC ATCTATTCCA CAATCTGTTT TAGCAAGCGG CAATTTAACA TCGACCAAAA     1020

TGAAATGGTG CAGTTTTTAC AAGAAAACAA GTAATAAAAC CATTATCCGC AACAGTGTTG     1080

ACGCTATCAT TAATTGGAAA CAATTTAACA TCGACCAAAA TGAAATGGTG CAGTTTTTAC     1140

AAGAAAACAA CAACTCCGCC GTATTCAACC GTGTTACATC TAACCAAATC TCCCAATTAA     1200

AAGGGATTTT AGATTCTAAC GGACAAGTCT TTTTAATCAA CCCAAATGGT ATCACAATAG     1260

GTAAAGACGC AATTATTAAC ACTAATGGCT TTACGGCTTC TACGCTAGAC ATTTCTAACG     1320

AAAACATCAA GGCGCGTAAT TTCACCTTCG AGCAAACCAA AGATAAAGCG CTCGCTGAAA     1380

TTGTGAATCA CGGTTTAATT ACTGTCGGTA AAGACGGCAG TGTAAATCTT ATTGGTGGCA     1440

AAGTGAAAAA CGAGGGTGTG ATTAGCGTAA ATGGTGGCAG CATTTCTTTA CTCGCAGGGC     1500

AAAAAATCAC CATCAGCGAT ATAATAAACC CAACCATTAC TTACAGCATT GCCGCGCCTG     1560

AAAATGAAGC GGTCAATCTG GGCGATATTT TTGCCAAAGG CGGTAACATT AATGTCCGTG     1620

CTGCCACTAT TCGAAACCAA GGTAAACTTT CTGCTGATTC TGTAAGCAAA GATAAAAGCG     1680

GCAATATTGT TCTTTCCGCC AAAGAGGGTG AAGCGGAAAT TGGCGGTGTA ATTTCCGCTC     1740

AAAATCAGCA AGCTAAAGGC GGCAAGCTGA TGATAAAGTC CGATAAAGTC ACATTAAAAA     1800

CAGGTGCAGT TATCGACCTT TCAGGTAAAG AAGGGGGAGA AACTTACCTT GGCGGTGACG     1860

AGCGCGGCGA AGGTAAAAAC GGCATTCAAT TAGCAAAGAA AACCTCTTTA GAAAAAGGCT     1920

CAACCATCAA TGTATCAGGC AAAGAAAAAG GCGGACGCGC TATTGTGTGG GGCGATATTG     1980

CGTTAATTGA CGGCAATATT AACGCTCAAG GTAGTGGTGA TATCGCTAAA ACCGGTGGTT     2040

TTGTGGAGAC ATCGGGGCAT TATTTATCCA TTGACAGCAA TGCAATTGTT AAAACAAAAG     2100

AGTGGTTGCT AGACCCTGAT GATGTAACAA TTGAAGCCGA AGACCCCCTT CGCAATAATA     2160

CCGGTATAAA TGATGAATTC CCAACAGGCA CCGGTGAAGC AAGCGACCCT AAAAAAAATA     2220

GCGAACTCAA AACAACGCTA ACCAATACAA CTATTTCAAA TTATCTGAAA AACGCCTGGA     2280

CAATGAATAT AACGGCATCA AGAAAACTTA CCGTTAATAG CTCAATCAAC ATCGGAAGCA     2340

ACTCCCACTT AATTCTCCAT AGTAAAGGTC AGCGTGGCGG AGGCGTTCAG ATTGATGGAG     2400

ATATTACTTC TAAAGGCGGA AATTTAACCA TTTATTCTGG CGGATGGGTT GATGTTCATA     2460

AAAATATTAC GCTTGATCAG GGTTTTTTAA ATATTACCGC CGCTTCCGTA GCTTTTGAAG     2520

GTGGAAATAA CAAAGCACGC GACGCGGCAA ATGCTAAAAT TGTCGCCCAG GGCACTGTAA     2580

CCATTACAGG AGAGGGAAAA GATTTCAGGG CTAACAACGT ATCTTTAAAC GGAACGGGTA     2640

AAGGTCTGAA TATCATTTCA TCAGTGAATA ATTTAACCCA CAATCTTAGT GGCACAATTA     2700

ACATATCTGG GAATATAACA ATTAACCAAA CTACGAGAAA GAACACCTCG TATTGGCAAA     2760

CCAGCCATGA TTCGCACTGG AACGTCAGTG CTCTTAATCT AGAGACAGGC GCAAATTTTA     2820

CCTTTATTAA ATACATTTCA AGCAATAGCA AAGGCTTAAC AACACAGTAT AGAAGCTCTG     2880

CAGGGGTGAA TTTTAACGGC GTAAATGGCA ACATGTCATT CAATCTCAAA GAAGGAGCGA     2940
```

-continued

```
AAGTTAATTT CAAATTAAAA CCAAACGAGA ACATGAACAC AAGCAAACCT TTACCAATTC    3000

GGTTTTTAGC CAATATCACA GCCACTGGTG GGGGCTCTGT TTTTTTTGAT ATATATGCCA    3060

ACCATTCTGG CAGAGGGGCT GAGTTAAAAA TGAGTGAAAT TAATATCTCT AACGGCGCTA    3120

ATTTTACCTT AAATTCCCAT GTTCGCGGCG ATGACGCTTT TAAAATCAAC AAAGACTTAA    3180

CCATAAATGC AACCAATTCA AATTTCAGCC TCAGACAGAC GAAAGATGAT TTTTATGACG    3240

GGTACGCACG CAATGCCATC AATTCAACCT ACAACATATC CATTCTGGGC GGTAATGTCA    3300

CCCTTGGTGG ACAAAACTCA AGCAGCAGCA TTACGGGGAA TATTACTATC GAGAAAGCAG    3360

CAAATGTTAC GCTAGAAGCC AATAACGCCC CTAATCAGCA AAACATAAGG GATAGAGTTA    3420

TAAAACTTGG CAGCTTGCTC GTTAATGGGA GTTTAAGTTT AACTGGCGAA AATGCAGATA    3480

TTAAAGGCAA TCTCACTATT TCAGAAAGCG CCACTTTTAA AGGAAAGACT AGAGATACCC    3540

TAAATATCAC CGGCAATTTT ACCAATAATG GCACTGCCGA AATTAATATA ACACAAGGAG    3600

TGGTAAAACT TGGCAATGTT ACCAATGATG GTGATTTAAA CATTACCACT CACGCTAAAC    3660

GCAACCAAAG AAGCATCATC GGCGGAGATA TAATCAACAA AAAAGGAAGC TTAAATATTA    3720

CAGACAGTAA TAATGATGCT GAAATCCAAA TTGGCGGCAA TATCTCGCAA AAAGAAGGCA    3780

ACCTCACGAT TTCTTCCGAT AAAATTAATA TCACCAAACA GATAACAATC AAAAAGGGTA    3840

TTGATGGAGA GGACTCTAGT TCAGATGCGA CAAGTAATGC CAACCTAACT ATTAAAACCA    3900

AAGAATTGAA ATTGACAGAA GACCTAAGTA TTTCAGGTTT CAATAAAGCA GAGATTACAG    3960

CCAAAGATGG TAGAGATTTA ACTATTGGCA ACAGTAATGA CGGTAACAGC GGTGCCGAAG    4020

CCAAAACAGT AACTTTTAAC AATGTTAAAG ATTCAAAAAT CTCTGCTGAC GGTCACAATG    4080

TGACACTAAA TAGCAAAGTG AAAACATCTA GCAGCAATGG CGGACGTGAA AGCAATAGCG    4140

ACAACGATAC CGGCTTAACT ATTACTGCAA AAAATGTAGA AGTAAACAAA GATATTACTT    4200

CTCTCAAAAC AGTAAATATC ACCGCGTCGG AAAAGGTTAC CACCACAGCA GGCTCGACCA    4260

TTAACGCAAC AAATGGCAAA GCAAGTATTA CAACCAAAAC AGGTGATATC AGCGGTACGA    4320

TTTCCGGTAA CACGGTAAGT GTTAGCGCGA CTGGTGATTT AACCACTAAA TCCGGCTCAA    4380

AAATTGAAGC GAAATCGGGT GAGGCTAATG TAACAAGTGC AACAGGTACA ATTGGCGGTA    4440

CAATTTCCGG TAATACGGTA AATGTTACGG CAAACGCTGG CGATTTAACA GTTGGGAATG    4500

GCGCAGAAAT TAATGCGACA GAAGGAGCTG CAACCTTAAC CGCAACAGGG AATACCTTGA    4560

CTACTGAAGC CGGTTCTAGC ATCACTTCAA CTAAGGGTCA GGTAGACCTC TTGGCTCAGA    4620

ATGGTAGCAT CGCAGGAAGC ATTAATGCTG CTAATGTGAC ATTAAATACT ACAGGCACCT    4680

TAACCACCGT GGCAGGCTCG GATATTAAAG CAACCAGCGG CACCTTGGTT ATTAACGCAA    4740

AAGATGCTAA GCTAAATGGT GATGCATCAG GTGATAGTAC AGAAGTGAAT GCAGTCAACG    4800

ACTGGGGATT TGGTAGTGTG ACTGCGGCAA CCTCAAGCAG TGTGAATATC ACTGGGGATT    4860

TAAACACAGT AAATGGGTTA AATATCATTT CGAAAGATGG TAGAAACACT GTGCGCTTAA    4920

GAGGCAAGGA AATTGAGGTG AAATATATCC AGCCAGGTGT AGCAAGTGTA GAAGAAGTAA    4980

TTGAAGCGAA ACGCGTCCTT GAAAAAGTAA AAGATTTATC TGATGAAGAA AGAGAAACAT    5040

TAGCTAAACT TGGTGTAAGT GCTGTACGTT TTGTTGAGCC AAATAATACA ATTACAGTCA    5100

ATACACAAAA TGAATTTACA ACCAGACCGT CAAGTCAAGT GATAATTTCT GAAGGTAAGG    5160

CGTGTTTCTC AAGTGGTAAT GGCGCACGAG TATGTACCAA TGTTGCTGAC GATGGACAGC    5220

CGTAGTCAGT AATTGACAAG GTAGATTTCA TCCTGCAATG AAGTCATTTT ATTTTCGTAT    5280

TATTTACTGT GTGGGTTAAA GTTCAGTACG GGCTTTACCC ATCTTGTAAA AAATTACGGA    5340
```

```
GAATACAATA AAGTATTTTT AACAGGTTAT TATTATGAAA AATATAAAAA GCAGATTAAA    5400

ACTCAGTGCA ATATCAGTAT TGCTTGGCCT GGCTTCTTCA TCATTGTATG CAGAAGAAGC    5460

GTTTTTAGTA AAAGGCTTTC AGTTATCTGG TGCACTTGAA ACTTTAAGTG AAGACGCCCA    5520

ACTGTCTGTA GCAAAATCTT TATCTAAATA CCAAGGCTCG CAAACTTTAA CAAACCTAAA    5580

AACAGCACAG CTTGAATTAC AGGCTGTGCT AGATAAGATT GAGCCAAATA AATTTGATGT    5640

GATATTGCCG CAACAAACCA TTACGGATGG CAATATCATG TTTGAGCTAG TCTCGAAATC    5700

AGCCGCAGAA AGCCAAGTTT TTTATAAGGC GAGCCAGGGT TATAGTGAAG AAAATATCGC    5760

TCGTAGCCTG CCATCTTTGA AACAAGGAAA AGTGTATGAA GATGGTCGTC AGTGGTTCGA    5820

TTTGCGTGAA TTTAATATGG CAAAAGAAAA CCCGCTTAAG GTTACCCGTG TACATTACGA    5880

ACTAAACCCT AAAAACAAAA CCTCTAATTT GATAATTGCG GGCTTCTCGC CTTTTGGTAA    5940

AACGCGTAGC TTTATTTCTT ATGATAATTT CGGCGCGAGA GAGTTTAACT ACCAACGTGT    6000

AAGCTTGGGT TTTGTTAATG CCAATTTAAC TGGTCATGAT GATGTGTTAA TTATACCAGT    6060

ATGAGTTATG CTGATTCTAA TGATATCGAC GGCTTACCAA GTGCGATTAA TCGTAAATTA    6120

TCAAAAGGTC AATCTATCTC TGCGAATCTG AAATGGAGTT ATTATCTCCC AACATTTAAC    6180

CTTGGCATGG AAGACCAATT TAAAATTAAT TTAGGCTACA ACTACCGCCA TATTAATCAA    6240

ACCTCCGCGT TAAATCGCTT GGGTGAAACG AAGAAAAAAT TTGCAGTATC AGGCGTAAGT    6300

GCAGGCATTG ATGGACATAT CCAATTTACC CCTAAAACAA TCTTTAATAT TGATTTAACT    6360

CATCATTATT ACGCGAGTAA ATTACCAGGC TCTTTTGGAA TGGAGCGCAT TGGCGAAACA    6420

TTTAATCGCA GCTATCACAT TAGCACAGCC AGTTTAGGGT TGAGTCAAGA GTTTGCTCAA    6480

GGTTGGCATT TTAGCAGTCA ATTATCAGGT CAATTTACTC TACAAGATAT TAGCAGTATA    6540

GATTTATTCT CTGTAACAGG TACTTATGGC GTCAGAGGCT TTAAATACGG CGGTGCAAGT    6600

GGTGAGCGCG GTCTTGTATG GCGTAATGAA TTAAGTATGC CAAAATACAC CCGCTTCCAA    6660

ATCAGCCCTT ATGCGTTTTA TGATGCAGGT CAGTTCCGTT ATAATAGCGA AAATGCTAAA    6720

ACTTACGGCG AAGATATGCA CACGGTATCC TCTGCGGGTT TAGGCATTAA AACCTCTCCT    6780

ACACAAAACT TAAGCCTAGA TGCTTTTGTT GCTCGTCGCT TTGCAAATGC CAATAGTGAC    6840

AATTTGAATG GCAACAAAAA ACGCACAAGC TCACCTACAA CCTTCTGGGG GAGATTAACA    6900

TTCAGTTTCT AACCCTGAAA TTTAATCAAC TGGTAAGCGT TCCGCCTACC AGTTTATAAC    6960

TATATGCTTT ACCCGCCAAT TTACAGTCTA TAGGCAACCC TGTTTTTACC CTTATATATC    7020

AAATAAACAA GCTAAGCTGA GCTAAGCAAA CCAAGCAAAC TCAAGCAAGC CAAGTAATAC    7080

TAAAAAAACA ATTTATATGA TAAACTAAAG TATACTCCAT GCCATGGCGA TACAAGGGAT    7140

TTAATAATAT GACAAAAGAA AATTTGCAAA ACGCTCCTCA AGATGCGACC GCTTTACTTG    7200

CGGAATTAAG CAACAATCAA ACTCCCCTGC GAATATTTAA ACAACCACGC AAGCCCAGCC    7260

TATTACGCTT GGAACAACAT ATCGCAAAAA AAGATTATGA GTTTGCTTGT CGTGAATTAA    7320

TGGTGATTCT GGAAAAAATG GACGCTAATT TTGGAGGCGT TCACGATATT GAATTTGACG    7380

CACCCGCTCA GCTGGCATAT CTACCCGAAA AATTACTAAT TTATTTTGCC ACTCGTCTCG    7440

CTAATGCAAT TACAACACTC TTTTCCGACC CCGAATTGGC AATTTCTGAA GAAGGGGCGT    7500

TAAAGATGAT TAGCCTGCAA CGCTGGTTGA CGCTGATTTT TGCCTCTTCC CCCTACGTTA    7560

ACGCAGACCA TATTCTCAAT AAATATAATA TCAACCCAGA TTCCGAAGGT GGCTTTCATT    7620

TAGCAACAGA CAACTCTTCT ATTGCTAAAT TCTGTATTTT TTACTTACCC GAATCCAATG    7680

TCAATATGAG TTTAGATGCG TTATGGGCAG GGAATCAACA ACTTTGTGCT TCATTGTGTT    7740
```

```
TTGCGTTGCA GTCTTCACGT TTTATTGGTA CCGCATCTGC GTTTCATAAA AGAGCGGTGG      7800

TTTTACAGTG GTTTCCTAAA AAACTCGCCG AAATTGCTAA TTTAGATGAA TTGCCTGCAA      7860

ATATCCTTCA TGATGTATAT ATGCACTGCA GTTATGATTT AGCAAAAAAC AAGCACGATG      7920

TTAAGCGTCC ATTAAACGAA CTTGTCCGCA AGCATATCCT CACGCAAGGA TGGCAAGACC      7980

GCTACCTTTA CACCTTAGGT AAAAAGGACG GCAAACCTGT GATGATGGTA CTGCTTGAAC      8040

ATTTTAATTC GGGACATTCG ATTTATCGTA CACATTCAAC TTCAATGATT GCTGCTCGAG      8100

AAAAATTCTA TTTAGTCGGC TTAGGCCATG AGGGCGTTGA TAAAATAGGT CGAGAAGTGT      8160

TTGACGAGTT CTTTGAAATC AGTAGCAATA ATATAATGGA GAGACTGTTT TTTATCCGTA      8220

AACAGTGCGA AACTTTCCAA CCCGCAGTGT TCTATATGCC AAGCATTGGC ATGGATATTA      8280

CCACGATTTT TGTGAGCAAC ACTCGGCTTG CCCCTATTCA AGCTGTAGCC CTGGGTCATC      8340

CTGCCACTAC GCATTCTGAA TTTATTGATT ATGTCATCGT AGAAGATGAT TATGTGGGCA      8400

GTGAAGATTG TTTCAGCGAA ACCCTTTTAC GCTTACCCAA AGATGCCCTA CCTTATGTAC      8460

CTTCTGCACT CGCCCCACAA AAAGTGGATT ATGTACTCAG GGAAAACCCT GAAGTAGTCA      8520

ATATCGGTAT TGCCGCTACC ACAATGAAAT TAAACCCTGA ATTTTGCTA ACATTGCAAG       8580

AAATCAGAGA TAAAGCTAAA GTCAAAATAC ATTTTCATTT CGCACTTGGA CAATCAACAG      8640

GCTTGACACA CCCTTATGTC AAATGGTTTA TCGAAAGCTA TTTAGGTGAC GATGCCACTG      8700

CACATCCCCA CGCACCTTAT CACGATTATC TGGCAATATT GCGTGATTGC GATATGCTAC      8760

TAAATCCGTT TCCTTTCGGT AATACTAACG GCATAATTGA TATGGTTACA TTAGGTTTAG      8820

TTGGTGTATG CAAAACGGGG GATGAAGTAC ATGAACATAT TGATGAAGGT CTGTTTAAAC      8880

GCTTAGGACT ACCAGAATGG CTGATAGCCG ACACACGAGA AACATATATT GAATGTGCTT      8940

TGCGTCTAGC AGAAAACCAT CAAGAACGCC TTGAACTCCG TCGTTACATC ATAGAAAACA      9000

ACGGCTTACA AAAGCTTTTT ACAGGCGACC CTCGTCCATT GGGCAAAATA CTGCTTAAGA      9060

AAACAAATGA ATGGAAGCGG AAGCACTTGA GTAAAAAATA ACGGTTTTTT AAAGTAAAAG      9120

TGCGGTTAAT TTTCAAAGCG TTTTAAAAAC CTCTCAAAAA TCAACCGCAC TTTTATCTTT      9180

ATAACGATCC CGCACGCTGA CAGTTTATCA GCCTCCCGCC ATAAAACTCC GCCTTTCATG      9240

GCGGAGATTT TAGCCAAAAC TGGCAGAAAT TAAAGGCTAA ATCACCAAA TTGCACCACA       9300

AAATCACCAA TACCCACAAA AAA                                              9323

(2) INFORMATION FOR SEQ ID NO:7:

(i) SEQUENCE CHARACTERISTICS:
        (A) LENGTH: 4287 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GATCAATCTG GGCGATATTT TTGCCAAAGG TGGTAACATT AATGTCCGCG CTGCCACTAT        60

TCGCAATAAA GGTAAACTTT CTGCCGACTC TGTAAGCAAA GATAAAAGTG GTAACATTGT       120

TCTCTCTGCC AAAGAAGGTG AAGCGGAAAT TGGCGGTGTA ATTTCCGCTC AAAATCAGCA       180

AGCCAAAGGT GGTAAGTTGA TGATTACAGG CGATAAAGTT ACATTGAAAA CGGGTGCACT       240

TATCGACCTT TCGGGTAAAG AAGGGGGAGA AACTTATCTT GGCGGTGACG AGCGTGGCGA       300

AGGTAAAAAC GGCATTCAAT TAGCAAAGAA AACCACTTTA GAAAAAGGCT CAACAATTAA       360

TGTGTCAGGT AAAGAAAAAG CTGGGCGCGC TATTGTATGG GGCGATATTG CGTTAATTGA       420
```

```
CGGCAATATT AATGCCCAAG GTAAAGATAT CGCTAAAACT GGTGGTTTTG TGGAGACGTC    480

GGGGCATTAC TTATCCATTG ATGATAACGC AATTGTTAAA ACAAAAGAAT GGCTACTAGA    540

CCCAGAGAAT GTGACTATTG AAGCTCCTTC CGCTTCTCGC GTCGAGCTGG GTGCCGATAG    600

GAATTCCCAC TCGGCAGAGG TGATAAAAGT GACCCTAAAA AAAAATAACA CCTCCTTGAC    660

AACACTAACC AATACAACCA TTTCAAATCT TCTGAAAAGT GCCCACGTGG TGAACATAAC    720

GGCAAGGAGA AAACTTACCG TTAATAGCTC TATCAGTATA GAAAGAGGCT CCCACTTAAT    780

TCTCCACAGT GAAGGTCAGG GCGGTCAAGG TGTTCAGATT GATAAAGATA TTACTTCTGA    840

AGGCGGAAAT TTAACCATTT ATTCTGGCGG ATGGGTTGAT GTTCATAAAA ATATTACGCT    900

TGGTAGCGGC TTTTTAAACA TCACAACTAA AGAAGGAGAT ATCGCCTTCG AAGACAAGTC    960

TGGACGGAAC AACCTAACCA TTACAGCCCA AGGGACCATC ACCTCAGGTA ATAGTAACGG   1020

CTTTAGATTT AACAACGTCT CTCTAAACAG CCTTGGCGGA AAGCTGAGCT TTACTGACAG   1080

CAGAGAGGAC AGAGGTAGAA GAACTAAGGG TAATATCTCA AACAAATTTG ACGGAACGTT   1140

AAACATTTCC GGAACTGTAG ATATCTCAAT GAAAGCACCC AAAGTCAGCT GGTTTTACAG   1200

AGACAAAGGA CGCACCTACT GGAACGTAAC CACTTTAAAT GTTACCTCGG GTAGTAAATT   1260

TAACCTCTCC ATTGACAGCA CAGGAAGTGG CTCAACAGGT CCAAGCATAC GCAATGCAGA   1320

ATTAAATGGC ATAACATTTA ATAAAGCCAC TTTTAATATC GCACAAGGCT CAACAGCTAA   1380

CTTTAGCATC AAGGCATCAA TAATGCCCTT TAAGAGTAAC GCTAACTACG CATTATTTAA   1440

TGAAGATATT TCAGTCTCAG GGGGGGGTAG CGTTAATTTC AAACTTAACG CCTCATCTAG   1500

CAACATACAA ACCCCTGGCG TAATTATAAA ATCTCAAAAC TTTAATGTCT CAGGAGGGTC   1560

AACTTTAAAT CTCAAGGCTG AAGGTTCAAC AGAAACCGCT TTTTCAATAG AAAATGATTT   1620

AAACTTAAAC GCCACCGGTG GCAATATAAC AATCAGACAA GTCGAGGGTA CCGATTCACG   1680

CGTCAACAAA GGTGTCGCAG CCAAAAAAAA CATAACTTTT AAAGGGGGTA ATATCACCTT   1740

CGGCTCTCAA AAAGCCACAA CAGAAATCAA AGGCAATGTT ACCATCAATA AAAACACTAA   1800

CGCTACTCTT CGTGGTGCGA ATTTTGCCGA AAACAAATCG CCTTTAAATA TAGCAGGAAA   1860

TGTTATTAAT AATGGCAACC TTACCACTGC CGGCTCCATT ATCAATATAG CCGGAAATCT   1920

TACTGTTTCA AAAGGCGCTA ACCTTCAAGC TATAACAAAT TACACTTTTA ATGTAGCCGG   1980

CTCATTTGAC AACAATGGCG CTTCAAACAT TTCCATTGCC AGAGGAGGGG CTAAATTTAA   2040

AGATATCAAT AACACCAGTA GCTTAAATAT TACCACCAAC TCTGATACCA CTTACCGCAC   2100

CATTATAAAA GGCAATATAT CCAACAAATC AGGTGATTTG AATATTATTG ATAAAAAAAG   2160

CGACGCTGAA ATCCAAATTG GCGGCAATAT CTCACAAAAA GAAGGCAATC TCACAATTTC   2220

TTCTGATAAA GTAAATATTA CCAATCAGAT AACAATCAAA GCAGGCGTTG AAGGGGGGCG   2280

TTCTGATTCA AGTGAGGCAG AAAATGCTAA CCTAACTATT CAAACCAAAG AGTTAAAATT   2340

GGCAGGAGAC CTAAATATTT CAGGCTTTAA TAAAGCAGAA ATTACAGCTA AAAATGGCAG   2400

TGATTTAACT ATTGGCAATG CTAGCGGTGG TAATGCTGAT GCTAAAAAAG TGACTTTTGA   2460

CAAGGTTAAA GATTCAAAAA TCTCGACTGA CGGTCACAAT GTAACACTAA ATAGCGAAGT   2520

GAAAACGTCT AATGGTAGTA GCAATGCTGG TAATGATAAC AGCACCGGTT TAACCATTTC   2580

CGCAAAAGAT GTAACGGTAA ACAATAACGT TACCTCCCAC AAGACAATAA ATATCTCTGC   2640

CGCAGCAGGA AATGTAACAA CCAAAGAAGG CACAACTATC AATGCAACCA CAGGCAGCGT   2700

GGAAGTAACT GCTCAAAATG GTACAATTAA AGGCAACATT ACCTCGCAAA ATGTAACAGT   2760

GACAGCAACA GAAAATCTTG TTACCACAGA GAATGCTGTC ATTAATGCAA CCAGCGGCAC   2820
```

```
AGTAAACATT AGTACAAAAA CAGGGGATAT TAAAGGTGGA ATTGAATCAA CTTCCGGTAA    2880

TGTAAATATT ACAGCGAGCG GCAATACACT TAAGGTAAGT AATATCACTG GTCAAGATGT    2940

AACAGTAACA GCGGATGCAG GAGCCTTGAC AACTACAGCA GGCTCAACCA TTAGTGCGAC    3000

AACAGGCAAT GCAAATATTA CAACCAAAAC AGGTGATATC AACGGTAAAG TTGAATCCAG    3060

CTCCGGCTCT GTAACACTTG TTGCAACTGG AGCAACTCTT GCTGTAGGTA ATATTTCAGG    3120

TAACACTGTT ACTATTACTG CGGATAGCGG TAAATTAACC TCCACAGTAG GTTCTACAAT    3180

TAATGGGACT AATAGTGTAA CCACCTCAAG CCAATCAGGC GATATTGAAG GTACAATTTC    3240

TGGTAATACA GTAAATGTTA CAGCAAGCAC TGGTGATTTA ACTATTGGAA ATAGTGCAAA    3300

AGTTGAAGCG AAAAATGGAG CTGCAACCTT AACTGCTGAA TCAGGCAAAT TAACCACCCA    3360

AACAGGCTCT AGCATTACCT CAAGCAATGG TCAGACAACT CTTACAGCCA AGGATAGCAG    3420

TATCGCAGGA AACATTAATG CTGCTAATGT GACGTTAAAT ACCACAGGCA CTTTAACTAC    3480

TACAGGGGAT TCAAAGATTA ACGCAACCAG TGGTACCTTA ACAATCAATG CAAAAGATGC    3540

CAAATTAGAT GGTGCTGCAT CAGGTGACCG CACAGTAGTA AATGCAACTA ACGCAAGTGG    3600

CTCTGGTAAC GTGACTGCGA AAACCTCAAG CAGCGTGAAT ATCACCGGGG ATTTAAACAC    3660

AATAAATGGG TTAAATATCA TTTCGGAAAA TGGTAGAAAC ACTGTGCGCT TAAGAGGCAA    3720

GGAAATTGAT GTGAAATATA TCCAACCAGG TGTAGCAAGC GTAGAAGAGG TAATTGAAGC    3780

GAAACGCGTC CTTGAGAAGG TAAAAGATTT ATCTGATGAA GAAAGAGAAA CACTAGCCAA    3840

ACTTGGTGTA AGTGCTGTAC GTTTCGTTGA GCCAAATAAT GCCATTACGG TTAATACACA    3900

AAACGAGTTT ACAACCAAAC CATCAAGTCA AGTGACAATT TCTGAAGGTA AGGCGTGTTT    3960

CTCAAGTGGT AATGGCGCAC GAGTATGTAC CAATGTTGCT GACGATGGAC AGCAGTAGTC    4020

AGTAATTGAC AAGGTAGATT TCATCCTGCA ATGAAGTCAT TTTATTTTCG TATTATTTAC    4080

TGTGTGGGTT AAAGTTCAGT ACGGGCTTTA CCCACCTTGT AAAAAATTAC GAAAAATACA    4140

ATAAAGTATT TTTAACAGGT TATTATTATG AAAAACATAA AAAGCAGATT AAAACTCAGT    4200

GCAATATCAA TATTGCTTGG CTTGGCTTCT TCATCGACGT ATGCAGAAGA AGCGTTTTTA    4260

GTAAAAGGCT TTCAGTTATC TGGCGCG                                        4287

(2) INFORMATION FOR SEQ ID NO:8:

(i) SEQUENCE CHARACTERISTICS:
        (A) LENGTH: 4702 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGGAATGAGC GTCGTACACG GTACAGCAAC CATGCAAGTA GACGGCAATA AAACCACTAT      60

CCGTAATAGC ATCAATGCTA TCATCAATTG GAAACAATTT AACATTGACC AAAATGAAAT     120

GGAGCAGTTT TTACAAGAAA GCAGCAACTC TGCCGTTTTC AACCGTGTTA CATCTGACCA     180

AATCTCCCAA TTAAAAGGGA TTTTAGATTC TAACGGACAA GTCTTTTTAA TCAACCCAAA     240

TGGTATCACA ATAGGTAAAG ACGCAATTAT TAACACTAAT GGCTTTACTG CTTCTACGCT     300

AGACATTTCT AACGAAAACA TCAAGGCGCG TAATTTCACC CTTGAGCAAA CCAAGGATAA     360

AGCACTCGCT GAAATCGTGA ATCACGGTTT AATTACCGTT GGTAAAGACG GTAGCGTAAA     420

CCTTATTGGT GGCAAAGTGA AAAACGAGGG CGTGATTAGC GTAAATGGCG GTAGTATTTC     480
```

```
TTTACTTGCA GGGCAAAAAA TCACCATCAG CGATATAATA AATCCAACCA TCACTTACAG    540

CATTGCTGCA CCTGAAAACG AAGCGATCAA TCTGGGCGAT ATTTTTGCCA AAGGTGGTAA    600

CATTAATGTC CGCGCTGCCA CTATTCGCAA TAAAGGTAAA CTTTCTGCCG ACTCTGTAAG    660

CAAAGATAAA AGTGGTAACA TTGTTCTCTC TGCCAAAGAA GGTGAAGCGG AAATTGGCGG    720

TGTAATTTCC GCTCAAAATC AGCAAGCCAA AGGTGGTAAG TTGATGATTA CAGGTGATAA    780

AGTCACATTA AAAACAGGTG CAGTTATCGA CCTTTCAGGT AAAGAAGGGG GAGAGACTTA    840

TCTTGGCGGT GATGAGCGTG GCGAAGGTAA AAATGGTATT CAATTAGCGA AGAAAACCTC    900

TTTAGAAAAA GGCTCGACAA TTAATGTATC AGGCAAAGAA AAAGGCGGGC GCGCTATTGT    960

ATGGGGCGAT ATTGCATTAA TTAATGGTAA CATTAATGCT CAAGGTAGCG ATATTGCTAA   1020

AACTGGCGGC TTTGTGGAAA CATCAGGACA TGACTTATCC ATTGGTGATG ATGTGATTGT   1080

TGACGCTAAA GAGTGGTTAT TAGACCCAGA TGATGTGTCC ATTGAAACTC TTACATCTGG   1140

ACGCAATAAT ACCGGCGAAA ACCAAGGATA TACAACAGGA GATGGGACTA AAGAGTCACC   1200

TAAAGGTAAT AGTATTTCTA AACCTACATT AACAAACTCA ACTCTTGAGC AAATCCTAAG   1260

AAGAGGTTCT TATGTTAATA TCACTGCTAA TAATAGAATT TATGTTAATA GCTCCATCAA   1320

CTTATCTAAT GGCAGTTTAA CACTTCACAC TAAACGAGAT GGAGTTAAAA TTAACGGTGA   1380

TATTACCTCA AACGAAAATG GTAATTTAAC CATTAAAGCA GGCTCTTGGG TTGATGTTCA   1440

TAAAAACATC ACGCTTGGTA CGGGTTTTTT CAATATTGTC GCTGGGGATT CTGTAGCTTT   1500

TGAGAGAGAG GGCGATAAAG CACGTAACGC AACAGATGCT CAAATTACCG CACAAGGGAC   1560

GATAACCGTC AATAAAGATG ATAAACAATT TAGATTCAAT AATGTATCTA TTAACGGGAC   1620

GGGCAAGGGT TTAAAGTTTA TTGCAAATCA AAATAATTTC ACTCATAAAT TTGATGGCGA   1680

AATTAACATA TCTGGAATAG TAACAATTAA CCAAACCACG AAAAAAGATG TTAAATACTG   1740

GAATGCATCA AAAGACTCTT ACTGGAATGT TTCTTCTCTT ACTTTGAATA CGGTGCAAAA   1800

ATTTACCTTT ATAAAATTCG TTGATAGCGG CTCAAATTCC AAGATTTGA GGTCATCACG   1860

TAGAAGTTTT GCAGGCGTAC ATTTTAACGG CATCGGAGGC AAAACAAACT TCAACATCGG   1920

AGCTAACGCA AAAGCCTTAT TTAAATTAAA ACCAAACGCC GCTACAGACC CAAAAAAAGA   1980

ATTACCTATT ACTTTTAACG CCAACATTAC AGCTACCGGT AACAGTGATA GCTCTGTGAT   2040

GTTTGACATA CACGCCAATC TTACCTCTAG AGCTGCCGGC ATAAACATGG ATTCAATTAA   2100

CATTACCGGC GGGCTTGACT TTTCCATAAC ATCCCATAAT CGCAATAGTA ATGCTTTTGA   2160

AATCAAAAAA GACTTAACTA TAAATGCAAC TGGCTCGAAT TTTAGTCTTA AGCAAACGAA   2220

AGATTCTTTT TATAATGAAT ACAGCAAACA CGCCATTAAC TCAAGTCATA ATCTAACCAT   2280

TCTTGGCGGC AATGTCACTC TAGGTGGGGA AAATTCAAGC AGTAGCATTA CGGGCAATAT   2340

CAATATCACC AATAAAGCAA ATGTTACATT ACAAGCTGAC ACCAGCAACA GCAACACAGG   2400

CTTGAAGAAA AGAACTCTAA CTCTTGGCAA TATATCTGTT GAGGGAATT TAAGCCTAAC   2460

TGGTGCAAAT GCAAACATTG TCGGCAATCT TTCTATTGCA GAAGATTCCA CATTTAAAGG   2520

AGAAGCCAGT GACAACCTAA ACATCACCGG CACCTTTACC AACAACGGTA CCGCCAACAT   2580

TAATATAAAA CAAGGAGTGG TAAAACTCCA AGGCGATATT ATCAATAAAG GTGGTTTAAA   2640

TATCACTACT AACGCCTCAG GCACTCAAAA AACCATTATT AACGGAAATA TAACTAACGA   2700

AAAAGGCGAC TTAAACATCA AGAATATTAA AGCCGACGCC GAAATCCAAA TTGGCGGCAA   2760

TATCTCACAA AAAGAAGGCA ATCTCACAAT TTCTTCTGAT AAAGTAAATA TTACCAATCA   2820

GATAACAATC AAAGCAGGCG TTGAAGGGGG GCGTTCTGAT TCAAGTGAGG CAGAAAATGC   2880
```

| | | |
|---|---|---|
| TAACCTAACT ATTCAAACCA AAGAGTTAAA ATTGGCAGGA GACCTAAATA TTTCAGGCTT | 2940 |
| TAATAAAGCA GAAATTACAG CTAAAAATGG CAGTGATTTA ACTATTGGCA ATGCTAGCGG | 3000 |
| TGGTAATGCT GATGCTAAAA AAGTGACTTT TGACAAGGTT AAAGATTCAA AAATCTCGAC | 3060 |
| TGACGGTCAC AATGTAACAC TAAATAGCGA AGTGAAAACG TCTAATGGTA GTAGCAATGC | 3120 |
| TGGTAATGAT AACAGCACCG GTTTAACCAT TTCCGCAAAA GATGTAACGG TAAACAATAA | 3180 |
| CGTTACCTCC CACAAGACAA TAAATATCTC TGCCGCAGCA GGAAATGTAA CAACCAAAGA | 3240 |
| AGGCACAACT ATCAATGCAA CCACAGGCAG CGTGGAAGTA ACTGCTCAAA ATGGTACAAT | 3300 |
| TAAAGGCAAC ATTACCTCGC AAAATGTAAC AGTGACAGCA ACAGAAAATC TTGTTACCAC | 3360 |
| AGAGAATGCT GTCATTAATG CAACCAGCGG CACAGTAAAC ATTAGTACAA AAACAGGGGA | 3420 |
| TATTAAAGGT GGAATTGAAT CAACTTCCGG TAATGTAAAT ATTACAGCGA GCGGCAATAC | 3480 |
| ACTTAAGGTA AGTAATATCA CTGGTCAAGA TGTAACAGTA ACAGCGGATG CAGGAGCCTT | 3540 |
| GACAACTACA GCAGGCTCAA CCATTAGTGC GACAACAGGC AATGCAAATA TTACAACCAA | 3600 |
| AACAGGTGAT ATCAACGGTA AAGTTGAATC CAGCTCCGGC TCTGTAACAC TTGTTGCAAC | 3660 |
| TGGAGCAACT CTTGCTGTAG GTAATATTTC AGGTAACACT GTTACTATTA CTGCGGATAG | 3720 |
| CGGTAAATTA ACCTCCACAG TAGGTTCTAC AATTAATGGG ACTAATAGTG TAACCACCTC | 3780 |
| AAGCCAATCA GGCGATATTG AAGGTACAAT TTCTGGTAAT ACAGTAAATG TTACAGCAAG | 3840 |
| CACTGGTGAT TTAACTATTG GAAATAGTGC AAAAGTTGAA GCGAAAAATG GAGCTGCAAC | 3900 |
| CTTAACTGCT GAATCAGGCA AATTAACCAC CCAAACAGGC TCTAGCATTA CCTCAAGCAA | 3960 |
| TGGTCAGACA ACTCTTACAG CCAAGGATAG CAGTATCGCA GGAAACATTA ATGCTGCTAA | 4020 |
| TGTGACGTTA AATACCACAG GCACTTTAAC TACTACAGGG GATTCAAAGA TTAACGCAAC | 4080 |
| CAGTGGTACC TTAACAATCA ATGCAAAAGA TGCCAAATTA GATGGTGCTG CATCAGGTGA | 4140 |
| CCGCACAGTA GTAAATGCAA CTAACGCAAG TGGCTCTGGT AACGTGACTG CGAAAACCTC | 4200 |
| AAGCAGCGTG AATATCACCG GGGATTTAAA CACAATAAAT GGGTTAAATA TCATTTCGGA | 4260 |
| AAATGGTAGA AACACTGTGC GCTTAAGAGG CAAGGAAATT GATGTGAAAT ATATCCAACC | 4320 |
| AGGTGTAGCA AGCGTAGAAG AGGTAATTGA AGCGAAACGC GTCCTTGAGA AGGTAAAAGA | 4380 |
| TTTATCTGAT GAAGAAAGAG AAACACTAGC CAAACTTGGT GTAAGTGCTG TACGTTTCGT | 4440 |
| TGAGCCAAAT AATGCCATTA CGGTTAATAC ACAAAACGAG TTTACAACCA AACCATCAAG | 4500 |
| TCAAGTGACA ATTTCTGAAG GTAAGGCGTG TTTCTCAAGT GGTAATGGCG CACGAGTATG | 4560 |
| TACCAATGTT GCTGACGATG GACAGCAGTA GTCAGTAATT GACAAGGTAG ATTTCATCCT | 4620 |
| GCAATGAAGT CATTTTATTT TCGTATTATT TACTGTGTGG GTTAAAGTTC AGTACGGGCT | 4680 |
| TTACCCACCT TGTAAAAAAT TA | 4702 |

(2) INFORMATION FOR SEQ ID NO:9:

(i) SEQUENCE CHARACTERISTICS:
        (A) LENGTH: 1338 amino acids
        (B) TYPE: amino acid
        (C) STRANDEDNESS: single
        (D) TOPOLOGY: linear (xi) SEQUENCE DESCRIPTION: SEQ ID NO:9:

```
Ile Asn Leu Gly Asp Ile Phe Ala Lys Gly Gly Asn Ile Asn Val Arg
 1               5                  10                  15

Ala Ala Thr Ile Arg Asn Lys Gly Lys Leu Ser Ala Asp Ser Val Ser
            20                  25                  30

Lys Asp Lys Ser Gly Asn Ile Val Leu Ser Ala Lys Glu Gly Glu Ala
```

```
                    35                  40                  45
    Glu Ile Gly Gly Val Ile Ser Ala Gln Asn Gln Gln Ala Lys Gly Gly
                    50                  55                  60
    Lys Leu Met Ile Thr Gly Asp Lys Val Thr Leu Lys Thr Gly Ala Val
     65                  70                  75                  80
    Ile Asp Leu Ser Gly Lys Glu Gly Glu Thr Tyr Leu Gly Gly Asp
                    85                  90                  95
    Glu Arg Gly Glu Gly Lys Asn Gly Ile Gln Leu Ala Lys Lys Thr Thr
                   100                 105                 110
    Leu Glu Lys Gly Ser Thr Ile Asn Val Ser Gly Lys Glu Lys Gly Gly
                   115                 120                 125
    Arg Ala Ile Val Trp Gly Asp Ile Ala Leu Ile Asp Gly Asn Ile Asn
                   130                 135                 140
    Ala Gln Gly Lys Asp Ile Ala Lys Thr Gly Gly Phe Val Glu Thr Ser
    145                 150                 155                 160
    Gly His Tyr Leu Ser Ile Asp Asp Asn Ala Ile Val Lys Thr Lys Glu
                   165                 170                 175
    Trp Leu Leu Asp Pro Glu Asn Val Thr Ile Glu Ala Pro Ser Ala Ser
                   180                 185                 190
    Arg Val Glu Leu Gly Ala Asp Arg Asn Ser His Ser Ala Glu Val Ile
                   195                 200                 205
    Lys Val Thr Leu Lys Lys Asn Asn Thr Ser Leu Thr Thr Leu Thr Asn
    210                 215                 220
    Thr Thr Ile Ser Asn Leu Leu Lys Ser Ala His Val Val Asn Ile Thr
    225                 230                 235                 240
    Ala Arg Arg Lys Leu Thr Val Asn Ser Ile Ser Ile Glu Arg Gly
                   245                 250                 255
    Ser His Leu Ile Leu His Ser Glu Gly Gln Gly Gly Gln Gly Val Gln
                   260                 265                 270
    Ile Asp Lys Asp Ile Thr Ser Glu Gly Gly Asn Leu Thr Ile Tyr Ser
                   275                 280                 285
    Gly Gly Trp Val Asp Val His Lys Asn Ile Thr Leu Gly Ser Gly Phe
                   290                 295                 300
    Leu Asn Ile Thr Thr Lys Glu Gly Asp Ile Ala Phe Glu Asp Lys Ser
    305                 310                 315                 320
    Gly Arg Asn Asn Leu Thr Ile Thr Ala Gln Gly Thr Ile Thr Ser Gly
                   325                 330                 335
    Asn Ser Asn Gly Phe Arg Phe Asn Val Ser Leu Asn Ser Leu Gly
                   340                 345                 350
    Gly Lys Leu Ser Phe Thr Asp Ser Arg Glu Asp Arg Gly Arg Arg Thr
                   355                 360                 365
    Lys Gly Asn Ile Ser Asn Lys Phe Asp Gly Thr Leu Asn Ile Ser Gly
                   370                 375                 380
    Thr Val Asp Ile Ser Met Lys Ala Pro Lys Val Ser Trp Phe Tyr Arg
    385                 390                 395                 400
    Asp Lys Gly Arg Thr Tyr Trp Asn Val Thr Thr Leu Asn Val Thr Ser
                   405                 410                 415
    Gly Ser Lys Phe Asn Leu Ser Ile Asp Ser Thr Gly Ser Gly Ser Thr
                   420                 425                 430
    Gly Pro Ser Ile Arg Asn Ala Glu Leu Asn Gly Ile Thr Phe Asn Lys
                   435                 440                 445
    Ala Thr Phe Asn Ile Ala Gln Gly Ser Thr Ala Asn Phe Ser Ile Lys
    450                 455                 460
```

```
Ala Ser Ile Met Pro Phe Lys Ser Asn Ala Asn Tyr Ala Leu Phe Asn
465                 470                 475                 480

Glu Asp Ile Ser Val Ser Gly Gly Ser Val Asn Phe Lys Leu Asn
            485                 490                 495

Ala Ser Ser Ser Asn Ile Gln Thr Pro Gly Val Ile Ile Lys Ser Gln
                500                 505                 510

Asn Phe Asn Val Ser Gly Gly Ser Thr Leu Asn Leu Lys Ala Glu Gly
            515                 520                 525

Ser Thr Glu Thr Ala Phe Ser Ile Glu Asn Asp Leu Asn Leu Asn Ala
530                 535                 540

Thr Gly Gly Asn Ile Thr Ile Arg Gln Val Glu Gly Thr Asp Ser Arg
545                 550                 555                 560

Val Asn Lys Gly Val Ala Ala Lys Lys Asn Ile Thr Phe Lys Gly Gly
                565                 570                 575

Asn Ile Thr Phe Gly Ser Gln Lys Ala Thr Thr Glu Ile Lys Gly Asn
            580                 585                 590

Val Thr Ile Asn Lys Asn Thr Asn Ala Thr Leu Arg Gly Ala Asn Phe
        595                 600                 605

Ala Glu Asn Lys Ser Pro Leu Asn Ile Ala Gly Asn Val Ile Asn Asn
610                 615                 620

Gly Asn Leu Thr Thr Ala Gly Ser Ile Ile Asn Ile Ala Gly Asn Leu
625                 630                 635                 640

Thr Val Ser Lys Gly Ala Asn Leu Gln Ala Ile Thr Asn Tyr Thr Phe
                645                 650                 655

Asn Val Ala Gly Ser Phe Asp Asn Asn Gly Ala Ser Asn Ile Ser Ile
            660                 665                 670

Ala Arg Gly Gly Ala Lys Phe Lys Asp Ile Asn Asn Thr Ser Ser Leu
        675                 680                 685

Asn Ile Thr Thr Asn Ser Asp Thr Thr Tyr Arg Thr Ile Ile Lys Gly
690                 695                 700

Asn Ile Ser Asn Lys Ser Gly Asp Leu Asn Ile Ile Asp Lys Lys Ser
705                 710                 715                 720

Asp Ala Glu Ile Gln Ile Gly Gly Asn Ile Ser Gln Lys Glu Gly Asn
                725                 730                 735

Leu Thr Ile Ser Ser Asp Lys Val Asn Ile Thr Asn Gln Ile Thr Ile
            740                 745                 750

Lys Ala Gly Val Glu Gly Gly Arg Ser Asp Ser Ser Glu Ala Glu Asn
        755                 760                 765

Ala Asn Leu Thr Ile Gln Thr Lys Glu Leu Lys Leu Ala Gly Asp Leu
770                 775                 780

Asn Ile Ser Gly Phe Asn Lys Ala Glu Ile Thr Ala Lys Asn Gly Ser
785                 790                 795                 800

Asp Leu Thr Ile Gly Asn Ala Ser Gly Gly Asn Ala Asp Ala Lys Lys
                805                 810                 815

Val Thr Phe Asp Lys Val Lys Asp Ser Lys Ile Ser Thr Asp Gly His
            820                 825                 830

Asn Val Thr Leu Asn Ser Glu Val Lys Thr Ser Asn Gly Ser Ser Asn
        835                 840                 845

Ala Gly Asn Asp Asn Ser Thr Gly Leu Thr Ile Ser Ala Lys Asp Val
850                 855                 860

Thr Val Asn Asn Asn Val Thr Ser His Lys Thr Ile Asn Ile Ser Ala
865                 870                 875                 880

Ala Ala Gly Asn Val Thr Thr Lys Glu Gly Thr Thr Ile Asn Ala Thr
                885                 890                 895
```

```
Thr Gly Ser Val Glu Val Thr Ala Gln Asn Gly Thr Ile Lys Gly Asn
            900                 905                 910

Ile Thr Ser Gln Asn Val Thr Val Thr Ala Thr Glu Asn Leu Val Thr
            915                 920                 925

Thr Glu Asn Ala Val Ile Asn Ala Thr Ser Gly Thr Val Asn Ile Ser
            930                 935                 940

Thr Lys Thr Gly Asp Ile Lys Gly Gly Ile Glu Ser Thr Ser Gly Asn
945                 950                 955                 960

Val Asn Ile Thr Ala Ser Gly Asn Thr Leu Lys Val Ser Asn Ile Thr
                965                 970                 975

Gly Gln Asp Val Thr Val Thr Ala Asp Ala Gly Ala Leu Thr Thr Thr
            980                 985                 990

Ala Gly Ser Thr Ile Ser Ala Thr Thr Gly Asn Ala Asn Ile Thr Thr
            995                 1000                1005

Lys Thr Gly Asp Ile Asn Gly Lys Val Glu Ser Ser Gly Ser Val
            1010                1015                1020

Thr Leu Val Ala Thr Gly Ala Thr Leu Ala Val Gly Asn Ile Ser Gly
1025                1030                1035                1040

Asn Thr Val Thr Ile Thr Ala Asp Ser Gly Lys Leu Thr Ser Thr Val
            1045                1050                1055

Gly Ser Thr Ile Asn Gly Thr Asn Ser Val Thr Ser Ser Gln Ser
            1060                1065                1070

Gly Asp Ile Glu Gly Thr Ile Ser Gly Asn Thr Val Asn Val Thr Ala
            1075                1080                1085

Ser Thr Gly Asp Leu Thr Ile Gly Asn Ser Ala Lys Val Glu Ala Lys
            1090                1095                1100

Asn Gly Ala Ala Thr Leu Thr Ala Glu Ser Gly Lys Leu Thr Thr Gln
1105                1110                1115                1120

Thr Gly Ser Ser Ile Thr Ser Ser Asn Gly Gln Thr Thr Leu Thr Ala
            1125                1130                1135

Lys Asp Ser Ser Ile Ala Gly Asn Ile Asn Ala Ala Asn Val Thr Leu
            1140                1145                1150

Asn Thr Thr Gly Thr Leu Thr Thr Thr Gly Asp Ser Lys Ile Asn Ala
            1155                1160                1165

Thr Ser Gly Thr Leu Thr Ile Asn Ala Lys Asp Ala Lys Leu Asp Gly
            1170                1175                1180

Ala Ala Ser Gly Asp Arg Thr Val Asn Ala Thr Asn Ala Ser Gly
1185                1190                1195                1200

Ser Gly Asn Val Thr Ala Lys Thr Ser Ser Val Asn Ile Thr Gly
            1205                1210                1215

Asp Leu Asn Thr Ile Asn Gly Leu Asn Ile Ile Ser Glu Asn Gly Arg
            1220                1225                1230

Asn Thr Val Arg Leu Arg Gly Lys Glu Ile Asp Val Lys Tyr Ile Gln
            1235                1240                1245

Pro Gly Val Ala Ser Val Glu Glu Val Ile Glu Ala Lys Arg Val Leu
            1250                1255                1260

Glu Lys Val Lys Asp Leu Ser Asp Glu Glu Arg Glu Thr Leu Ala Lys
1265                1270                1275                1280

Leu Gly Val Ser Ala Val Arg Phe Val Glu Pro Asn Asn Ala Ile Thr
            1285                1290                1295

Val Asn Thr Gln Asn Glu Phe Thr Thr Lys Pro Ser Ser Gln Val Thr
            1300                1305                1310

Ile Ser Glu Gly Lys Ala Cys Phe Ser Ser Gly Asn Gly Ala Arg Val
```

1315                 1320                 1325

Cys Thr Asn Val Ala Asp Asp Gly Gln Gln
            1330                1335

(2) INFORMATION FOR SEQ ID NO:10:

(i) SEQUENCE CHARACTERISTICS:
        (A) LENGTH: 1529 amino acids
        (B) TYPE: amino acid
        (C) STRANDEDNESS: single
        (D) TOPOLOGY: linear (xi) SEQUENCE DESCRIPTION: SEQ ID NO:10:

Gly Met Ser Val Val His Gly Thr Ala Thr Met Gln Val Asp Gly Asn
    1               5                   10                  15

Lys Thr Thr Ile Arg Asn Ser Val Asn Ala Ile Ile Asn Trp Lys Gln
                    20                  25                  30

Phe Asn Ile Asp Gln Asn Glu Met Glu Gln Phe Leu Gln Glu Ser Ser
                35                  40                  45

Asn Ser Ala Val Phe Asn Arg Val Thr Ser Asp Gln Ile Ser Gln Leu
        50                  55                  60

Lys Gly Ile Leu Asp Ser Asn Gly Gln Val Phe Leu Ile Asn Pro Asn
    65                  70                  75                  80

Gly Ile Thr Ile Gly Lys Asp Ala Ile Ile Asn Thr Asn Gly Phe Thr
                    85                  90                  95

Ala Ser Thr Leu Asp Ile Ser Asn Glu Asn Ile Lys Ala Arg Asn Phe
                100                 105                 110

Thr Leu Glu Gln Thr Lys Asp Lys Ala Leu Ala Glu Ile Val Asn His
                115                 120                 125

Gly Leu Ile Thr Val Gly Lys Asp Gly Ser Val Asn Leu Ile Gly Gly
            130                 135                 140

Lys Val Lys Asn Glu Gly Val Ile Ser Val Asn Gly Gly Ser Ile Ser
    145                 150                 155                 160

Leu Leu Ala Gly Gln Lys Ile Thr Ile Ser Asp Ile Ile Asn Pro Thr
                    165                 170                 175

Ile Thr Tyr Ser Ile Ala Ala Pro Glu Asn Glu Ala Ile Asn Leu Gly
                180                 185                 190

Asp Ile Phe Ala Lys Gly Gly Asn Ile Asn Val Arg Ala Ala Thr Ile
            195                 200                 205

Arg Asn Lys Gly Lys Leu Ser Ala Asp Ser Val Ser Lys Asp Lys Ser
        210                 215                 220

Gly Asn Ile Val Leu Ser Ala Lys Glu Gly Glu Ala Glu Ile Gly Gly
    225                 230                 235                 240

Val Ile Ser Ala Gln Asn Gln Ala Lys Gly Gly Lys Leu Met Ile
                    245                 250                 255

Thr Gly Asp Lys Val Thr Leu Lys Thr Gly Ala Val Ile Asp Leu Ser
                260                 265                 270

Gly Lys Glu Gly Gly Glu Thr Tyr Leu Gly Gly Asp Glu Arg Gly Glu
            275                 280                 285

Gly Lys Asn Gly Ile Gln Leu Ala Lys Lys Thr Thr Leu Glu Lys Gly
        290                 295                 300

Ser Thr Ile Asn Val Ser Gly Lys Lys Gly Gly Arg Ala Ile Val
    305                 310                 315                 320

Trp Gly Asp Ile Ala Leu Ile Asp Gly Asn Ile Asn Ala Gln Gly Ser
                    325                 330                 335

Asp Ile Ala Lys Thr Gly Gly Phe Val Glu Thr Ser Gly His Asp Leu

```
                340             345             350
    Ser Ile Gly Asp Asp Val Ile Val Asp Ala Lys Glu Trp Leu Leu Asp
                355             360             365

Pro Asp Asp Val Ser Ile Glu Thr Leu Thr Ser Gly Arg Asn Asn Thr
                370             375             380

Gly Glu Asn Gln Gly Tyr Thr Thr Gly Asp Gly Thr Lys Glu Ser Pro
    385             390             395             400

Lys Gly Asn Ser Ile Ser Lys Pro Thr Leu Thr Asn Ser Thr Leu Glu
                405             410             415

Gln Ile Leu Arg Arg Gly Ser Tyr Val Asn Ile Thr Ala Asn Asn Arg
                420             425             430

Ile Tyr Val Asn Ser Ser Ile Asn Leu Ser Asn Gly Ser Leu Thr Leu
                435             440             445

His Thr Lys Arg Asp Gly Val Lys Ile Asn Gly Asp Ile Thr Ser Asn
                450             455             460

Glu Asn Gly Asn Leu Thr Ile Lys Ala Gly Ser Trp Val Asp Val His
    465             470             475             480

Lys Asn Ile Thr Leu Gly Thr Gly Phe Leu Asn Ile Val Ala Gly Asp
                485             490             495

Ser Val Ala Phe Glu Arg Glu Gly Asp Lys Ala Arg Asn Ala Thr Asp
                500             505             510

Ala Gln Ile Thr Ala Gln Gly Thr Ile Thr Val Asn Lys Asp Asp Lys
                515             520             525

Gln Phe Arg Phe Asn Asn Val Ser Ile Asn Gly Thr Gly Lys Gly Leu
                530             535             540

Lys Phe Ile Ala Asn Gln Asn Asn Phe Thr His Lys Phe Asp Gly Glu
    545             550             555             560

Leu Asn Ile Ser Gly Ile Val Thr Ile Asn Gln Thr Thr Lys Lys Asp
                565             570             575

Val Lys Tyr Trp Asn Ala Ser Lys Asp Ser Tyr Trp Asn Val Ser Ser
                580             585             590

Leu Thr Leu Asn Thr Val Gln Lys Phe Thr Phe Ile Lys Phe Val Asp
                595             600             605

Ser Gly Ser Asn Ser Gln Asp Leu Arg Ser Ser Arg Arg Ser Phe Ala
                610             615             620

Gly Val His Phe Asn Gly Ile Gly Gly Lys Thr Asn Phe Asn Ile Gly
    625             630             635             640

Ala Asn Ala Lys Ala Leu Phe Lys Leu Lys Pro Asn Ala Ala Thr Asp
                645             650             655

Pro Lys Lys Glu Leu Pro Ile Thr Phe Asn Ala Asn Ile Thr Ala Thr
                660             665             670

Gly Asn Ser Asp Ser Ser Val Met Phe Asp Ile His Ala Asn Leu Thr
                675             680             685

Ser Arg Ala Ala Gly Ile Asn Met Asp Ser Ile Asn Ile Thr Gly Gly
                690             695             700

Leu Asp Phe Ser Ile Thr Ser His Asn Arg Asn Ser Asn Ala Phe Glu
    705             710             715             720

Ile Lys Lys Asp Leu Thr Ile Asn Ala Thr Gly Ser Asn Phe Ser Leu
                725             730             735

Lys Gln Thr Lys Asp Ser Phe Tyr Asn Glu Tyr Ser Lys His Ala Ile
                740             745             750

Asn Ser Ser His Asn Leu Thr Ile Leu Gly Gly Asn Val Thr Leu Gly
                755             760             765
```

-continued

```
Gly Glu Asn Ser Ser Ser Ser Ile Thr Gly Asn Ile Asn Ile Thr Asn
770                 775                 780

Lys Ala Asn Val Thr Leu Gln Ala Asp Thr Ser Asn Ser Asn Thr Gly
785                 790                 795                 800

Leu Lys Lys Arg Thr Leu Thr Leu Gly Asn Ile Ser Val Glu Gly Asn
                805                 810                 815

Leu Ser Leu Thr Gly Ala Asn Ala Asn Ile Val Gly Asn Leu Ser Ile
            820                 825                 830

Ala Glu Asp Ser Thr Phe Lys Gly Glu Ala Ser Asp Asn Leu Asn Ile
            835                 840                 845

Thr Gly Thr Phe Thr Asn Asn Gly Thr Ala Asn Ile Asn Ile Lys Gln
850                 855                 860

Gly Val Val Lys Leu Gln Gly Asp Ile Asn Asn Lys Gly Gly Leu Asn
865                 870                 875                 880

Ile Thr Thr Asn Ala Ser Gly Thr Gln Lys Thr Ile Ile Asn Gly Asn
                885                 890                 895

Ile Thr Asn Glu Lys Gly Asp Leu Asn Ile Lys Asn Ile Lys Ala Asp
                900                 905                 910

Ala Glu Ile Gln Ile Gly Gly Asn Ile Ser Gln Lys Gly Asn Leu
            915                 920                 925

Thr Ile Ser Ser Asp Lys Val Asn Ile Thr Asn Gln Ile Thr Ile Lys
            930                 935                 940

Ala Gly Val Glu Gly Gly Arg Ser Asp Ser Ser Glu Ala Glu Asn Ala
945                 950                 955                 960

Asn Leu Thr Ile Gln Thr Lys Glu Leu Lys Leu Ala Gly Asp Leu Asn
                965                 970                 975

Ile Ser Gly Phe Asn Lys Ala Glu Ile Thr Ala Lys Asn Gly Ser Asp
                980                 985                 990

Leu Thr Ile Gly Asn Ala Ser Gly Gly Asn Ala Asp Ala Lys Lys Val
            995                 1000                1005

Thr Phe Asp Lys Val Lys Asp Ser Lys Ile Ser Thr Asp Gly His Asn
            1010                1015                1020

Val Thr Leu Asn Ser Glu Val Lys Thr Ser Asn Gly Ser Ser Asn Ala
1025                1030                1035                1040

Gly Asn Asp Asn Ser Thr Gly Leu Thr Ile Ser Ala Lys Asp Val Thr
                1045                1050                1055

Val Asn Asn Asn Val Thr Ser His Lys Thr Ile Asn Ile Ser Ala Ala
                1060                1065                1070

Ala Gly Asn Val Thr Thr Lys Glu Gly Thr Thr Ile Asn Ala Thr Thr
                1075                1080                1085

Gly Ser Val Glu Val Thr Ala Gln Asn Gly Thr Ile Lys Gly Asn Ile
            1090                1095                1100

Thr Ser Gln Asn Val Thr Val Thr Ala Thr Glu Asn Leu Val Thr Thr
1105                1110                1115                1120

Glu Asn Ala Val Ile Asn Ala Thr Ser Gly Thr Val Asn Ile Ser Thr
                1125                1130                1135

Lys Thr Gly Asp Ile Lys Gly Gly Ile Glu Ser Thr Ser Gly Asn Val
                1140                1145                1150

Asn Ile Thr Ala Ser Gly Asn Thr Leu Lys Val Ser Asn Ile Thr Gly
                1155                1160                1165

Gln Asp Val Thr Val Thr Ala Asp Ala Gly Ala Leu Thr Thr Thr Ala
            1170                1175                1180

Gly Ser Thr Ile Ser Ala Thr Thr Gly Asn Ala Asn Ile Thr Thr Lys
1185                1190                1195                1200
```

-continued

```
Thr Gly Asp Ile Asn Gly Lys Val Glu Ser Ser Gly Ser Val Thr
            1205                1210                1215
Leu Val Ala Thr Gly Ala Thr Leu Ala Val Gly Asn Ile Ser Gly Asn
            1220                1225                1230
Thr Val Thr Ile Thr Ala Asp Ser Gly Lys Leu Thr Ser Thr Val Gly
            1235                1240                1245
Ser Thr Ile Asn Gly Thr Asn Ser Val Thr Thr Ser Ser Gln Ser Gly
        1250                1255                1260
Asp Ile Glu Gly Thr Ile Ser Gly Asn Thr Val Asn Val Thr Ala Ser
1265                1270                1275                1280
Thr Gly Asp Leu Thr Ile Gly Asn Ser Ala Lys Val Glu Ala Lys Asn
            1285                1290                1295
Gly Ala Ala Thr Leu Thr Ala Glu Ser Gly Lys Leu Thr Thr Gln Thr
            1300                1305                1310
Gly Ser Ser Ile Thr Ser Ser Asn Gly Gln Thr Thr Leu Thr Ala Lys
            1315                1320                1325
Asp Ser Ser Ile Ala Gly Asn Ile Asn Ala Ala Asn Val Thr Leu Asn
        1330                1335                1340
Thr Thr Gly Thr Leu Thr Thr Thr Gly Asp Ser Lys Ile Asn Ala Thr
1345                1350                1355                1360
Ser Gly Thr Leu Thr Ile Asn Ala Lys Asp Ala Lys Leu Asp Gly Ala
            1365                1370                1375
Ala Ser Gly Asp Arg Thr Val Val Asn Ala Thr Asn Ala Ser Gly Ser
            1380                1385                1390
Gly Asn Val Thr Ala Lys Thr Ser Ser Ser Val Asn Ile Thr Gly Asp
            1395                1400                1405
Leu Asn Thr Ile Asn Gly Leu Asn Ile Ile Ser Glu Asn Gly Arg Asn
        1410                1415                1420
Thr Val Arg Leu Arg Gly Lys Glu Ile Asp Val Lys Tyr Ile Gln Pro
1425                1430                1435                1440
Gly Val Ala Ser Val Glu Glu Val Ile Glu Ala Lys Arg Val Leu Glu
            1445                1450                1455
Lys Val Lys Asp Leu Ser Asp Glu Glu Arg Glu Thr Leu Ala Lys Leu
            1460                1465                1470
Gly Val Ser Ala Val Arg Phe Val Glu Pro Asn Asn Ala Ile Thr Val
            1475                1480                1485
Asn Thr Gln Asn Glu Phe Thr Thr Lys Pro Ser Ser Gln Val Thr Ile
        1490                1495                1500
Ser Glu Gly Lys Ala Cys Phe Ser Ser Gly Asn Gly Ala Arg Val Cys
1505                1510                1515                1520
Thr Asn Val Ala Asp Asp Gly Gln Gln
            1525
```